(12) United States Patent
Shapiro et al.

(10) Patent No.: US 8,871,751 B2
(45) Date of Patent: Oct. 28, 2014

(54) COMPOSITIONS AND METHODS RELATING TO NUCLEAR HORMONE AND STEROID HORMONE RECEPTORS INCLUDING INHIBITORS OF ESTROGEN RECEPTOR ALPHA-MEDIATED GENE EXPRESSION AND INHIBITION OF BREAST CANCER

(75) Inventors: David J. Shapiro, Urbana, IL (US); Chengjian Mao, Savoy, IL (US); Milu Tresa Cherian, Champaign, IL (US); Nicole M. Patterson, Rockford, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1288 days.

(21) Appl. No.: 12/355,949

(22) Filed: Jan. 19, 2009

(65) Prior Publication Data
US 2009/0291972 A1 Nov. 26, 2009

Related U.S. Application Data

(60) Provisional application No. 61/022,126, filed on Jan. 18, 2008, provisional application No. 61/061,227, filed on Jun. 13, 2008.

(51) Int. Cl.
*A61K 31/395* (2006.01)
*A61K 31/522* (2006.01)

(52) U.S. Cl.
CPC .................................. *A61K 31/522* (2013.01)
USPC ....................................................... 514/183

(58) Field of Classification Search
None
See application file for complete search history.

(56) References Cited

U.S. PATENT DOCUMENTS

| | | | |
|---|---|---|---|
| 3,624,215 | A | 11/1971 | Stein et al. |
| 3,624,216 | A | 11/1971 | Stein et al. |
| 5,587,378 | A | 12/1996 | Suzuki et al. |
| 5,670,498 | A | 9/1997 | Suzuki et al. |
| 5,734,051 | A | 3/1998 | Spicer et al. |
| 5,734,052 | A | 3/1998 | Peet et al. |
| 7,253,176 | B1 | 8/2007 | Waer et al. |
| 2005/0187267 | A1 | 8/2005 | Hamann et al. |
| 2007/0265296 | A1 | 11/2007 | Dalton et al. |

FOREIGN PATENT DOCUMENTS

| | | |
|---|---|---|
| EP | 0 011 399 | 5/1980 |
| EP | 0 430 300 | 6/1991 |
| EP | 0 590 919 | 4/1994 |
| EP | 0 956 855 | 11/1999 |

(Continued)

OTHER PUBLICATIONS

Hayallah, A. and Famulok, M. Heterocycles, vol. 74, 2007, pp. 369-382.*

(Continued)

*Primary Examiner* — San-Ming Hui
*Assistant Examiner* — Jeanmarie Calvillo
(74) *Attorney, Agent, or Firm* — Lathrop & Gage LLP

(57) ABSTRACT

The disclosure herein relates to nuclear hormone receptors including steroid hormone receptors, for example in connection with estrogen, progesterone, and androgen. Embodiments of compositions and methods are disclosed including such relating to compounds, including substituted theophyllines, capable of functioning as inhibitors of estrogen receptor alpha-mediated gene expression and having the ability to modify cancer cells and treat cancer, including breast cancers and resistant breast cancers, particularly those that are resistant to tamoxifen. In embodiments, methods of inhibiting breast cancer cells and resistant breast cancer cells are provided. In embodiments, a useful inhibitor compound includes TPSF/NSC 97998 and other compounds.

21 Claims, 12 Drawing Sheets

(56) References Cited

FOREIGN PATENT DOCUMENTS

| WO | WO 94/25462 | 11/1994 |
|----|-------------|---------|
| WO | WO 2004/106337 | 12/2004 |
| WO | WO 2006/091897 | 8/2006 |
| WO | WO 2007/065595 | 6/2007 |
| WO | WO 2007/105023 | 9/2007 |

OTHER PUBLICATIONS

Abukhdeir et al., Tamoxifen-Stimulated Growth of Breast Cancer Due to p21 Loss, Proc. Nat. Acad. Sci. USA 105(1):288-293, Jan. 8, 2008.
Anderson et al., Predictors of Response to Aromatase Inhibitors, J Steroid Biochem. Mol. Biol. 106:49-54, May 24, 2007.
Anzick et al., AIB1, a Steroid Receptor Coactivator Amplified in Breast and Ovarian Cancer, Science 277:965-968, Aug. 15, 1997.
Arkin et al., Small-Molecule Inhibitors of Protein-Protein Interactions: Progressing Towards the Dream, Nat. Rev. Drug Discov. 3(4):301-317, Apr. 2004.
Arnold et al., Discovery of Small Molecule Inhibitors of the Interaction of the Thyroid Receptor with Transcriptional Coregulators, J. Biol. Chem. 280(52):43048-43055, Dec. 30, 2005.
Arteaga et al., Reversal of Tamoxifen Resistance of Human Breast Carcinomas in Vivo by Neutralizing Antibodies to Transforming Growth Factor-Beta, J. Nat. Cancer Inst. 91:46-53, Jan. 6, 1999.
Askew et al., Modulation of Androgen Receptor Activation Function 2 by Testosterone and Dihydrotestosterone, J. Biol. Chem. 282(35):25801-25816, Aug. 31, 2007.
Baldwin et al., BG-1 Ovarian Cell Line: An Alternative Model for Examining Estrogen-Dependent Growth In Vitro, In Vitro Cell Dev. Biol. Anim. 34(8):649-654, Sep. 1998.
Balk, Androgen Receptor as a target in Androgen-Independent Prostate Cancer, Urology 60(Suppl 3A):132-139, Sep. 2002.
Baraldi et al., Novel 8-heterocyclyl Xanthine Derivatives in Drug Development—An Update, Exp. Opin. Drug Disc. 2(9):1161-1183, Sep. 1, 2007, Abstract only.
Boccardo, Switching Trial of Adjuvant Tamoxifen with an Aromatase Inhibitor in Postmenopausal Patients with Breast Cancer, Clin. Breast Cancer 5(Suppl 1):S13-S17, Sep. 2004.
Bruns et al., Adenosine Receptor Binding: Structure-Activity Analysis Generates Extremely Potent Xanthine Antagonists, Proc. Natl. Acad. Sci USA 80:2077-2080, Apr. 1983.
Canney et al., Clinical Significance of Tamoxifen Withdrawal Response, Lancet 1:36, Jan. 3, 1987.
Carroll et al., Estrogen Receptor Target Gene: An Evolving Concept, Mol. Endocrinol. 20:1707-1714, Aug. 2006.
Carroll et al., Chromosome-Wide Mapping of Estrogen Receptor Binding Reveals Long-Range Regulation Requiring the Forkhead Protein FoxA1, Cell 122:33-43, Jul. 12, 2005.
Castro-Rivera et al., Estrogen Regulation of Cyclin D1 Gene Expression in ZR-75 Breast Cancer Cells Involves Multiple Enhancer Elements, J. Biol. Chem. 276:30853-30861, Aug. 17, 2001.
Chen et al., Duration of Nuclear NF-kappaB Action Regulated by Reversible Acetylation, Science 293:1653-1657, Aug. 31, 2001.
Chen et al., Molecular Determinants of Resistance to Antiandrogen Therapy, Nat. Med. 10(1):33-39, Jan. 2004.
Cheng et al., Tamoxifen Induction of CCAAT Enhancer-Binding Protein α is Required for Tamoxifen-Induced Apoptosis, J. Biol. Chem. 282(42):30535-30543, Oct. 19, 2007.
Clarke et al., Antiestrogen Resistance in Breast Cancer and the Role of Estrogen Receptor Signaling, Oncogene 22(47):7316-7339, 2003.
Culig et al., Expression and Function of Androgen Receptor Coactivators n Prostate Cancer, J. Steroid Biochem. Mol. Biol. 92(4):265-271, 2004.
Cunningham et al., Expression of High Levels of Human Proteinase Inhibitor 9 Blocks Both Perforin/granzyme and Fas/Fas Ligand-Mediated Cytotoxicity, Cell Immunol. 245:32-41, May 8, 2007.
Daly et al., 1,3-Dialkyl-8-(p-sulfophenyl)xanthines: Potent Water-Soluble Antagonists for A1- and A2-Adenosine Receptors, J. Med. Chem. 28(4):487-92, 1985.
Daly et al., Analogous of Caffeine and Theophylline: Effect of Structural Alterations on Affinity at Adenosine Receptors, J. Med. Chem. 29:1305-1308, 1986.
Debes et al., Mechanisms of Androgen-Refractory Prostate Cancer, N. Eng. .J Med. 351(15):1488-1490, Oct. 7, 2004.
Deroo et al., Estrogen Receptors and Human Disease, J. Clin. Invest. 116:561-570, Mar. 2006.
Dietz et al., The Synthesis and Pharmacologic Evaluation of a Series of 8-Alkylthio-Thiated Theophyllines, J. Med. Chem. 9(4):500-506, Jul. 1966.
Dietz et al., The Synthesis of Some 8-Alkylthio-2-thiotheophyllines and 8-Alkylthio-6-thiotheophyllnies, J. Med. Chem. 9(1):160, 1966.
Estebanez-Perpina et al., A Surface on the Androgen Receptor that Allosterically Regulates Coactivator Binding, Proc. Nat. Acad. Sci. USA 104(41):16074-16079, Oct. 9, 2007.
Fabian et al., Selective Estrogen-Receptor Modulators for Primary Prevention of Breast Cancer, J. Clin. Oncol. 23:1644-1655, Mar. 10, 2005.
Feldman et al., The Development of Androgen-Independent Prostate Cancer, Nat. Rev. Cancer 1(1):34-45, Oct. 2001.
Fowler et al., Increases in Estrogen Receptor-Alpha Concentration in Breast Cancer Cells Promote Serine 118/104/106-Independent AF-1 Transactivation and Growth in the Absence of Estrogen, FASEB J. 18:81-93, Jan. 2004.
Fowler et al., Altered Target Gene Regulation Controlled by Estrogen Receptor-Alpha Concentration, Mol. Endocrinol. 20:291-301, Feb. 2006.
Frasor et al., Gene Expression Preferentially Regulated by Tamoxifen in Breast Cancer Cells and Correlations with Clinical Outcome, Cancer Res, 66(14):7334-7340, Jul. 15, 2006.
Frydenberg et al., Prostate Cancer Diagnosis and Management, Lancet 349(9066):1681-1687, Jun. 7, 1997.
Gaddipati et al., Frequent Detection of Codon 877 Mutation in the Andorgen Receptor Gene in Advanced Prostate Cancers, Cancer Res. 54(11):2861-2864, Jun. 1, 1994.
Gelmann, Molecular Biology of the Androgen Receptor, J. Clin. Oncol. 20(13):3001-3015, Jul. 1, 2002.
Glass et al., The Coregulator Exchange in Transcriptional Functions of Nuclear Receptors, Genes Dev. 14:121-141, 2000.
Gondova et al., Determination of Some Thermodynamic Characteristics of Melting of 8-alkyltheophyllines by the DSC Method, Thermochimica Acta 156:147-155, 1989.
Goodsell et al., 8-Substituted Theophyllines. In vitro Inhibition of 3',5'-Cyclic Adenosine Monophosphate Phosphodiesterase and Pharmacological Spectrum in Mice, J. Med. Chem. 14(12):1202-1205, Dec. 1971.
Gradishar et al., Selective Estrogen Receptor Modulators and Prevention of Invasive Breast Cancer, J. Am. Med. Assoc. 295(23):2784-2786, Jun. 21, 2006.
Gregory et al., Androgen Receptor Stabilization in Recurrent Prostate Cancer is Associated with Hypersensitivity to Low Androgen, Cancer Res. 61(7):2892-2898, Apr. 1, 2001.
Grillo et al., Validation of Cyclin D1/CDK4 as an Anticancer Drug Target in MCF7 Breast Cancer Cells: Effect of Regulated Overexpression of Cyclin D1 and siRNA mediated Inhibition of Endogenous Cyclin D1 and CDK4 Expression, Breast Cancer Res. Treat. 95:185-194, 2006.
Hager et al., Aryl Ketones and Thio Morpholides in the Synthesis of 8-Substituted Xanthines, J. Am. Pharm. Assoc. 44:649-653, Nov. 1955.
Henderson et al., Hormonal Carcinogenesis, Carcinogenesis 21(3):427-433, 2000.
Hergenrother, Obtaining and Screening Compound Collections: A User's Guide and a Call to Chemists, Curr. Opin. Chem. Biol. 10(3):213-218, Jun. 2006.
Hoffmann et al., Characterization of New Estrogen Receptor Destabilizing Compounds: Effects on Estrogen Sensitive and Tamoxifen-Resistant Breast Cancer, J. Nat. Cancer Inst. 96:210-218, Feb. 4, 2004.
Ichikawa et al., Hormone Treatment for Prostate Cancer: Current Issues and Future Directions, Cancer Chemother. Pharmacol. 56(Suppl 1):s58-s63, Nov. 5, 2005.

(56) References Cited

OTHER PUBLICATIONS

Ishii et al., Tamoxifen Stimulates the Growth of Cyclin D1-Overexpressing Breast Cancer Cells by Promoting the Activation of Signal Transducer and Activator of Transcription 3, Cancer Res. 68:852-860, Feb. 1, 2008.

Jacobson et al., Sulfur-Containing 1,3-dialkylxanthine Derivatives as Selective Antagonists at Al-Adenosine Receptors, J. Med. Chem. 32(8):1873-1879, 1989.

Jakacka et al., Estrogen Receptor Binding to DNA is Not Required for its Activity Through the Nonclassical AP1 Pathway, J. Biol. Chem. 276:13615-13621, Apr. 27, 2001.

Jiang et al., Interplay Between the Levels of Estrogen and Estrogen Receptor Controls the Level of the Granzyme Inhibitor, Proteinase Inhibitor 9 and Susceptibility to Immune Surveillance by Natural Killer Cells, Oncogene 26:4106-4114, Jan. 22, 2007.

Jiang et al., Estrogen Induction of the Granzyme B Inhibitor, Proteinase Inhibitor 9, Protects Cells Against Apoptosis Mediated by Cytotoxic T Lymphocytes and Natural Killer Cells, Endocrinology 147:1419-1426, 2006; first published online Nov. 23, 2005.

Jiang et al., Low Concentrations of the Soy phytoestrogen genistein Induce Proteinase Inhibitor 9 and Block Killing of Breast Cancer cells by Immune Cells, Endocrinology 149(11):5366-5373, 2008; first published online Jul. 31, 2008.

Katzenellenbogen et al., William L. McGuire Memorial Lecture. Antiestrogens: Mechanisms of Action and Resistance in Breast Cancer, Breast Cancer Res. Treat. 44:23-38, 1997.

Katzenellenbogen, Mechanisms of Action and Cross-Talk Between Estrogen Receptor and Progesterone Receptor Pathways, J. Soc. Gynecol. Investig. 7(Suppl):S33-S37, 2000.

Kilker et al., Cyclin D1 is Necessary for Tamoxifen-Induced Cell Cycle Progression in Human Breast Cancer Cells, Cancer Res. 66:11478-11484, Dec. 1, 2006.

Kisanga et al., Tamoxifen and Metabolite Concentrations in Serum and Breast Cancer Tissue During Three DOSe Regimens in a andomized Preoperative Trial, Clin. Cancer Res. 10:2336-2343, Apr. 1, 2004.

Klinge, Estrogen Receptor Interaction with Estrogen Response Elements, Nuc. Acids Res. 29(14):2905-2919, 2001.

Krieg et al., Interplay Between Estrogen Response Element Sequence and Ligands Controls in vivo Binding of Estrogen Receptor to Regulated Genes, J. Biol. Chem. 279:5025-5034, Feb. 6, 2004.

Krieg et al., A Unique Downstream Estrogen Responsive Unit Mediates Estrogen Induction of Proteinase Inhibitor-9, a Cellular Inhibitor of IL-1beta Converting Enzyme (Caspase 1), Mol. Endocrinol. 15:1971-1982, Nov. 2001.

Kummer et al., Ectopic Expression of the Serine Protease Inhibitor PI9 Modulates Death Receptor-Mediated Apoptosis, Cell Death Differ. 14:1486-1496, 2007; published online May 4, 2007.

Kung et al., Small Molecule Blockade of Transcriptional Coactivation of the Hypoxia-Inducible Factor Pathway, Cancer Cell 6(1):33-43, Jul. 2004.

Kushner et al., Estrogen Receptor Pathways to AP-1, J. Steroid Biochem. Mol. Biol. 74:311-317, 2000.

Lewis et al., Selective Estrogen Receptor Modulators (SERMs): Mechanisms of Anticarcinogenesis and Drug Resistance, Mutat. Res. 591:247-263, Aug. 3, 2005.

Li et al., A Small Molecule Smac Mimic Potentiates TRAIL- and TNFα-Mediated Cell Death, Science 305(5689):1471-1474, Sep. 3, 2004.

Mao et al., A New Small Molecule Inhibitor of Estrogen Receptor Alpha Binding to Estrogen Response Elements Blocks Estrogen-Dependent Growth of Cancer Cells, J. Biol. Chem. 283(19):12819-12830, May 9, 2008.

Mao et al., Analysis of RNA-Protein Interactions by a Microlplate-Based Fluorescence Anisotropy Assay, Anal. Biochem. 350(2):222-232, Jan. 17, 2006.

Mattick et al., Analysis of Ligand Dependence and Hormone Response Element Synergy in Transcription by Estrogen Receptor, J. Steroid. Biochem. Mol. Biol. 60(56):285-294, Mar. 1997.

McKenna et al., Minireview: Nuclear Receptor Coactivators-An Update, Endocrinology 143:2461-2465, Jul. 2002.

McKenna et al., Combinatorial Control of Gene Expression by Nuclear Receptors and Coregulators, Cell 108:465-474, Feb. 22, 2002.

Medema et al., Immune Escape of Tumors in Vivo by Expression of Cellular FLICE-Inhibitory Protein, J. Exp. Med. 190(7):1033-1038, Oct. 4, 1999.

Mineo et al., Studies on Heterocyclic Compounds. XXXII. Synthesis of 8-Substituted Theophyllines from 6-Amino-5-benzylideneamino-1,3-dimethyluracils with Nickel Peroxide, Chem. Pharm. Bull. 28(9)2835-2838, 1980.

Moerke et al., Small-Molecule Inhibition of the Interaction Between the Translation Initiation Factors eIF4E and eIF4G, Cell 128(2):257-267, Jan. 26, 2007.

Mohler et al., The Androgen Axis in Recurrent Prostate Cancer, Clin. Cancer Res. 10(2):440-448, Jan. 15, 2004.

Musgrove et al., Cyclin D1 Induction in Breast Cancer Cells Shortens G1 and is Sufficient for Cells Arrested in G1 to Complete the Cell Cycle, Proc. Nat. Acad. Sci. USA 91:8022-8026, Aug. 1994.

Naughton et al., Progressive Loss of Estrogen Receptor Alpha Cofactor Recruitment in Endocrine Resistance, Mol. Endocrinol. 21:2615-2626, Jul. 31, 2007.

Neuman et al., Cyclin D1 Stimulation of Estrogen Receptor Transcriptional Activity Independent of cdk4, Mol. Cell Biol. 17:5338-5347, Sep. 1997.

Nordeen et al., A Quantitative Comparison of Dual Control of a Hormone Response Element by Progestins and Glucocorticoids in the Same Cell Line, Mol. Endocrinol. 3(8):1270-1278, 1989.

Obrero et al., Estrogen Receptor-Dependent and Estrogen Receptorindependent Pathways for Tamoxifen and 4-Hydroxytamoxifen-Induced Programmed Cell Death, J. Biol. Chem. 277:45695-45703, Nov. 22, 2002.

O'Lone et al., Genomic Targets of Nuclear Estrogen Receptors, Mol. Endocrinol. 18:1859-1875, Aug. 2004.

Osborne et al., Crosstalk Between Estrogen Receptor and Growth Factor Receptor Pathways as a Cause for Endocrine Therapy Resistance in Breast Cancer, Clin. Cancer Res. 11(2 Pt 2):865s-870s, Jan. 15, 2005.

Ozers et al., Equilibrium Binding of Estrogen Receptor with DNA Using Fluorescence Anisotropy, J. Biol. Chem. 272(48):30405-30411, Nov. 28, 1997.

PubChem Compound, 1,3-dimethyl-8-3(phenylpropylsulfany1)-6-Sulfanylidene-7H-Purin-2-one, NCIStruc1__001297, Mar. 26, 2005.

PubChem Compound, 8[4-(40fluorophenyl)-4-oxobutyl]sulfanyl-1,3-dimethyl-6-sulfanylidine-7H-purin-2-one, NSC 97998, Mar. 26, 2005.

Putt et al., Small-Molecule Activation of Procaspase-3 to Caspase-3 as a Personalized Anticancer Strategy, Nat. Chem. Biol. 2(10):543-550, Oct. 2006; published online Aug. 27, 2006.

Putt et al., An Enzymatic Assay for poly(ADP-ribose) Polymerase-1 (PARP-1) via the Chemical Quantitation of $NAD^+$: Application to the High-Throughput Screening of Small Molecules as Potential Inhibitors, Anal. Biochem. 326(1):78-86, Mar. 1, 2004.

Qin et al., Transcriptional Activation of Insulin-Like Growth Factor Binding Protein-4 by 17beta-estradiol in MCF-7 Cells: Role of Estrogen Receptor-Sp1 Complexes, Endocrinology 140:2501-2508, 1999.

Reese et al., Examination of the DNA-Binding Ability of Estrogen Receptor in Whole Cells: Implications for Hormone-Independent Transactivation and the Actions of Antiestrigens, Mol. Cell. Biol. 12:4531-4538, Oct. 1992.

Ried et al., Synthesen kondensierter 5-, 7- und 8-gliedriger Heterocyclen mit 2 Stickstoffatomen, Chem. Ber. 92:2902, 1959 (in German).

Rishi et al., A High-Throughput Fluorescence-Anisotropy Screen that Identifies Small Molecule Inhibitors of the DNA Binding of B-ZIP Transcription Factors, Anal. Biochem. 340(2):259-271, 2005; published online Mar. 16, 2005.

Romain et al., Biological Heterogeneity of ER-Positive Breast Cancers in the Post-Menopausal Population, Int. J. Cancer 59:17-19, 1994.

(56) References Cited

OTHER PUBLICATIONS

Sabbah et al., Estrogen Induction of the Cyclin D1 Promoter: Involvement of a cAMP Response-Like Element, Proc. Nat. Acad. Sci. USA 96:11217-11222, Sep. 1999.
Safe, Transcriptional Activation of Genes by 17 Beta-Estradiol Through Estrogen Receptor-Sp1 Interactions, Vitam. Harm. 62:231-252, 2001.
Senga et al., Oxidative Cyclization of 6-Amino-5-benzylideneamino-1,3-dimethyluracils with Thionyl Chloride. A Convenient Synthesis of 8-Substituted Theophyllines, Chem. Pharm. Bull. 25(3):495-497, 1977.
Shang et al., Molecular Determinants for the Tissue Specificity of SERMs, Science 295:2465-2468, Mar. 29, 2002.
Shiau et al., The Structural Basis of Estrogen Receptor/Coactivator Recognition and the Antagonism of this Interaction by Tamoxifen, Cell 95:927-937, Dec. 23, 1998.
Smith et al., Aromatase Inhibitors in Breast Cancer, N. Engl. J. Med. 348(24):2431-2442, Jun. 12, 2003.
Smyth et al., Antiestrogen Therapy is Active in Selected Ovarian Cancer Cases: The Use of Letrozole in Estrogen Receptor—Positive Patients, Clin. Cancer Res. 13(12):3617-3622, Jun. 15, 2007.
Steinsapir et al., Theophylline-Estrogen Interaction in the Rat Uterus: Role of the Ovary, Am. J. Physiol. Endocrinol. Metab. 242:E121-E126, 1982.
Tan et al., Dehydroepiandrosterone Activates Mutant Androgen Receptors Expressed in the Androgen-Dependent Human Prostate Cancer Xenograft CWR22 and LNCaP Cells, Mol. Endocrinol. 11(4):450-459, 1997.
Taplin et al., Androgen Receptor: A Key Molecule in the Progression of Prostate Cancer to Hormone Independence, J. Cell. Biochem. 91(3):483-490, 2004.
Taplin et al., Mutation of the Androgen-Receptor Gene in Metastic Androgen-Independent Prostate Cancer, N. Engl. J. Med. 332(21):1393-1398, May 25, 1995.
Taplin et al., Androgen Receptor Mutations in Androgen-Independent Prostate Cancer: Cancer and Leukemia Group B Study 9663, J. Clin. Oncol. 21(14):2673-267, Jul. 15, 2003.
ten Berge et al., ALK-Negative Anaplastic Large-Cell Lymphoma Demonstrates Similar Poor Prognosis to Peripheral T-Cell Lymphoma, Unspecified, Histopathology 43:462-469, 2003.
ten Berge et al., Expression Levels of Apoptosis-Related Proteins Predict Clinical Outcome in Anaplastic Large Cell Lymphoma, Blood 99:4540-4546, Jun. 15, 2001.
ten Berge et al., ALK-Negative Systemic Anaplastic Large Cell Lymphoma: Differential Diagnostic and Prognostic Aspects—A Review, J. Pathol. 200:4-15, 2003; published online Feb. 20, 2003.
Thorpe et al., Short Recurrence-Free Survival Associated with High Oestrogen Receptor Levels in the Natural History of Postmenopausal, Primary Breast Cancer, Eur. J. Cancer 29A:971-977, 1993.
van Houdt et al., Expression of the Apoptosis Inhibitor Protease Inhibitor 9 Predicts Clinical Outcome in Vaccinated Patients with Stage III and IV Melanoma, Clin. Cancer Res. 11:6400-6407, Sep. 1, 2005.
Verma et al., Ubistatins Inhibit Proteasome-Dependent Degradation by Binding the Ubiquitin Chain, Science 306(5693):117-120, Oct. 1, 2004.
Visakorpi et al., In vivo Amplification of the Androgen Receptor Gene and Pregression of Human Prostate Cancer, Nat. Genet. 9(4):401-406, Apr. 1995.
Wang et al., Disruption of Estrogen Receptor DNA Binding Domain and Related Intracellular Communication Restores Tamoxifen Sensitivity in Resistant Breast Cancer, Cancer Cell 10:487-499, Dec. 2006.
Wang et al., Suppression of Breast Cancer by Chemical Moldulation of Vulnerable Zinc Fingers in Estrogen Receptor, Nat. Med. 10(1):40-47, Jan. 2004; published online Dec. 14, 2003.
Wang et al., Fluorescent Anisotropy Microplate Assay for Analysis of Steroid Receptor-DNA Interactions, BioTechniques 37(5):807-817, Nov. 2004.
Wang et al., In vitro Fluorescence Anisotropy Analysis of the Interaction of Full-Length SRC1a with Estrogen Receptors $\alpha$ and $\beta$ Supports an Active Displacement Model for Coregulator Utilization, J. Biol. Chem. 282(5):2765-2775, Feb. 2, 2007.
Wilson et al., Development and Characterization of a Cell Line that Stably Expresses an Estrogen-Responsive Luciferase Reporter for the Detection of Estrogen Receptor Agonist and Antagonists, Toxicol. Sci. 81:69-77, 2004; advance access publication May 27, 2004.
Winer, Optimizing Endocrine Therapy for Breast Cancer, J. Clin. Oncol. 23(8):1609-1610, Mar. 10, 2005.
Yager et al., Estrogen Carcinogenesis in Breast Cancer, N. Engl. J. Med. 354(3):270-282, Jan. 19, 2006.
Zhang et al., A Simple Statistical Parameter for Use in Evaluation and Validation of High Throughput Screening Assays, J. Biomol. Screen 4(2):67-73, 1999.
Zhao et al., Glucocorticoids Can Promote Androgen-Independent Growth of Prostate Cancer Cells Through a Mutated Androgen Receptor, Nat. Med. 6(6):703-706, Jun. 2000.
Zhou et al., Delayed and Persistent ERK1/2 Activation is Required for 4-Hydroxytamoxifen-Induced Cell Death, Steroids 72:765-777, 2007; published online Jul. 7, 2007.
Zimmer et al., Potential Anticancer Compounds. III. Synthesis of Some 8-Substituted Caffeines and Theophyllines, Ohio J. Sci. 63(3):97-102, May 1963.
Coradini D. et al., Influence of different combinations of tamoxifen and toremifene on estrogen receptor-positive breast cancer cell lines, Cancer Detect Prev. 19(4):348-54, 1995 (Abstract).
Howell A. et al., Response after withdrawal of tamoxifen and progestogens in advanced breast cancer, Ann Oncol. Sep. 3(8):611-7, 1992 (Abstract).
Kretzer N. et al., A noncompetitive small molecule inhibitor of estrogen-regulated gene expression and breast cancer cell growth that enhances proteasome-dependent degradation of estrogen receptor $\alpha$, Journal of Biological Chemistry 285(43):41863-41873, Dec. 31, 2010.
Shapiro D. et al., Small molecule inhibitors as probes for estrogen and androgen receptor action, Journal of Biological Chemistry 286(6):4043-4048, Feb. 11, 2011.

* cited by examiner

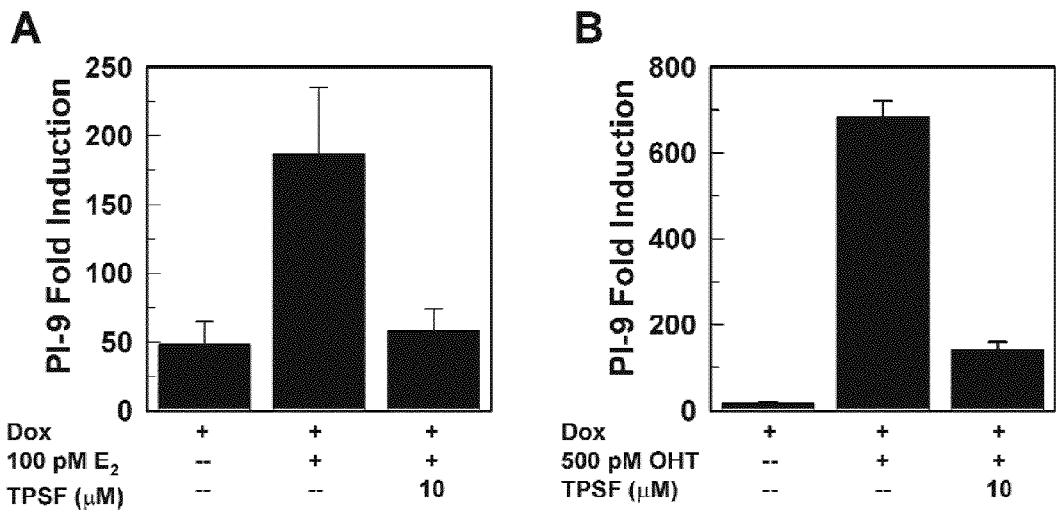
Fig. 18
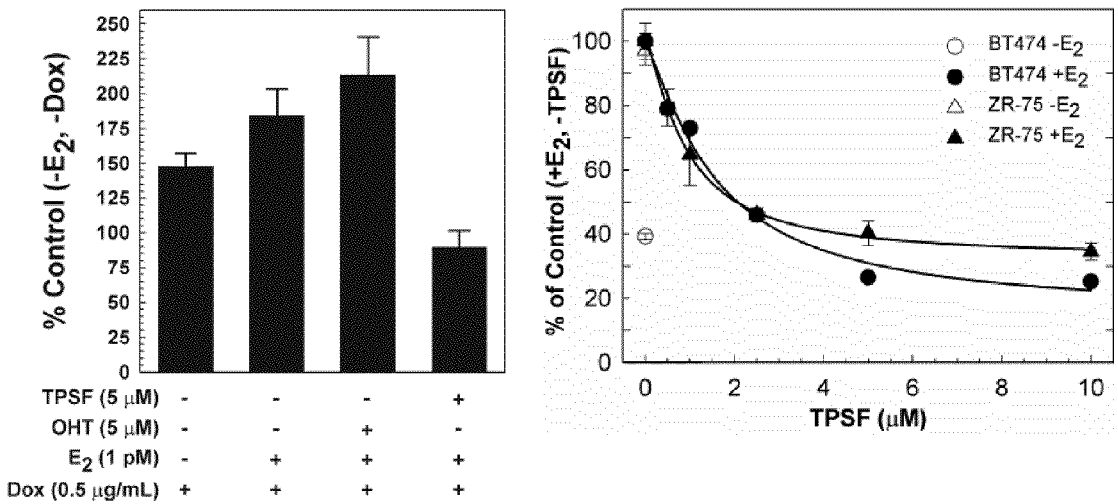
Fig. 19
Fig. 20

SEQUENCE LISTING

```
<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: Synthetic construct

<400> SEQUENCE: 1
ctagattaca ggtcacagtg accttactca                                          30

<210> SEQ ID NO 2
<211> LENGTH: 30
<212> TYPE: DNA
<213> ORGANISM: Artificial Sequence
<220> FEATURE:
<223> OTHER INFORMATION: Synthetic construct

<400> SEQUENCE: 2
ctagattacg gtacatgatg ttcttactca                                          30

<210> SEQ ID NO 3
<211> LENGTH: 30
<212> TYPE: DNA
<213> ORGANISM: Artificial Sequence
<220> FEATURE:
<223> OTHER INFORMATION: Synthetic construct

<400> SEQUENCE: 3
ctagattaca gaacaatctg ttcttactca                                          30

<210> SEQ ID NO 4
<211> LENGTH: 24
```

```
<212> TYPE: DNA
<213> ORGANISM: Artificial Sequence
<220> FEATURE:
<223> OTHER INFORMATION: Synthetic construct

<400> SEQUENCE: 4
tcatggctga agtcacctct tggt                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic construct

<400> SEQUENCE: 5
tccactggat ggtttgtcac tgga                                              24

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
tggaatgaac cgtttgacga a                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
catctgcact ggcctttgct                                                   20

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
gagggttgtg gagaagtttt tg                                                22

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
ctggcatctt cactgattct tg                                                22

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
```

```
aagccacccc acttctctct aa                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic construct

<400> SEQUENCE: 11
aatgctatca cctcccctgt gt                              22
```

COMPOSITIONS AND METHODS RELATING TO NUCLEAR HORMONE AND STEROID HORMONE RECEPTORS INCLUDING INHIBITORS OF ESTROGEN RECEPTOR ALPHA-MEDIATED GENE EXPRESSION AND INHIBITION OF BREAST CANCER

CROSS-REFERENCES TO RELATED APPLICATIONS

This application claims benefit of U.S. Provisional Patent Application Ser. No. 61/022,126 filed Jan. 18, 2008 by Shapiro et al. and U.S. Provisional Patent Application Ser. No. 61/061,227 filed Jun. 13, 2008 by Shapiro et al.; all of which are incorporated herein by reference in entirety.

STATEMENT ON FEDERALLY SPONSORED RESEARCH OR DEVELOPMENT

This invention was made with government support under Contract/Grant No. NIH PHS RO1 DK 071909 awarded by the National Institutes of Health. The government has certain rights in the invention.

BACKGROUND OF THE INVENTION

Estrogen receptor α (ERα) is a member of the steroid/nuclear receptor family of transcription regulators and mediates cell growth and metastases, and resistance to apoptosis and immunosurveillance (see references 1-5). ERα is activated by binding of 17β-estradiol ($E_2$), or by the EGF-activated ERK pathway and other signal transduction pathways (6). ERα mediated gene transcription contributes to the development and spread of breast, uterine and liver cancer (5,7,8). A role for ER action in ovarian cancer is supported by the recent finding that endocrine therapy is effective against relapsed ER containing ovarian cancers (9,10). Aromatase inhibitors that inhibit estrogen production and tamoxifen (Tam) and other Selective Estrogen Receptor Modulators (SERMs) are mainstays in treatment of estrogen-dependent cancers and have played an important role in developing our understanding of ER action (5,7,11,12). Tam and other SERMs work by competing with estrogens for binding in ER's ligand-binding pocket. Over time, tumors usually become resistant to tamoxifen and other SERMs (13-15), requiring new strategies to inhibit ERα action.

In a characterization of ER action, ERα activates gene transcription by binding to palindromic estrogen response element (ERE) DNA and ERE half sites (4,16,17). Thus, an alternative to current approaches that primarily target ER action at the level of ligand binding, is to target ERα at the level of its interaction with ERE DNA. This approach was questioned because small molecules may not disrupt the large interaction surfaces of protein-DNA and protein-protein complexes (18). Certain studies describe using a high throughput screening (HTS) approach to identify small molecules that act directly at the binding interface, or allosterically by inducing a conformational change in the protein that alters the formation of a functioning macromolecular interface (19-24). Although it was not identified by HTS, disulfide benzamide (DIBA), an ERα zinc finger inhibitor (25) enhances the antagonist activity of tamoxifen (26). In our efforts, we further developed an approach of identifying small molecule inhibitors targeting novel sites in ER action. This led to successful discoveries such as the development of compositions and methods for stimulating or inhibiting nuclear receptor hormone function.

In the field of nuclear receptors, steroid receptors, including, e.g., estrogen, androgen, and progesterone pathways, there remains a significant need for new and/or improved compositions and methods. In part an object of the invention is to meet such needs, for example by providing compositions and methods in connection with therapeutic applications. Further objects and aspects of the invention are described herein and will be apparent to one of ordinary skill in the art.

SUMMARY OF THE INVENTION

In embodiments, the invention provides compositions and methods relating to inhibition of nuclear hormones and receptors. In embodiments, the invention provides compositions and methods relating to inhibition of steroid hormones and receptors. In embodiments, the invention provides compositions and methods relating to inhibition of estrogen receptors. In particular embodiments, the invention provides compositions and methods relating to inhibition of estrogen receptor alpha binding to estrogen response elements. In embodiments, the invention provides methods of modifying or blocking estrogen-dependent growth of cancer cells. In embodiments, the invention provides compositions and methods relating to inhibition of growth of cancer cells. In embodiments, the invention provides compositions and methods relating to treatment of cancer. In an embodiment, the cancer is breast cancer, prostate cancer, uterine cancer, ovarian cancer, or liver cancer.

In embodiments, the invention provides compositions and methods relating to nuclear hormone and steroid hormone receptors including modifiers of hormone receptor-mediated gene expression. In embodiments, the invention provides compositions and methods relating to nuclear hormone and steroid hormone receptors including modifiers of hormone receptor-mediated binding to gene expression response elements. In embodiments, the invention provides compositions and methods relating to nuclear hormone and steroid hormone receptors including substituted theophylline inhibitors of estrogen receptor alpha-mediated gene expression. In embodiments, the invention provides compositions and methods relating to nuclear hormone and steroid hormone receptors including substituted theophylline inhibitors of estrogen receptor alpha binding to estrogen response elements.

In embodiments, compositions and methods of the invention are effective in modifying hormone and/or hormone receptor mediated gene expression and cell growth. In an embodiment the cell growth is cancer cell growth. In embodiments, such compositions and methods are effective without necessarily acting by a particular mechanism, e.g., the mechanism of directly inhibiting hormone receptor binding to a hormone response element. For example, an embodiment of the invention may act by binding to a hormone receptor and altering one or more properties of such receptor or the complex formed; thus there can be an indirect mechanism or other mechanisms involved resulting in modulation of gene expression and therefore cell function.

In an embodiment, the invention provides a method of inhibiting growth of a cancer cell comprising contacting said cell with an effective amount of a compound having formula FX2:

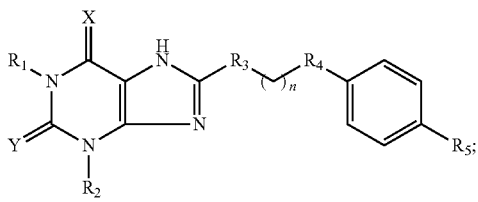

FX2 wherein X or Y each independently is S, O, or Se;

$R_1$ or $R_2$ each independently is H or $C_{1-6}$ alkyl;

$R_3$ is —S—$CH_2$—, —O—$CH_2$—, —$CH_2$—S, or —$CH_2$—O—;

$R_4$ is —C=O, —NH—C=O, —$CH_2$—, or null;

$R_5$ is F, Cl, Br, I, At, H, or other group with electronegativity from 1.5 to 4.0; and n is 1 to 6.

In an embodiment, the cancer cell is a human cancer cell. In an embodiment, the cancer cell is a breast cancer cell. In an embodiment, the cancer cell is a resistant cancer cell. In an embodiment, the resistant cancer cell has resistance to a chemotherapeutic agent selected from the group consisting of tamoxifen, 4-hydroxytamoxifen (OHT); a selective estrogen receptor modulator, and an aromatase inhibitor.

In an embodiment, the compound has a structural formula selected from the group consisting of compounds having formulas corresponding to TPSF/97998, 99676, and TPBM/95910:

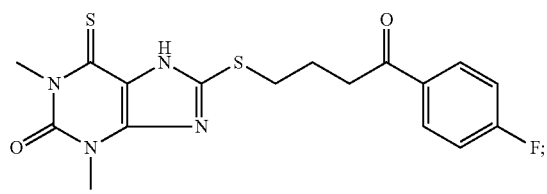 [SMILES: Cn1c(=S)c2[nH]c(SCCCC(=O)c3ccc(F)cc3)nc2n(C)c1=O]

TPSF/97998

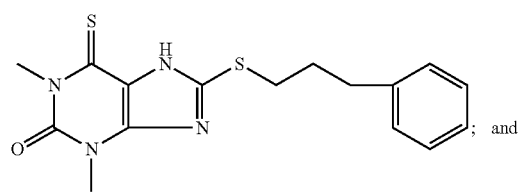

99676

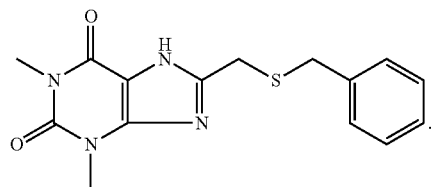

TPBM/95910

In an embodiment, the compound has a structural formula of compound TPSF/97998,

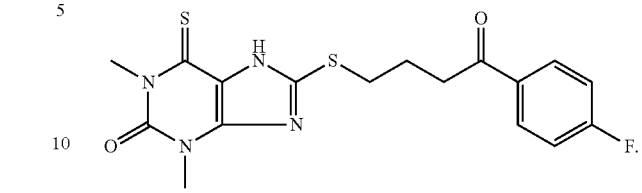

In an embodiment, the invention provides a method of inhibiting growth of a cancer cell comprising contacting said cell with an effective amount of a compound having formula FX1:

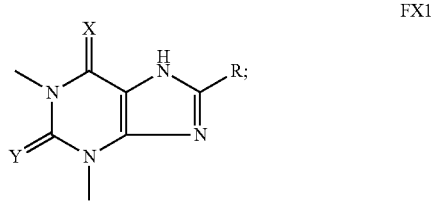

FX1 wherein X and Y independently can be oxygen or sulfur; R can be A, B, C, or D; wherein A is alkyl; B is thioalkyl; C is arylalkyl, and D is cycloalkyl; and wherein each component A, B, C, or D independently is optionally substituted.

In an embodiment, the compound is selected from the group consisting of compounds having formulas corresponding to TPSF/97998, 99676, TPEP/74361, and TPBM/95910:

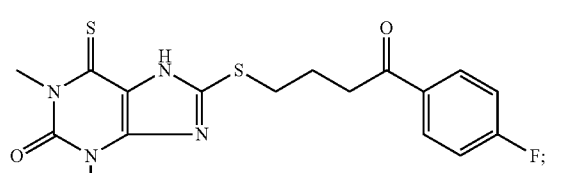

TPSF/97998

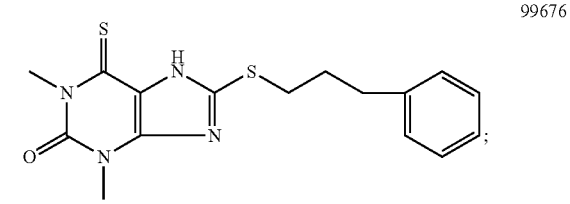 [SMILES: Cn1c(=S)c2[nH]c(SCCCc3ccccc3)nc2n(C)c1=O]

99676

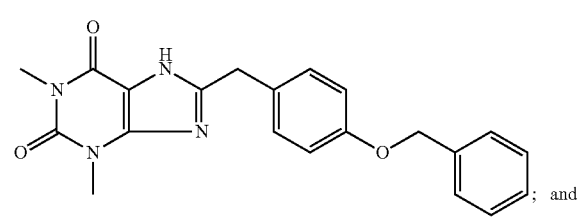

TPEP/74361

; and

TPBM/95910

[Structure of TPBM/95910]

In an embodiment, the invention provides a method of treating cancer comprising administering to a patient in need thereof an effective amount of a compound having formula FX2 or a pharmaceutical formulation thereof:

FX2

[Structure of FX2]

wherein X or Y each independently is S, O, or Se;
R₁ or R₂ each independently is H or C$_{1-6}$ alkyl;
R₃ is —S—CH₂, —O—CH₂—, —CH₂—S, or —CH₂—O—;
R₄ is —C=O, —NH—C=O, —CH₂—, or null;
R₅ is F, Cl, Br, I, At, H, or other group with electronegativity from 1.5 to 4.0; and
n is 1 to 6.

In an embodiment, the cancer is human breast cancer. In an embodiment, the cancer is a resistant cancer. In an embodiment, the resistant cancer has resistance to a chemotherapeutic agent selected from the group consisting of tamoxifen, 4-hydroxytamoxifen (OHT); a selective estrogen receptor modulator, and an aromatase inhibitor. In an embodiment, the cancer is a resistant breast cancer.

In an embodiment, the compound has a structural formula selected from the group consisting of compounds having formulas corresponding to TPSF/97998, 99676, and TPBM/95910. In an embodiment, the compound has a structural formula of compound TPSF/97998.

In an embodiment, the invention provides a method of treating cancer comprising administering to a patient in need thereof an effective amount of a compound having formula FX1 or a pharmaceutical formulation thereof:

FX1

[Structure of FX1]

wherein X and Y independently can be oxygen or sulfur; R can be A, B, C, or D; wherein A is alkyl; B is thioalkyl; C is arylalkyl, and D is cycloalkyl; and wherein each component A, B, C, or D independently is optionally substituted.

In an embodiment, the cancer is human breast cancer. In an embodiment, the cancer is a resistant cancer. In an embodiment, the compound is selected from the group consisting of compounds having formulas corresponding to TPSF/97998, 99676, TPEP/74361, and TPBM/95910. In an embodiment, the compound has a structural formula of compound TPSF/97998.

In embodiments, the invention provides compositions and methods relating to one or more compounds having the structural formula FX2:

FX2

[Structure of FX2]

wherein X or Y each independently is S, O, or Se;
R₁ or R₂ each independently is H or C$_{1-6}$ alkyl;
R₃ is —S—CH₂, —O—CH₂—, —CH₂—S, or —CH₂—O—;
R₄ is —C=O or —NH—C=O;
R₅ is F, Cl, Br, I, At, or other group with electronegativity from 1.5 to 4.0; and
n is 1 to 6.

In embodiments of compounds of formula FX2, an alkyl moiety independently may be optionally substituted by 1 to 5 substituents wherein substituents are independently selected from a group consisting of hydroxy, alkoxy, cyano, ethynyl, alkoxycarbonyl, aryl, acyl or heterocycle. In embodiments, an alkyl group which may be substituted includes the compound component between R₃ and R₄.

In further embodiments of compounds of formula FX2, R₄ is alkyl and independently R₅ is H. In embodiments of FX2, R₄ is absent and the molecule is connected directly via other components. In a particular embodiment, a compound has a structural formula corresponding to NSC 99676.

99676

[Structure of 99676]

In an embodiment, the invention provides a compound and methods relating to a compound having a structural formula corresponding to TPSF/NSC 97998:

TPSF/97998

[Structure of TPSF/97998]

In an embodiment, the invention provides a compound and methods relating to a compound of formula FX2 wherein said compound has formula 97998.

In an embodiment, the invention provides a method of treating cancer comprising administering to a patient in need thereof an effective amount of a composition of the invention, including for example a compound of formula FX1:

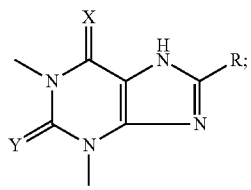

FX1 wherein X and Y independently can be oxygen or sulfur; R can be A, B, C, or D; wherein A is alkyl; B is thioalkyl; C is arylalkyl, and D is cycloalkyl; and wherein each component A, B, C, or D is optionally substituted.

In an embodiment, the invention provides a method of modifying at least one of growth, viability, or replication of a cell comprising contacting said cell with an effective amount of a composition of the invention, including for example a compound of formula FX1.

In an embodiment, said cell is a eukaryotic cell. In an embodiment, said cell is a mammalian cell. In an embodiment, said cell is ex vivo or in vitro. In an embodiment, said cell is in a human patient. In an embodiment, said cell is in a mammalian patient. In an embodiment, said cell is a cancer cell.

In an embodiment, the invention provides a method of inhibiting the activity of a nuclear receptor comprising contacting said nuclear receptor with a composition of the invention. In an embodiment, the invention provides a method of inhibiting the activity of a steroid receptor comprising contacting said steroid receptor with a composition of the invention.

In an embodiment, the invention provides a method of inhibiting the ability of an estrogen receptor alpha molecule, or complex with said molecule, to interact with an estrogen response element and/or to regulate the expression of a gene, comprising contacting said molecule or complex with a composition of the invention.

In embodiments the invention provides compositions and methods for modifying growth of cancer cells which are otherwise resistant to at least one chemotherapeutic agent, chemotherapy, or other cancer therapy. In embodiments the cancer cells are tamoxifen-resistant. In embodiments the cells are breast cancer cells which are tamoxifen-resistant.

In an embodiment, the invention provides a method wherein the composition is a compound of the invention, pharmaceutically acceptable salt or other derivative thereof, and/or pharmaceutical formulation thereof.

In an embodiment, the invention provides the use of a composition of the invention in the making of a medicament in the treatment of a nuclear hormone receptor disorder. In an embodiment, said disorder is a steroid hormone disorder, including for example a disorder in connection with at least one of estrogen, progesterone, and androgen. In an embodiment, the disorder is cancer.

In an embodiment, the invention provides a method of identifying a putative modifier, including for example an inhibitor or a stimulator, of a nuclear hormone receptor, comprising contacting said nuclear hormone receptor with said putative modifier in an in vitro assay, including for example a FAMA assay; wherein said putative modifier is a theophylline compound; and measuring an activity or output in said assay; thereby identifying said putative inhibitor.

In an embodiment, the invention provides a method of identifying a putative modifier, including for example an inhibitor or a stimulator of a nuclear hormone receptor, comprising contacting a cell with said putative modifier in a cell-based assay; wherein said putative modifier is a theophylline compound; and measuring an activity or output in said assay; thereby identifying said putative inhibitor.

In an embodiment, the invention provides a method of identifying as described herein wherein said putative modifier is an 8-substituted theophylline compound.

In an embodiment, the invention provides a method as described herein wherein said composition is capable of inhibiting an interaction between a nuclear hormone receptor, including a steroid hormone receptor, and a receptor response element or the like for said nuclear hormone receptor. In an embodiment, said composition comprises a theophylline compound, including a substituted theophylline and preferably an 8-substituted theophylline.

In an embodiment, the invention provides a method as described herein, wherein said composition is capable of inhibiting the ability of a nuclear hormone receptor, including a steroid hormone receptor from activating or repressing the expression of a cellular gene. In an embodiment, the invention provides a method as described herein, wherein said composition is capable of inhibiting the ability of at least one of an estrogen receptor, a progesterone receptor, and an androgen receptor bound to a hormone from stimulating the growth of a cancer cell.

In an embodiment, the invention provides compounds of the formula FX1:

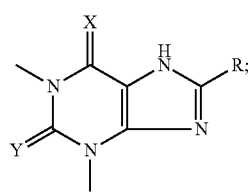

FX1 wherein X and Y independently can be oxygen or sulfur; R can be A, B, or C; wherein A is alkyl; B is thioalkyl; and C is arylalkyl; and wherein each of A, B, or C can be substituted; for example, an alkyl substituent A can itself be substituted, and so forth including as described herein and as would be understood in the art. Moreover, in the case of substituent C, the aryl component of the arylalkyl moiety can be multicyclic, such as with fused rings; the aryl and alkyl components can be independently substituted. Similarly, in the case of substituent B, a thioalkyl component can be further substituted. For example, a thoialkyl component B may be alkylthioalkyl or arylalkylthioalkyl.

In an embodiment, R can be D, wherein D is cycloalkyl or bicycloalkyl; and wherein such cycloalkyl or bicycloalkyl component is optionally further substituted.

In a particular embodiment, a compound of FX1 is the compound designated 14147, 74358, 74361, 95910, or 101794. In a particular embodiment, a compound of FX1 is the compound designated 95869, 95899, or 101807.

In an embodiment, a composition of the invention is isolated or purified.

In an embodiment, the invention provides a pharmaceutical formulation comprising a composition of the invention. In an embodiment, the invention provides a pharmaceutical formulation of a compound described herein. In an embodiment, the invention provides a method of synthesizing a composition of the invention or a pharmaceutical formulation thereof. In an embodiment, a pharmaceutical formulation comprises one or more excipients, carriers, and/or other components as would be understood in the art. Preferably, the components meet the standards of the National Formulary ("NF"), United States Pharmacopoeia ("USP"), or Handbook of Pharmaceutical Manufacturing Formulations. In an embodiment, an effective amount of a composition of the invention can be a therapeutically effective amount.

Variations on compositions including salts and ester forms of compounds: Compounds of this invention and compounds useful in the methods of this invention include those of the formula (s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds including diphosphonate compounds of the formulas herein. In embodiments, salts and esters of the compounds of the formulas herein can include those which have the same therapeutic or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for treating a medical condition comprising administering to a subject in need thereof, a therapeutically effective amount of a composition of the invention. In an embodiment, the medical condition is cancer. In an embodiment, the medical condition is breast cancer, prostate cancer, uterine cancer, ovarian cancer, or multiple sclerosis.

In an embodiment, the invention provides a medicament which comprises a therapeutically effective amount of one or more compositions of the invention. In an embodiment, the invention provides a method for making a medicament for treatment of a condition described herein.

Compounds of the invention can have prodrug forms. Prodrugs of the compounds of the invention are useful in embodiments including compositions and methods. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

In embodiments, the invention contemplates pharmaceutically active compounds either chemically synthesized or formed by in vivo biotransformation to compounds of formulae described herein. In embodiments, the invention provides compounds of formulae described herein excepting particular compounds of the prior art, namely NSC compounds as described herein. For example, the compounds excluded would consist of TPSF/97998, 99676, TPBM 95910, and so on as set forth herein and according to the NSC knowledge base as of the filing date as accorded herewith.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

BRIEF DESCRIPTION OF THE FIGURES

FIG. 18 illustrates the activity of TPSF in resistant human breast cancer cells. It was determined that TPSF inhibits E2 and OHT-induced gene expression in a tamoxifen-stimulated cell line. MCF7ERαHA cells were maintained in 6×CD-FBS treated for 24 h with 0.5 µg/ml Dox to induce ERα and 100 pM $E_2$ (FIG. 18A) or 500 pM OHT (FIG. 18B) and TPSF as indicated. PI-9 mRNA levels were measured by qRT-PCR as described in Materials and Methods. PI-9 mRNA in control MCF7ERαHA cells not treated with Dox, E2 or OHT was set equal to 1. The high level of ERα in Dox-treated cells results in some ligand-independent transactivation of PI-9. Data are the average of 2 experiments for E2 and 3 experiments±SEM for OHT.

FIG. 19 illustrates that TPSF, but not OHT, is capable of inhibiting $E_2$-ERα-dependent growth of tamoxifen-resistant breast cancer cells as measured in MCF7ERαHA cells. MCF7ERαHA cells were maintained for 4 days in 6× stripped CD-FBS, seeded into 12 well plates containing or lacking Dox (0.5 µg/ml), $E_2$ (1 pM) OHT (5 µM) and TPSF (5 µM), grown for 4 days and assayed using MTS with a standard curve for cell number. Cells in ethanol and DMSO vehicle alone were set to 100%. Data represents the average of 3 experiments±SEM. The difference between the cells incubated with TPSF+$E_2$+Dox compared to the cells in Dox, and $E_2$ and to the cells in Dox, $E_2$ and OHT was significant (P<0.05 using Student's two-tailed T test).

FIG. 20 illustrates further activity of TPSF in the inhibition of tamoxifen-resistant human breast cancer cells. The effects of TPSF on the $E_2$-ERα-dependent growth of tamoxifen-resistant BT474 and ZR-75 cells were assessed. TPSF demonstrated significant inhibition of the growth of resistant breast cancer cells. The cells were maintained in medium containing 10% CD-FBS (ZR-75) or 10% CD-CS (BT474) containing or lacking 100 pM E2 and the indicated concentrations of TPSF. Viable cells were measured by comparison to a standard curve of cell number versus absorbance using the MTS assay. Data represents the average of at least 4 wells. $IC_{50}$ values for TPSF inhibition of cell growth were calculated by curve-fitting using Sigma Plot.

DETAILED DESCRIPTION OF THE INVENTION

Figure 1:
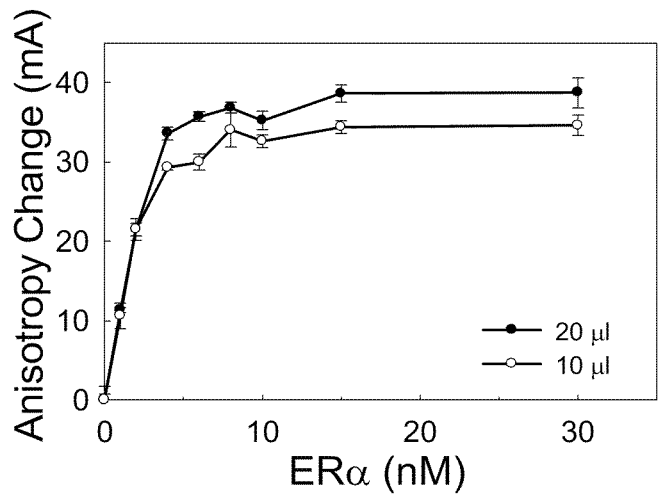
FIG. 1 illustrates results of fluorescence anisotropy microplate assay (FAMA) data, measuring binding to the Estrogen Response Element. FAMA was carried out in 384-well black wall microplates using either the standard 20 μl volume (filled circles), or the 10 μl volume used in the final HTS screen (open circles). Data represents the average increase in anisotropy observed after $E_2$-ERα binding to the flcERE. Data represent the mean±SEM for 4 separate experiments.

The following abbreviations are applicable. The abbreviations used are: ERα, estrogen receptor α (alpha); $E_2$, 17β-estradiol; flcERE, fluorescein-labeled consensus estrogen response element; FAMA, fluorescence anisotropy microplate assay; TPBM, theophylline, 8-[(benzylthio)methyl]-(7CI,8CI) also known as 8-benzylsulfanylmethyl-1,3-dimethyl-3,7-dihydro-purine-2,6-dione; OHT, 4-hydroxytamoxifen; SERM, selective estrogen receptor modulator; EtOH, ethanol; DMSO, dimethyl sulfoxide; PR, progesterone receptor; AR, androgen receptor; GR, glucocorticoid receptor; ARE, androgen response element; HRE, hormone response element; GRE/PRE, glucocorticoid/progesterone response element; $IC_{50}$, Inhibitor concentration for 50% inhibition; Dox, Doxycycline.

In general the terms and phrases used herein have their art-recognized meaning, which can be found by reference to standard texts, journal references and contexts known to those skilled in the art. Further description may be provided herein regarding certain information for definitions of relevant terms.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl group and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds;

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The invention may be further understood by the following non-limiting examples.

Example 1

Inhibition of Estrogen Receptor Alpha Binding to Estrogen Response Elements

Estrogen receptor α (ERα) is a transcription factor that plays an important role in several human cancers. Most current ERα antagonists bind in the receptor ligand binding pocket and compete for binding with estrogenic ligands. Instead of the traditional approach of targeting estrogen binding to ER, we describe a strategy using a high throughput fluorescence anisotropy microplate assay to identify small molecule inhibitors of ERα binding to consensus estrogen response element (cERE) DNA. We identified small molecule inhibitors of ERα binding to the fluorescein-labeled (fl)cERE and evaluated their specificity, potency and efficacy. One small molecule, theophylline, 8-[(benzylthio)methyl]-(7CI, 8CI) (TPBM), inhibited ERα binding to the flcERE ($IC_{50}$ value of about 3 μM) and inhibited ERα-mediated transcription of a stably transfected ERE-containing reporter gene. Inhibition by TPBM was ER specific since progesterone and glucocorticoid receptor transcriptional activity were not significantly inhibited. In tamoxifen-resistant breast cancer cells that overexpress ERα, TPBM inhibited 17β-estradiol ($E_2$)-ERα ($IC_{50}$ 9 μM) and 4-hydroxytamoxifen-ERα-mediated gene transcription. TPBM inhibited $E_2$-dependent growth of ERα positive cancer cells ($IC_{50}$ 5 μM). TPBM is not toxic to cells and had no effect on estrogen-independent cell growth. TPBM acts outside of ERs ligand-binding pocket, does not act by chelating the zinc in ERs zinc fingers and differs from known ERα inhibitors. Using a simple high throughput screen for inhibitors of ERα binding to the cERE, a small molecule inhibitor has been identified that selectively inhibits ERα mediated gene expression and estrogen dependent growth of cancer cells.

To inhibit ERα binding to the ERE, we developed and implemented an HTS fluorescence anisotropy microplate assay (FAMA) (27). We have used FAMA to demonstrate active displacement in the binding of full-length SRC1 to ERE-ER complexes (28). To use the FAMA as an HTS assay, a fluorescein-labeled consensus ERE (flcERE) is synthesized (28,29). When polarized light excites the flcERE, the relatively small flcERE usually undergoes rotational diffusion more rapidly than the time required for light emission. Therefore, the position of the flcERE at the time of light emission is largely randomized, resulting in depolarization of most of the emitted light. When full-length ERα binds to the flcERE, the larger size of the flcERE:ERα complex causes slower rotation, increasing the likelihood that the flcERE:ERα complex will be in the same plane at the time of light emission as it was at the time of excitation. Therefore, the emitted light remains highly polarized. A receptor-DNA interaction increases fluorescence polarization (FP) and fluorescence anisotropy (FA). Although FA assays based on using a labeled DNA binding site for the protein of interest represent an attractive approach, a study using this in vitro strategy to identify small molecule inhibitors of the b-zip DNA binding transcription factors failed to identify specific inhibitors that function in cells (30).

Here we used FAMA to conduct HTS and identified small molecules, including a particular small molecule, theophylline, 8-[(benzylthio)methyl]-(7CI,8CI) (TPBM; an 8-alkyl-thio-thiated theophylline) (31,32), that can specifically inhibit $E_2$-induced, ERα-mediated, gene expression in intact cells, without significantly inhibiting PR and GR mediated gene expression. TPBM also inhibits $E_2$ and 4-hydroxytamoxifen (OHT, the active metabolite of tamoxifen) induction of an endogenous gene in tamoxifen-resistant breast cancer cells. TPBM is not toxic to ERα negative cells and exhibits dose-dependent inhibition of the estrogen-dependent growth of ERα positive cancer cells. Our data show that an in vitro assay, using a protein-free consensus ERE and purified ERα, can identify small molecule inhibitors that block ER-mediated gene expression and estrogen-dependent growth of cancer cells. Thus in part we have contributed a method of screening for certain molecules including theophylline molecules.

Experimental Procedures

Proteins—

Full-length FLAG-tagged human ERα was expressed and purified as described previously (27). Human FLAG-PR-B (33) and full-length, wild-type human FLAG-AR were purified as described (34).

Oligonucleotides—

A 30-bp oligonucleotide containing the cERE was synthesized with fluorescein (6-FAM) at its 5' end using phosphoramidite chemistry and PolyPak II— (Glen Research Corp, Sterling, Va., USA) purified by the Biotechnology Center (University of Illinois, Urbana Ill.). This flcERE was used in our earlier work describing FAMA (27,28). The sequence of the fluorescein-labeled sense strand, with the cERE half sites underlined, is:

```
                                          (SEQ ID NO: 1)
5'-fl-CTAGATTA CAGGTCACAGTGACCTTACTCA-3'.

The flcARE is
                                          (SEQ ID NO: 2)
5'-fl-CTAGATTACGGTACATGATG TTCTTACTCA-3'.

The flcPRE is
                                          (SEQ ID NO: 3)
5'-fl-CTAGAT TACAGAACAATCTGTTCTTACTCA-3'.
```

The flcARE and flcPRE were synthesized and characterized as described for flcERE. To remove traces of free fluorescein present in some oligonucleotides (29), they were passed over a centri-sep column (usually used to remove free fluorescent dyes in DNA sequencing) following the supplier's directions (Princeton Separation, Princeton, N.J.). Oligonucleotides were prepared at 10 μM and 50-100 μl was loaded onto each column. To calculate oligonucleotide concentration, $A_{260}$ values were measured. The method of Ozers et al. (35) was used to determine the degree of fluorescein incorporation (FI), which was ~60% for the flcERE and slightly lower for the flcARE and flcPRE. After column purification, the double-stranded probes were produced by annealing the fluorescein-labeled sense strand with an equimolar amount (both at 1 μM) of the unlabeled antisense strand oligonucleotide in TE buffer (10 mM, Tris pH 7.5, 1 mM EDTA) containing 100 mM NaCl at 100° C. for 5 min., followed by slow cooling in a water bath to form double-stranded probe.

High Throughput Screening Using FAMA—

Previous microplate-based fluorescence polarization/anisotropy assays used 20-30 µl volumes (19,27,30). To minimize protein use and to identify the appropriate concentrations of ERα to use in HTS, we carried out ERα binding studies in 10 µl and 20 µl. As we recently reported for RNA binding proteins (29), the use of small volumes results in only a slight decline in FA signal with no change in $K_d$ or loss of reproducibility (FIG. 1). The only modification required for the 10 µl assays was brief centrifugation of the 384-well plates to ensure that the sample volume was uniformly distributed across the bottom of the wells.

Two libraries of small molecules were screened. A library developed at the University of Illinois by K. Putt and P. Hergenrother contained ~9,700 small molecules (22,36,37) and the National Cancer Institute (NCI) Diversity Set contained 1,990 small molecules.

Prior to screening, the 10 mM library stocks were diluted to produce replica libraries in 384-well plates containing each small molecule at 0.25 mM (in DMSO). In our initial studies we were concerned that forming the flcERE-ERα complex first and then adding the candidate small molecule inhibitors would miss small molecules that bind at the interface. We therefore screened using the "sequential" method in which the candidate small molecules were first incubated with ERα and followed by addition of the flcERE. The assay for binding of ERα to the flcERE is a modification of our earlier assay (27). Assays were carried out at room temperature in black wall 384-well microplates (Greiner/Bio-One) in a total volume of 10 µl in buffer containing 20 mM Tris pH 7.5, 10% glycerol, 0.2 mM EDTA, 2 mM DTT, 100 mM KCl, 0.5 ng/µl poly dI:dC, 250 µg/µl bovine serum albumin and 100 nM 17β-estradiol ($E_2$). For high throughput screening, a master mix without ERα and probe was prepared at 4° C. The master mix was divided into 2 parts. ERα was added to one part to 5 nM in the final assays. 7 µl of the ERα-containing mix was then dispensed into each well of a 384-well plate on ice. 100 nl of the compounds being tested was then added using a pin-transporter (V & P Scientific, Inc, CA) to a final concentration of 2.5 µM. The samples were mixed using the pin-transporter and sedimented by centrifugation for 2 min. at 4° C. and incubated on ice for 10 min. The flcERE probe was added to the other aliquot of the mix to 1 nM. 3 µl of the mix containing the flcERE probe was added to each well containing ERα and the test compound. The samples were mixed using the pin-transporter, the plates were briefly centrifuged and incubated at room temperature for 10 min. and fluorescence anisotropy (FA) was measured using a BMG PheraStar (BMG Labtech) microplate reader (module: 485 520) with excitation at 485λ and emission at 520λ. To identify small molecules that were highly fluorescent, or quench fluorescence, fluorescence intensity was also measured.

Although there is no universally accepted standard of what change in signal constitutes a "hit" suitable for further evaluation, some researchers consider that any small molecule that results in a change of more than 3 standard deviations from the mean is appropriate for further study. Under the conditions of the HTS the average change in anisotropy over the entire 384-well plate was 31.6±2.7 S.D. The S.D. is 8.5% and 3×S.D. is ~25%. We therefore carried out further analysis of small molecules that, when present at 2.5 µM, altered the average change in anisotropy for binding of ERα to the flcERE by at least 25%. Re-screening the same plates demonstrated that the screen was reproducible. 76% of the primary hits scored as hits on re-screening a set of the initial plates.

Dose response curves for selected compounds were carried out as described for the HTS screen except that each well contained the indicated concentration of test compound. PR assays were carried out in the same buffer used for ERα assays and contained 1 nM flcPRE and 11 nM PR-B and 100 nM progesterone. The buffer used for AR was similar but also contained 5 µM ZnCl, 5 mM NaF, 0.6 µM CHAPS and 100 nM dihydrotestosterone. AR assays contained 1 nM flcARE and 50 nM full-length wild-type AR. The concentrations of ERα, PR and AR chosen for use produce 70-80% of maximum binding.

Reporter Gene Assays—

The T47D-KBluc cells stably express an $(ERE)_3$-luciferase reporter gene (38). Cells were maintained in phenol red-free RPMI 1640 with 2 mM L-glutamine, 1.5 g/l sodium bicarbonate, 4.5 g/l glucose, 10 mM Hepes, pH 7.5, 1 mM sodium pyruvate, 10% FBS (Atlanta Biological, Atlanta, Ga.) and antibiotics. Four days before $E_2$ induction, the cells were switched to the above medium, with 10% 2× charcoal-dextran-treated calf serum instead of FBS. 200,000 cells/well were transferred to each well of a 24-well plate. After 24 h the indicated concentrations of the test compounds were added in DMSO and $E_2$ was added to 20 pM. After 24 h cells were washed once in PBS, and 150 µl 1× Passive Lysis Buffer (Promega, Madison Wis.) was used to lyse the cells. Luciferase activity was determined using firefly luciferase reagents from Promega (Madison, Wis.). T47D cells stably transfected to express GR and a mouse mammary tumor virus luciferase reporter that responds to liganded GR and PR were maintained and assayed in medium containing 5 nM progesterone for PR assays, or 2.5 nM dexamethsaone for GR assays, essentially as described (39).

Evaluating Endogenous Gene Expression in Tamoxifen-Resistant Breast Cancer Cells—

A model for tamoxifen-resistant breast cancers that overexpress ERα is MCF7ERαHA cells, which is a tetracycline-inducible MCF-7 model in which doxycycline (Dox) induces overexpression of ERα (40,41). In contrast to MCF-7 cells, in these cells Tam and OHT are potent agonists (2,42) and OHT, which stabilizes ERα, induced proteinase inhibitor 9 (PI-9) mRNA and protein more effectively than $E_2$ (2,43). MCF7ERαHA cells were maintained in 10% 6XCD-treated FBS (40,41). All cells were in 0.1% DMSO vehicle and contained the indicated concentrations of TPBM added at the same time as the $E_2$ or OHT. To induce PI-9 mRNA, the cells were treated with 0.5 µg/ml doxycycline to induce ERα and ethanol vehicle, 100 pM $E_2$ or 500 pM OHT for 24 h, mRNA was extracted and PI-9 mRNA levels were determined by quantitative RT-PCR as described (2).

Cell Growth and Toxicity Assays—

ERα positive BG-1 ovarian cancer cells (44) were provided by Prof. K. Korach. ERα negative MDA-MB-231 human breast cancer cell lines were provided by Prof. A. Nardulli. The cells are maintained in phenol red-free MEM medium with 5% calf serum and antibiotics. 4 days before hormone induction, cells are switched to phenol red-free MEM medium containing 5% 2XCD-treated calf serum for BG-1 cells. For BG-1 cell growth assays, 250 cells in 100 µl of phenol-red-free medium were added to wells of a 96-well plate. After 24 h, the indicated concentrations of the test compounds and 10 pM $E_2$ or ethanol vehicle were added to each well. Compounds in DMSO were diluted in medium so that the DMSO concentration was not greater than 0.5%. Cell viability assays were carried out 5-6 days later using Promega CellTiter 96®Aqueous One Solution Cell Proliferation Assay (Promega, Wis.).

ERα negative MDA-MB-231 human breast cancer cells were used to test for generalized toxicity of the test compounds. To parallel the reporter gene assays in stably transfected T47D breast cancer cells, 5,000 MDA-MB-231 cells per well were plated in a 96 well plate. The cells were maintained in the medium described above for the T47D cells. One day after plating, the same concentration of test compound used in the reporter gene assay (up to 30 µM) was added. After 24 h the MTS assay was carried out as described above. A more stringent toxicity assay parallels the assay for inhibition of estrogen-dependent growth of BG-1 cells. 250 MDA-MB-231 cells were plated per well and maintained and assayed as described for the BG-1 cells. Several compounds without detectable toxicity in the 24-h assay inhibited MDA-MB-231 cell growth in the 5-6 day assay.

Western Blots—

Western blots were performed as described (43) with minor modifications. ERα was detected using a 1:2,000 dilution of ERα antibody ER6F11 (Bio Care Medical, Concord, Calif.). The blot was stripped for 15 min. prior to reprobing with a 1:10,000 dilution of actin antibody.

Results

The High Throughput Screen for Inhibitors of ERα—

Figure 2:
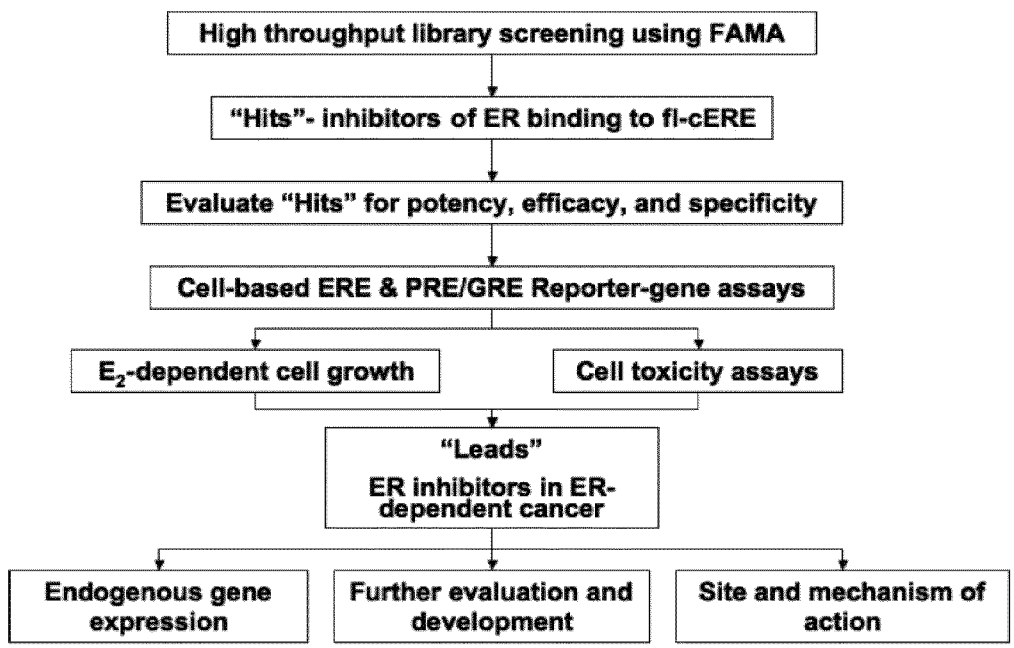
FIG. 2. Scheme for identification and characterization of small molecule inhibitors of ERα action in ER-dependent cancer cells. We identified ERα antagonists with approaches that included the following assays. (i) In vitro FAMA assays using purified proteins and DNA to carry out the HTS screen and to further characterize the verified hits for potency, efficacy and specificity. (ii) Cell-based gene expression assays to determine potency and efficacy and to evaluate specificity using assays for PR and GR-regulated gene expression. (iii) Cell growth assays for evaluating ability of the final candidates to block estrogen-dependent growth of cancer cells and for their generalized toxicity in ERα negative cancer cells. (iv) Testing inhibitor potency and efficacy against an endogenous gene in Tam-resistant breast cancer cells. (v) Studies to test sites of ERα inhibitor action.

Development of the µl primary screen (FIG. 1) is described herein (see Experimental Procedures). The sequence of assays used to identify the lead inhibitor of ERα action in ER-dependent cancer cells is summarized in the flow chart in FIG. 2. In the initial high throughput screen, FAMA was used to assay binding of purified hERα to the flcERE in 384-well microplates. The validated hits were evaluated using FAMA for potency, efficacy and specificity. Certain compounds were further tested in breast cancer cell lines stably transfected with reporter genes, in cell-based assays for toxicity, and for their ability to block estrogen dependent cancer cell growth. A particular lead compound, TPBM, was then tested for its ability to inhibit $E_2$ and OHT induction of the endogenous PI-9 gene in tamoxifen-resistant MCF7ERαHA cells. To begin to evaluate its site of action, we showed that TPBM does not bind in the ligand binding pocket of ERα and that zinc does not block its inhibitory effect, indicating it is not an electrophile acting by chelating the zinc in the zinc fingers of ER.

Out of about 12,000 small molecules initially screened at 2.5 µM, 262 reduced the anisotropy of the ERα-flcERE complex by >25% (see Experimental Procedures). After rescreening and eliminating compounds that no longer reduced the anisotropy change by >25%, displayed intrinsic fluorescence, were quenchers, or reduced the signal of the free flcERE probe, 56 structurally diverse compounds were selected for further testing. Most of the small molecules excluded from further analysis either displayed intrinsic fluorescence, or reduced the signal by a little over 25% in the initial assay and slightly less than 25% on re-testing.

Analysis of Hits for ERα Specificity, Potency and Efficacy—

Detailed potency and efficacy studies established $IC_{50}$ values required to block ERα binding to flcERE. Specificity was evaluated in dose-response studies by quantitative FAMA using purified full-length human PR binding to a fluorescein-labeled progesterone/glucocorticoid response element (fl-PRE) and full-length human androgen receptor (AR) binding to a fluorescein-labeled androgen response element (flARE). $IC_{50}$ values for inhibition of HRE binding by ERα, PR and AR were determined for each of 56 small molecules identified in the primary screen and subsequent verification assays (Table 1). Most of the compounds inhibited more than one steroid receptor.

Table 1 Indicates $IC_{50}$ Values for Small Molecule Inhibitors of Binding of Steroid Receptors to their HREs.

Figure 3A:
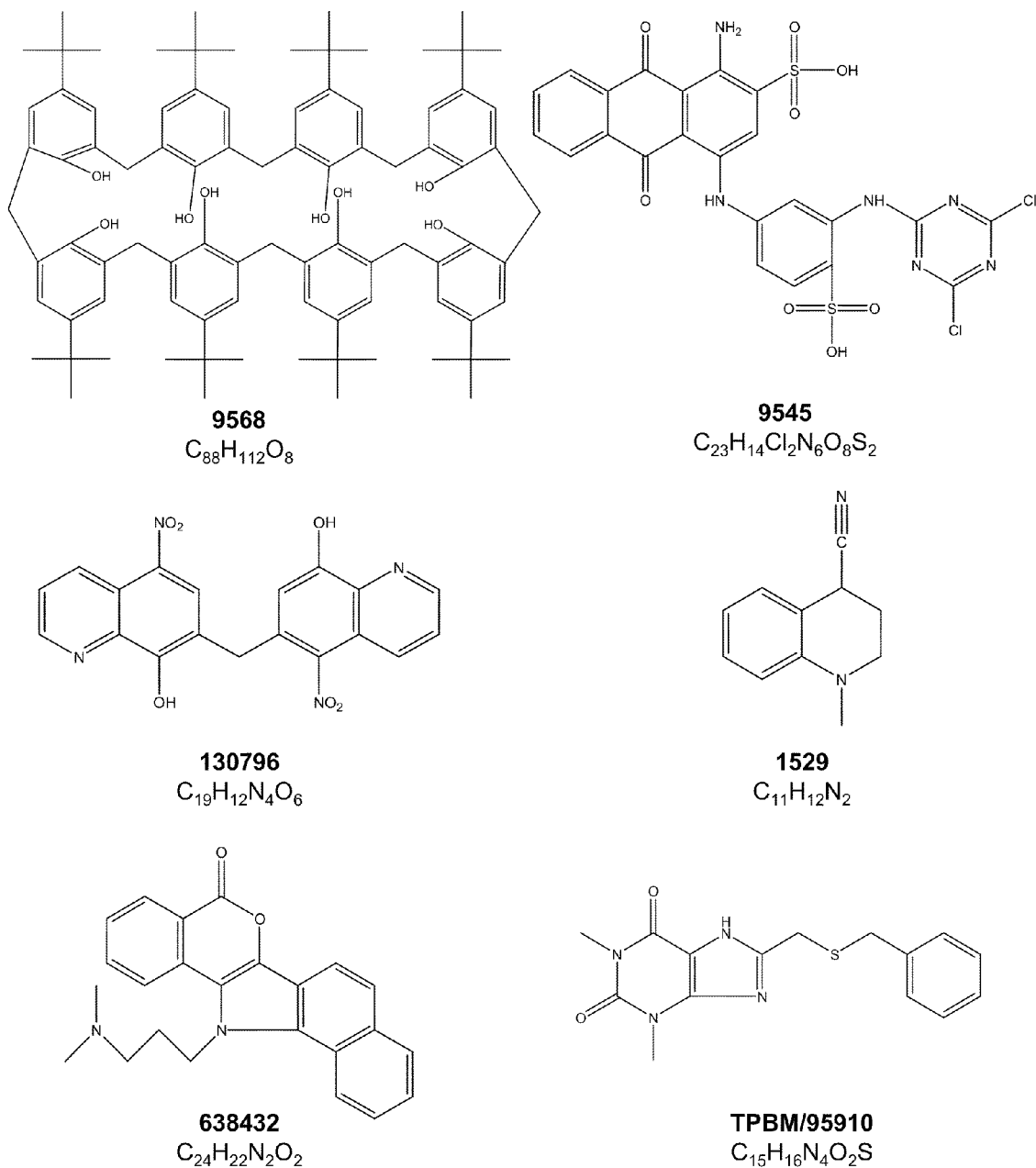
FIG. 3. Dose-response curves for inhibition of ERα, PR and AR binding to their HREs. (A) The structures of six compounds whose binding curves are shown in panel (B), including compounds 9568 ($C_{88}H_{112}O_8$), 9545 ($C_{23}H_{14}Cl_2N_6O_8S_2$), 130796 ($C_{19}H_{12}N_4O_6$), 1529 ($C_{11}H_{12}N_2$), 638432 ($C_{24}H_{22}N_2O_2$), and TPBM/95910 ($C_{15}H_{16}N_4O_2S$). (B) Dose-response curves for ERα selective and non-selective inhibitors identified in the primary HTS screen. The indicated concentrations of each small molecule were incubated with ERα (filled circles), AR (open triangles) and PR (filled squares) using the sequential method described in Experimental Procedures. The anisotropy change on binding of each receptor to its respective response element was set equal to 100%. These anisotropy changes were: ERα ~35 mA units, PR ~90 mA units and AR ~60 mA units. Since AR and PR are larger than ER, their binding to their HREs results in larger anisotropy changes. The data for compound TPBM/95910 represents a separate set of experiments from the data used to compile Table 1. The data represent the mean±SEM for 4 separate experiments at each concentration.
Figure 3B:
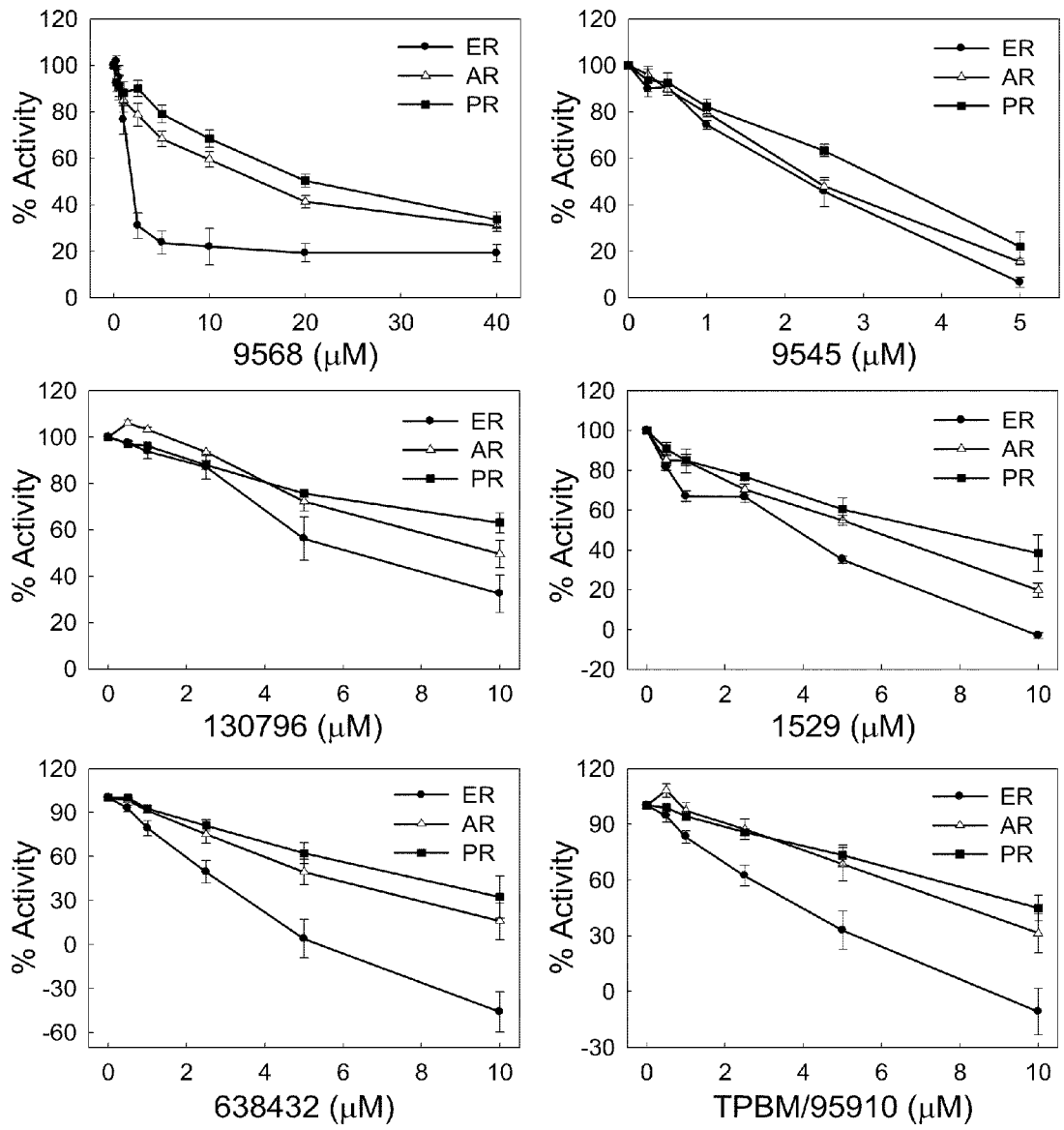

$IC_{50}$s were determined from dose-response curves (see FIG. 3B). For each small molecule binding of the indicated steroid receptor (ERα, AR or PR was determined at 5 concentrations (0.5, 1, 2.5, 5 and 10 µM). The data represents the average of 4 independent sets of samples at each concentration. FAMA for ER, AR and PR was performed using the sequential method as described in Experimental Procedures. The small molecules shown in FIG. 3 are in bold with underlining.

TABLE 1

| Compound | IC50 (micromolar) | | | Compound | IC50 (micromolar) | | |
| --- | --- | --- | --- | --- | --- | --- | --- |
| | ERα | AR | PR | | ERα | AR | PR |
| 92 | 2.5 | 0.5 | 5 | 7473 | 9 | >10 | >10 |
| 340 | >10 | 5.5 | 8 | 7484 | 9.5 | >10 | >10 |
| 1387 | 4.5 | 4.8 | 6.5 | 7487 | 9.5 | >10 | >10 |
| 1445 | 0.6 | 0.7 | 1.2 | 8216 | 9 | >10 | >10 |
| 1529 | 4 | 5.2 | 7.5 | 9064 | >10 | >10 | >10 |
| 1826 | 7 | 8 | 6 | 9503 | 2.6 | >10 | >10 |
| 2067 | 5 | 3 | 10 | 9545 | 0.7 | 3 | 3.8 |
| 2287 | 2.1 | 1.7 | 2.7 | 9548 | 1 | 4 | 5 |
| 2674 | 5.5 | 5.8 | 6.2 | 9568 | 2 | >10 | >10 |
| 3706 | 0.8 | 1 | 1.5 | 9671 | >10 | >10 | >10 |
| 3710 | 2.5 | 5 | 2.9 | 343040 | >10 | >10 | >10 |
| 3713 | 6 | 5.2 | 7 | 7810 | >10 | >10 | >10 |
| 3813 | 2 | 4.8 | 6.5 | 371847 | >10 | >10 | >10 |
| 3879 | 3.7 | 7.5 | 6.5 | 90737 | 10 | >10 | >10 |
| 4456 | 7.5 | >10 | >10 | 95910 | 3 | 7.6 | 9.5 |
| 4695 | 2.5 | 4.8 | 4 | 15596 | 5 | >10 | >10 |
| 4700 | 2 | 2 | 2.7 | 130796 | 6 | 10 | >10 |
| 4792 | >10 | 7.5 | >10 | 360494 | >10 | >>10 | >10 |
| 4864 | 8 | 6.5 | 8.8 | 170008 | 9 | 9 | 10 |
| 5648 | 6.5 | 4.5 | 7.3 | 125908 | 3.8 | >10 | >10 |
| 5649 | 9 | 6.7 | 8.5 | 638432 | 2.5 | 5 | 7.4 |
| 5650 | 8 | 5.5 | 7.5 | 34238 | 1.8 | 10 | >10 |
| 6119 | 9 | 7.4 | 9 | 91767 | 8 | >10 | >10 |
| 6122 | 5.8 | 3.7 | 5.3 | 112257 | 10 | >10 | >10 |
| 6454 | 5.8 | >10 | 10 | 109268 | 8 | 9 | >10 |
| 7107 | 5 | 10 | >10 | 43628 | >10 | >10 | >10 |
| 7122 | 5 | 7.5 | 10 | 306711 | 6.1 | 4 | >10 |
| 7450 | 9.8 | >10 | >10 | 146443 | <0.5 | 0.5 | 0.4 |

Structures (FIG. 3A) and dose-response curves (FIG. 3B) are presented for the 4 compounds subject to the most extensive analysis in cell-based studies (see below) and for two molecules representative of the diverse outcomes we observed. Compound 9568 (FIG. 3A) exhibited high potency and was the most specific ER inhibitor of the approximately 12,0000 molecules tested (FIG. 3B, 9568). However, it is relatively large (M.W. about 1,300) (FIG. 3A, 9568) and had poor bioavailability in cell culture. Compound 9545 is representative of several small molecules that displayed good potency and efficacy but lacked specificity, having similar ability to inhibit binding of ERα, PR and AR to their respective hormone response elements (HREs). Four structurally diverse molecules selected for further testing in cell-based assays exhibited good potency, with preferential inhibition of ERα binding to the flcERE relative to PR and AR binding to their HREs (FIG. 3B, compounds, 130796, 1529, 638432 and TPBM/95910).

Small Molecule Hits Inhibit ER-Mediated Transcription in Intact Cells—

Figure 4:
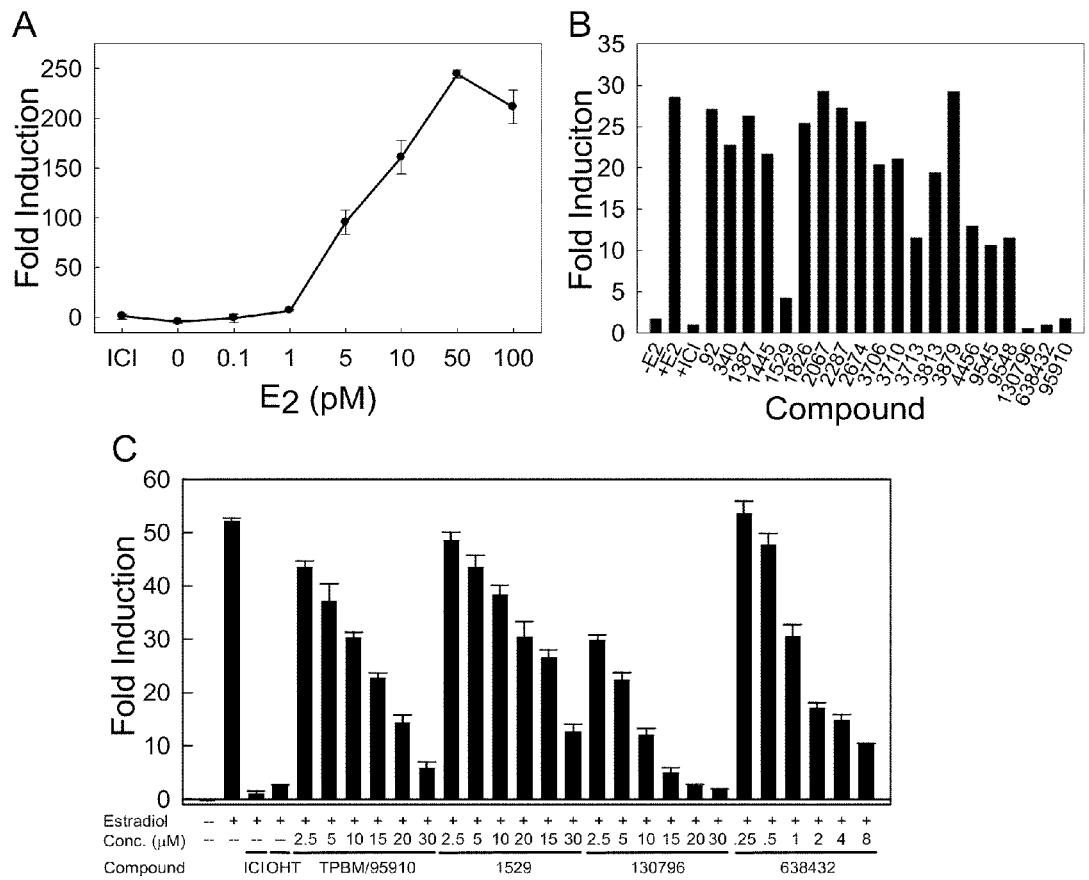
FIG. 4. Effect of small molecules on ER-mediated gene expression in T47DKBluc cells. A $E_2$-dose response curve. The cells were maintained in medium containing either 1 nM ICI 182,780 (to test for traces of estrogens in the medium), or the indicated concentrations of $E_2$ and reporter gene expression was assayed after 24 hours. The data represent the average of 3 independent experiments±SEM. B Inhibition of ERα-mediated gene expression by small molecules that inhibit binding of ERα to the ERE. Small molecules identified in the FAMA HTS screen, verified and further characterized for potency and specificity were tested. Cells were incubated in medium containing 30 μM inhibitor for 30 min, then 20 μM $E_2$ (panel A) was added and the cells were incubated for an additional 24 h. Control experiments demonstrated that the DMSO used to dissolve the small molecules and the ethanol used to dissolve the $E_2$, separately and in combination, did not alter gene expression or reduce cell viability. Data in B represents single experiments. C Dose response curves for small molecules that inhibit ER-mediated gene expression. Assays were as described in panel B. In control experiments the cells were maintained for 24 h in medium containing 20 pM $E_2$, with or without 1 nM of ICI 182,780 or OHT. The indicated concentrations of each small molecule were incubated with the cells and $E_2$-ER-mediated gene expression assayed. The data represent the mean±SEM for 4 separate experiments at each concentration. $IC_{50}$s were obtained by curve-fitting using Sigma plot and had a high $R^2$ value.

The ability of each small molecule to inhibit ER-mediated gene expression in intact cells was tested in the ERα positive T47D-KBluc breast cancer cell line that stably expresses an $(ERE)_3$-luciferase reporter gene (38). An $E_2$ dose-response curve showed that the cells exhibited strong $E_2$-dependent activation of the reporter gene with full induction at 50 nM $E_2$ (FIG. 4A). This is within the concentration range shown to induce PI-9 in MCF-7 cells (2) and several endogenous genes in HeLa cells stably transfected to express ERα (45).

Candidate small molecules were initially tested at 30 μM in the T47D cell assay in medium containing 20 pM $E_2$ for 24 h prior to measuring luciferase activity (FIG. 4B). As expected a 100 fold molar excess of the antagonist ICI 182,780/Faslodex/Fulvestrant blocked activation of the reporter gene (FIG. 4B, +ICI). Small molecules that inhibited expression of the reporter by at least 50% and were not toxic in a short-term 24 hour toxicity test using MDA-MB-231 cells (see Experimental Procedures) were subjected to additional analysis. As shown in FIG. 4C, concentration-dependent inhibition of $E_2$ dependent ERα transactivation was observed with $IC_{50}$ values of 11.5 μM 95910/TPBM, 22 μM 1529, 3.5 μM 130796 and 0.8 μM 638432.

Figure 5:
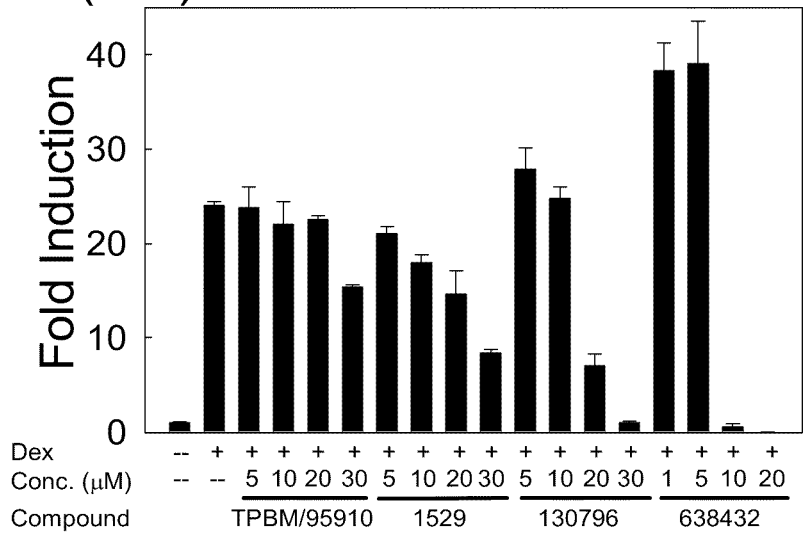
FIG. 5. Effect of ERα inhibitors on GR and PR-mediated gene expression in T47D cells. Assays were performed essentially as described for ER in the legend to FIG. 4. A and B. The indicated concentration of each small molecule and 2.5 nM dexamethasone to assay GR-transactivation (A) or 5 nM progesterone to assay PR transactivation (B) was added to the cells at the same time. After 24 h luciferase activity was measured. The data represent the mean±SEM for 4 separate experiments at each concentration.
Figure 5:
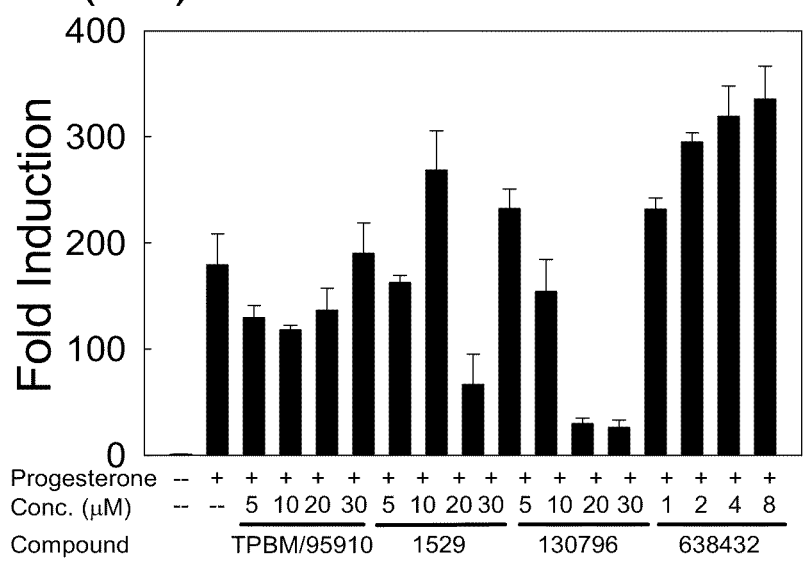

To establish specificity for ERα, we tested the small molecules for inhibition of GR and PR transactivation in T47D cells that express stably transfected GR and contain sufficient endogenous PR-B (but not AR) to activate the stably expressed MMTV-luciferase reporter (39). Using T47D cells for the ERα, GR and PR transactivation experiments minimized effects due to cell context. In preliminary experiments we found that 2.5 nM dexamethasone (Dex) and 5 nM progesterone each elicited ~80% of maximum induction, the same relative level of transactivation used in our studies with $E_2$. These hormone concentrations resulted in transactivation that was specific for the receptor being tested. In dose-response studies, higher concentrations of 638432 and 130796 were required to inhibit GR transactivation than ERα, and TPBM/95910 did not inhibit GR transactivation up to 20 μM, with ~35% inhibition at 30 μM (FIG. 5A). Compound TPBM/95910 did not significantly inhibit PR transactivation. Compounds 1529 and 130796 inhibited PR transactivation between 20-30 μM (FIG. 5B).

Inhibition of the Estrogen-Dependent Growth of Cancer Cells—

Figure 6:
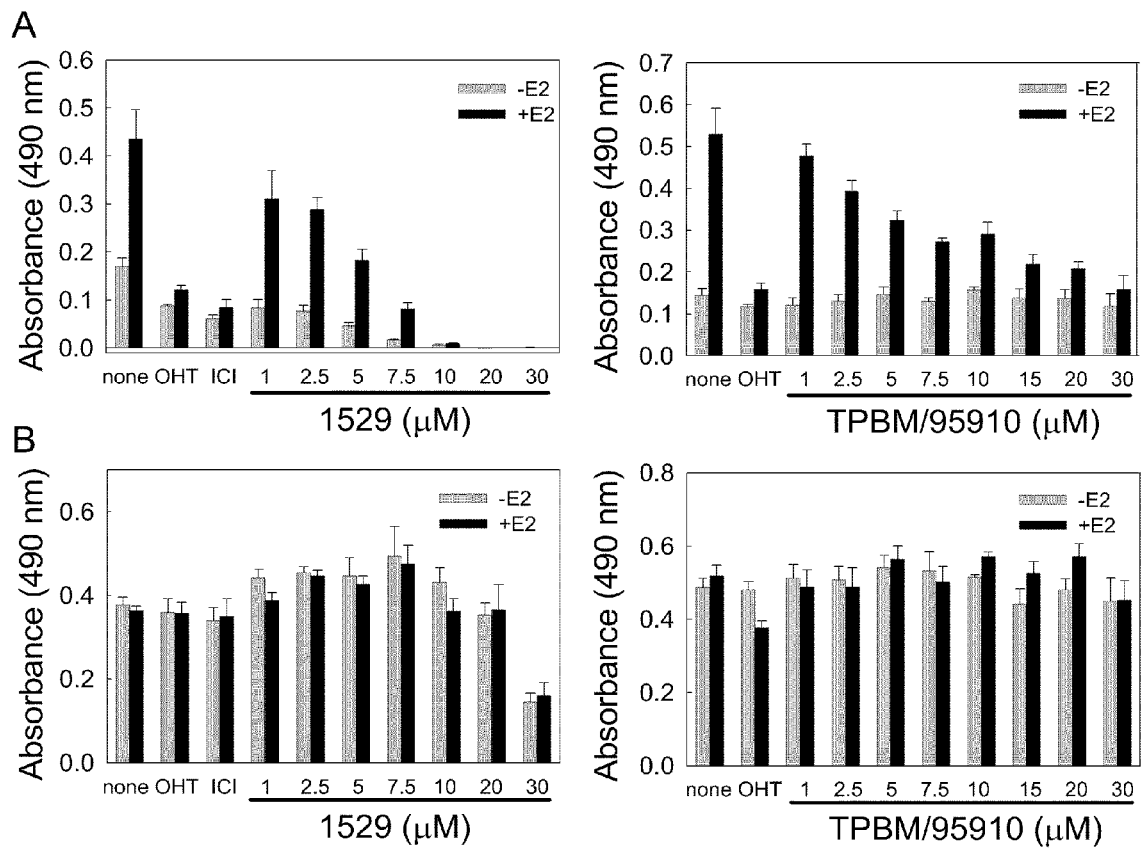
FIG. 6. Small molecule inhibitors of ER-mediated gene expression block estrogen-dependent growth of cancer cells. A. BG-1 ovarian cancer cells were maintained in medium lacking $E_2$ (grey bars), or containing 10 pM $E_2$ (black bars). OHT and ICI were at 1 nM. The cells were maintained for 5 days in the presence of TPBM/95910 or 1529 and viable cells determined using the MTS assay. B. ERα negative MDA-MB-231 cells were maintained in medium containing no $E_2$ (grey bars), or 10 pM $E_2$ (black bars). OHT and ICI were at 1 nM. The cells were maintained for 5 days in concentrations of TPBM/95910 and 1529 and viability assayed as described using MTS. The data represent the mean±SEM for 4 separate experiments at each concentration. The $IC_{50}$ for TPBM/95910 was obtained by curve-fitting using Sigma plot and had a high $R^2$ value.

A key goal of our studies was to determine whether small molecules selected for inhibition of binding of ERα to the cERE could block $E_2$-dependent growth of cancer cells. Consistent with earlier studies (44), we found that BG-1 cells exhibited a stronger and more reproducible $E_2$ stimulation of cell growth than MCF-7 cells. While the small molecules also inhibited estrogen-dependent growth of MCF-7 cells, we focused efforts on BG-1 cells. Data are shown for the most ERα-specific inhibitors, TPBM/95910 and 1529. Compound 1529 potently inhibited $E_2$-dependent growth of the BG-1 cells ($IC_{50}$~5 μM). However, >5 uM 1529 inhibited growth of the cells in the absence of $E_2$, suggesting a nonspecific effect at the higher inhibitor concentration (FIG. 6A, 1529). TPBM/95910 exhibited concentration-dependent inhibition of $E_2$-dependent growth of the BG-1 cells, with an $IC_{50}$ of 5 μM. At 30 μM, TPBM was as effective as a 100-fold excess of OHT in blocking $E_2$-dependent growth of BG-1 cells (FIG. 6A, TPBM).

To test for general cell toxicity, the ERα negative MDA-MB-231 cell line was used. Growth of the MDA-MB-231 cells was unaffected by 1-20 μM 1529, but was reduced by 50-60% at 30 μM 1529 (FIG. 6B, 1529). The data suggest that while 1529 elicits some $E_2$-dependent inhibition of cell growth, at higher concentrations it is toxic to cells. TPBM had no effect on $E_2$-independent growth of BG-1 cells (FIG. 6A, grey bars) or MDA-MB-231 cells (FIG. 6B). Studies of TPBM/95910, theophylline, 8-[(benzylthio)methyl]-(7CI, 8CI) in the National Cancer Institute Developmental Therapeutics Program testing program confirmed a lack of toxicity with 60 cancer cell lines over a wide range of concentrations up to 100 μM TPBM. Of the 60 cell lines tested at 100 μM TPBM/95910, only a few lung cancer cell lines showed >50% reduction in cell growth. Even at 100 μM, TPBM/95910 did not inhibit growth of any of the 12 tested lines of breast and ovarian cancer cells by 50% (46). Thus, TPBM exhibits low toxicity to cells and there is a large concentration difference the 5 μM $IC_{50}$ for TPBM inhibition of $E_2$-ERα-dependent growth of BG-1 cells and the >100 μM TPBM required for inhibition of $E_2$-ERα-independent breast and ovarian cell growth.

TPBM Inhibits $E_2$ and OHT—Induction of Endogenous Genes in Tamoxifen-Resistant Breast Cancer Cells—

Development of resistance to tamoxifen and other SERMs represents a major problem in endocrine therapy (7, 47-49). Thus, an important goal in the development of new inhibitors is to block ERα transcriptional activity in tamoxifen-resistant breast cancer cells. Since TPBM targets binding of ER to DNA and does not compete with estrogens for binding as SERMs do, we explored whether TPBM is effective in Tam-resistant MCF7ERαHA breast cancer cells. MCF7ERαHA cells are a Tetracycline-inducible MCF-7 model for Tam-resistant breast cancer in which doxycycline (Dox) induces overexpression of ERα (40,41). In these cells Tam and OHT are potent agonists (2,41). Because OHT stabilizes ERα, while $E_2$ down-regulates ERα, in MCF7ERαHA cells OHT is more effective than $E_2$ in inducing PI-9 (2). We used PI-9 as our test endogenous gene because elevated expression of PI-9 is associated with a poor prognosis and reduced survival in several human cancers (50-52). PI-9 is a primary estrogen-regulated gene (53,54) and $E_2$ and OHT elicit robust >100 fold inductions of PI-9 mRNA in MCF7ERαHA cells (2).

Figure 7:
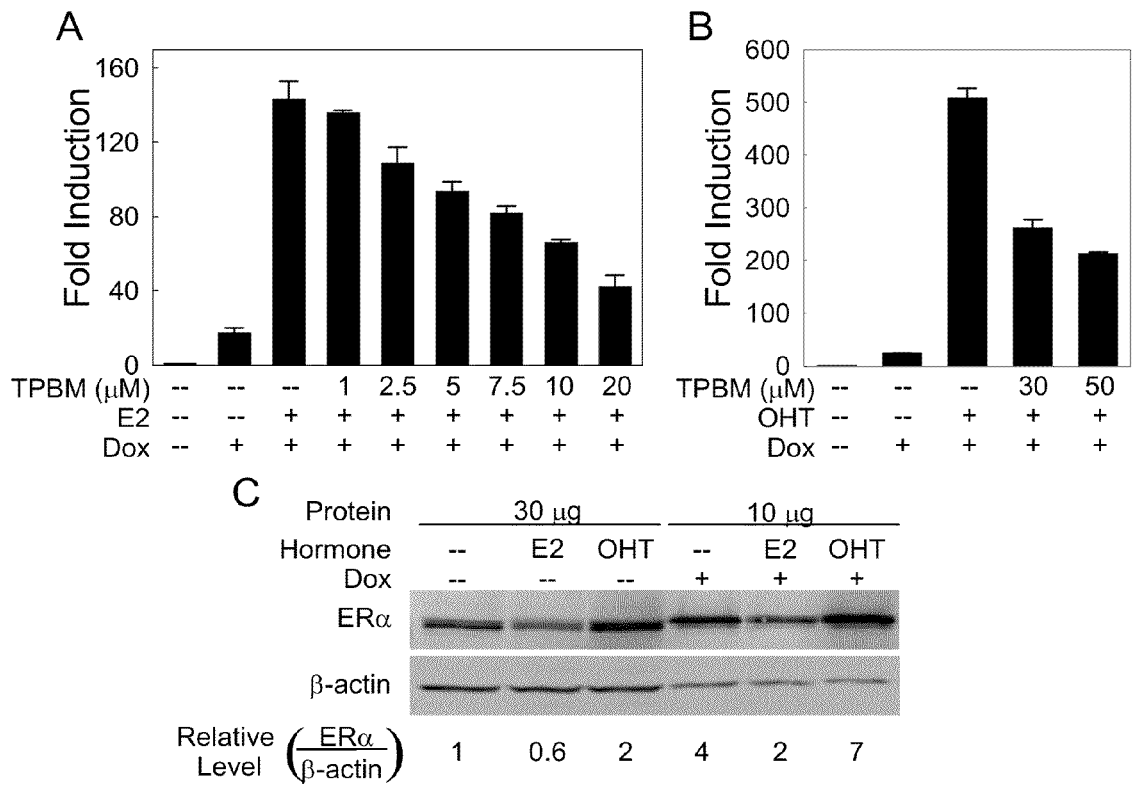
FIG. 7. TPBM inhibits $E_2$ and OHT mediated gene expression in a Tam-resistant cell line. MCF7ERαHA cells were maintained in 10% 6x charcoal-stripped FBS, treated with the 0.5 μg/ml Doxycycline (Dox) to induce ERα and 100 pM $E_2$ A or 500 pM OHT B and the indicated concentrations of 95910 for 24 h. The cells were harvested and PI-9 mRNA levels were determined by quantitative RT-PCR as described in Experimental Procedures. The high level of ERα in Dox-treated cells (E2− and Dox+) results in some ligand-independent transactivation of PI-9 by ERα. The data represents the mean±SEM for 3 separate experiments each assayed in triplicate. The $IC_{50}$ of 8.5 μM for TPBM/95910 inhibition of $E_2$ induction of PI-9 was obtained by curve-fitting using Sigma plot and had a high $R^2$ value. C Western blot analysis of ERα levels in MCF7ERαHA cells in the presence and absence of Doxycycline. MCF7ERαHA cells were maintained in medium containing or lacking 0.5 μg/ml Dox and no ligand, 100 pM $E_2$ or 500 pM OHT. The cells were harvested after 24 h, total cell extracts were prepared and analyzed for ERα content by Western blot as described in Experimental Procedures. To better visualize the differences in ERα levels in the uninduced and Dox-induced MCF7ERαHA cells 30 μg (3× more protein) was run for each uninduced sample and 10 μg of protein was run for each sample from MCF7ERαHA cells in which ERα was induced with Dox. ERα antibody was used at a dilution of 1:2,000. Relative levels of ERα were calculated by Phosphorimager quantitation of band intensity and normalization to actin (actin antibody was a 1:10,000 dilution). The ratio of unliganded (-$E_2$ and —OHT) ERα to actin in the MCF7ERαHA cells not treated with Dox to induce ERα was set equal to 1. The ratios of ERα levels in the Dox-treated and uninduced (−Dox) MCF7ERαHA cells were 3.7, 3.1 and 4.0 for cells maintained in medium with no ligand, $E_2$ and OHT, respectively. The data in C is representative of other Western blots.

Saturating $E_2$ (100 pM, FIG. 7A) and OHT (500 pM, FIG. 7B) induced PI-9 mRNA by 150 and 500 fold, respectively. TPBM (95910) elicited a concentration-dependent inhibition of $E_2$-ERα induction of PI-9 mRNA with an $IC_{50}$ of 8.5 μM (FIG. 7A). 30 μM TPBM (95910) was required to inhibit OHT-ERα induction of PI-9 mRNA by 48% (FIG. 7B). This is a stringent test because Western blotting followed by Phosphorimager quantitation of band intensities shows that MCF7ERαHA cells treated with Dox to induce ERα, express 3-4 fold more ERα in the presence of $E_2$ or OHT than MCF7ERαHA cells not treated with Dox (FIG. 7C). The less complete inhibition of PI-9 induction in the OHT-treated cells likely results from the ~4 fold higher level of ERα after OHT treatment than after $E_2$ treatment (FIG. 7C). The PI-9 gene is representative of the many genes that contain complex estrogen response elements including ERE half sites. To confirm that TPBM inhibits expression of an endogenous gene that contains a near consensus ERE we used the pS2 gene. While pS2 has no known role in ER-dependent tumors, it contains a well-studied imperfect ERE that differs from the cERE by only one nucleotide. When MCF7ERαHA cells were maintained for 24 h in medium containing doxycycline (to induce ERα) and 100 pM $E_2$, but no TPBM, pS2 mRNA was induced 24±3 fold (n=3 independent experiments). When the medium also contained 10 μM TPBM, induction of pS2 mRNA was reduced by 50% to 12±2 fold (n=3). These data demonstrate that TPBM inhibits ERα mediated gene expression in tamoxifen-resistant breast cancer cells that overexpress ERα.

TPBM does not Bind in the Ligand Binding Pocket of ERα and is not a Zinc Chelator—

Figure 8:
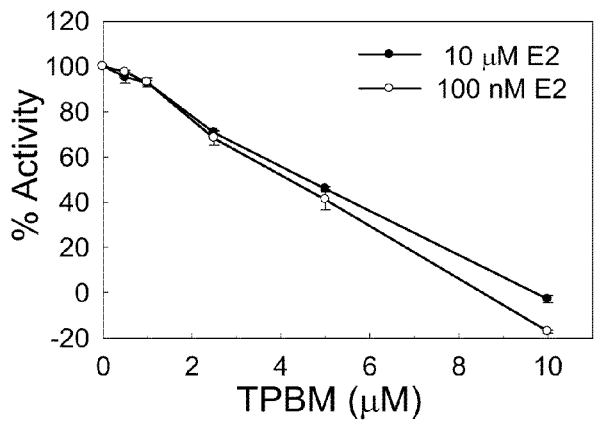
FIG. 8. High concentrations of $E_2$ do not reduce the ability of TPBM to inhibit binding of $E_2$-ERα to the flcERE. Assays were carried out essentially as described in the legend to FIG. 3 and Experimental Procedures. $E_2$ was present at the standard concentration of 100 nM (open circles) or at 10 μM (closed circles). The anisotropy change in the absence of inhibitor was set equal to 100%. The data represent the mean±SEM for 4 separate experiments. Error bars that are not visible are smaller than the symbols.

We performed experiments to test the possibility that TPBM inhibits $E_2$-ERα binding to the flcERE by binding in the ERα ligand binding pocket or as an electrophile that complexes zinc in the zinc fingers of ERα. We found that increasing the concentration of $E_2$ to 10 µM had no effect on the ability of TPBM to inhibit binding of ERα to the flcERE (FIG. 8).

The only other known small molecule ERα inhibitor that acts outside the ERα ligand binding pocket is the electrophile DIBA that chelates the zinc in the zinc fingers of ERs DNA binding domain (25,26). Wang and coworkers showed that pre-incubating with zinc largely blocks inhibition of ERα by DIBA (25). At 5 µM TPBM, binding of ERα to the flcERE was inhibited 76±7% (N=3) in the absence of zinc and 68±6% (n=3) in the presence of 50 µM zinc. Under the same conditions, pre-incubating with zinc prevented the zinc chelator ortho-phenanthroline from inhibiting ERα binding to the flcERE. Therefore, it is believed that TPBM does not act by chelating the zinc in the zinc fingers of ERα and is a novel ERα inhibitor that acts outside of the ERs ligand-binding pocket.

Discussion

In this work, in part we describe a broadly applicable HTS system for identifying small molecules that inhibit interaction of DNA binding proteins with their recognition sequences, demonstrate that a small molecule identified using this in vitro assay with isolated components functions in intact cells and show that certain small molecules can specifically and effectively block estrogen-dependent growth of cancer cells. TPBM is effective in tamoxifen-resistant breast cancer cells and therefore can serve as an effective therapeutic agent.

The HTS Screen—

Usually in HTS to identify small molecule inhibitors of macromolecular interactions, a cocktail containing all of the components is assembled and then incubated with each compound in the library (30). We were concerned that pre-forming the $E_2$-ERα-flcERE complex might eliminate those small molecules that bound at the protein-DNA interface. We therefore used the more complex approach of first incubating each test compound with $E_2$-ERα and then adding the flcERE. We compared this "sequential" screening method to the "cocktail" method. Only a few compounds showed somewhat different potency as inhibitors of $E_2$-ERα binding to the flcERE when assayed by the sequential and cocktail methods. While both the cocktail and sequential methods are robust screens ((55), Z'>0.5), the cocktail method is preferred because it is easier to implement in large scale HTS for steroid receptors.

Since we were primarily searching for inhibitors, we screened the libraries at a concentration of $E_2$-ERα that results in ~80% of maximal binding. This reduced the chances of identifying activators that reduce the concentration of $E_2$-ERα required for maximal binding. A brief examination of 37 small molecules that resulted in increased anisotropy and did not display intrinsic fluorescence, showed that all 37 small molecules altered the anisotropy of the free flcERE probe and were therefore not genuine activators. Screening the libraries at a receptor concentration that results in approximately half maximal binding to the HRE is one-way to determine the relative frequency of inhibitors and activators. However, screening at half-maximal binding results in smaller anisotropy changes and is better suited to HTS using the AR and PR, which are larger than ERα and produce much larger anisotropy increases when they bind to their HREs.

The structures of the inhibitors were diverse, but a substantial percentage of the inhibitors, including a preferred embodiment compound, TPBM, contained multiple rings that were joined by a flexible linker. While some small molecules that were detected using FAMA did not function in the cell-based transfection assay, a high percentage of the molecules identified in the initial screen function in intact cells.

Identification and Characterization of an Inhibitor of ERα Action in Cancer Cells—

The initial in vitro HTS screen employs a system containing only 2 pure components, a cERE and purified ERα. To be useful, inhibitors identified by this screen must inhibit ERα-mediated transcription in intact cells. Using a stably transfected breast cancer cell line that expresses endogenous ERα, we showed that small molecules such as TPBM can elicit a concentration-dependent inhibition of reporter gene expression. Small molecules as embodiments of the invention, e.g., those capable of at least partially blocking binding of ERα to a cERE, can also inhibit estrogen-dependent cancer cell growth. At 30 µM, TPBM and OHT both nearly completely inhibited estrogen-dependent growth of BG-1 cells. Interestingly, the $IC_{50}$ of 3.5 µM for inhibition of binding of ERα to the flcERE in FAMA is similar to the 5 µM $IC_{50}$ for inhibiting the estrogen-stimulated component of BG-1 cell growth, suggesting an association between inhibition of ERα binding to EREs and inhibition of cell growth.

To be useful in antagonizing estrogen action in cancer cells, a small molecule should exhibit good specificity for ERα and low overall toxicity. TPBM inhibited $E_2$-ERα-dependent cell growth with an $IC_{50}$ of 5 µM with no inhibition of the growth of ERα negative MDA MB-231 cells up to 30 µM. Independent testing of this compound against a panel of 60 cancer cell lines at the NCI Developmental Therapeutics Program showed that TPBM did not inhibit breast and ovarian cell growth up to 100 µM. Thus, TPBM shows >10 fold greater potency for inhibiting $E_2$-ERα-dependent cell growth relative to nonspecific toxicity. In contrast, for several other ERα inhibitors (1529, 638432 and 130796) the concentrations required to inhibit estrogen-dependent growth of BG-1 cells was at most a few fold lower than the concentration that was toxic to ER negative MDA MD-231 cells. These compounds are unlikely to be useful as antagonists of ER action in cells in a therapeutic context.

We compared the ability of TPBM to inhibit reporter gene transcription mediated by ERα, PR and GR in the same cell line expressing different reporter genes. Even at 30 µM, TPBM has little effect on reporter gene transcription by PR and GR. Since we tested the specificity of TPBM against closely related steroid hormone receptors and because TPBM has little or no toxicity to cells, it is unlikely to significantly inhibit a broad range of DNA binding transcription regulators.

Another important aspect of our study was to identify an ERα inhibitor that is active in tamoxifen-resistant breast cancer cells. Estrogen dependent cancers undergo natural selection to tamoxifen-resistant tumors through a variety of mechanisms, often maintaining expression of a functional ERα that is important for tumor growth (49). Recent studies show that an important feature of tamoxifen-resistant breast cancer cells that retain dependence on ERα for growth is loss of dependence on SRC3 and other p160 coactivators for $E_2$-ERα mediated gene transcription (41,56). ERα in these tumors must still bind DNA to activate transcription. Thus, our screening strategy that targets DNA binding may have advantages compared to a screening strategy that targets binding of p160 coactivators to ERα.

TPBM effectively blocked $E_2$-dependent induction of PI-9 mRNA in Tam-resistant MCF7ERαHA cells ($IC_{50}$ 8.5 µM). It is probably unusually difficult to inhibit ERα binding to the endogenous PI-9 ERU in the MCF7ERαHA cells and to the $(ERE)_3$ reporter in the T47D reporter gene cell line. In the MCF7ERαHA cells, the high level of ERα, 3-4 times higher than the already substantial level in MCF-7 cells (FIG. 7C) (40), coupled with use of saturating $E_2$, likely makes it difficult to achieve effective inhibition. Furthermore, the (cERE)$_3$-luciferase reporter stably transfected in the T47D cells will exhibit strong cooperative binding of E$_2$-ERα to the 3 cEREs (57), making it difficult for an inhibitor to block ERα binding to the EREs. Interestingly, the IC$_{50}$ of 10.5 and 8.5 µM for inhibition of E$_2$-ERα-mediated gene expression from the (cERE)$_3$-luciferase reporter in T47D cells and from the endogenous PI-9 gene in MCF7ERαHA cells are somewhat higher than the IC$_{50}$ of 5 µM for inhibiting E$_2$-dependent cancer cell growth.

TPBM is structurally unrelated to certain other small molecules known to inhibit nuclear receptor function. β-aminoketones were identified using HTS as inhibitors that covalently react with TR and inhibit coactivator binding (19). Their specificity for TR compared to other nuclear receptors has not been reported. DIBA is an electrophile originally identified as an inhibitor of binding of zinc finger proteins in retroviruses to their DNA binding sites and subsequently shown to inhibit ER action (25). Perhaps the most interesting property of DIBA is that it induces an ERα conformation that enhances the antagonist activity of tamoxifen in tamoxifen-resistant breast cancer cell lines (26). The utility of small molecules as probes for steroid receptor action was recently demonstrated by identification of a new coactivator binding surface on AR using small molecules selected by HTS as inhibitors of the binding of a coactivator peptide (58). These moderate potency (IC$_{50}$~50 µM) small molecule inhibitors are structurally distinct from TPBM. Since TPBM does not act by binding in ERs ligand binding pocket, or by chelating the zinc in ERs zinc fingers, and differs from known inhibitors, it represents a new class of ER inhibitor.

REFERENCES FOR EXAMPLE 1

1. Clarke, R., Liu, M. C., Bouker, K. B., Gu, Z., Lee, R. Y., Zhu, Y., Skaar, T. C., Gomez, B., O'Brien, K., Wang, Y., and Hilakivi-Clarke, L. A. (2003) Oncogene 22(47), 7316-7339
2. Jiang, X., Ellison, S. J., Alarid, E. T., and Shapiro, D. J. (2007) Oncogene 26(28), 4106-4114
3. Jiang, X., Orr, B. A., Kranz, D. M., and Shapiro, D. J. (2006) Endocrinology 147(3), 1419-1426
4. O'Lone, R., Frith, M. C., Karlsson, E. K., and Hansen, U. (2004) Mol Endocrinol 18(8), 1859-1875
5. Gradishar, W. J., and Cella, D. (2006) Jama 295(23), 2784-2786
6. Boonyaratanakornkit, V., and Edwards, D. P. (2004) Essays Biochem 40, 105-120
7. Deroo, B. J., and Korach, K. S. (2006) J Clin Invest 116(3), 561-570
8. Yager, J. D., and Davidson, N. E. (2006) N Engl J Med 354(3), 270-282
9. Pandey, K. R. (2007) Bmj 334(7600), 925
10. Smyth, J. F., Gourley, C., Walker, G., MacKean, M. J., Stevenson, A., Williams, A. R., Nafussi, A. A., Rye, T., Rye, R., Stewart, M., McCurdy, J., Mano, M., Reed, N., McMahon, T., Vasey, P., Gabra, H., and Langdon, S. P. (2007) Clin Cancer Res 13(12), 3617-3622
11. Smith, I. E., and Dowsett, M. (2003) N Engl J Med 348(24), 2431-2442
12. Winer, E. P. (2005) J Clin Oncol 23(8), 1609-1610
13. Boccardo, F. (2004) Clin Breast Cancer 5 Suppl 1, S13-17
14. Katzenellenbogen, B. S., Montano, M. M., Ekena, K., Herman, M. E., and McInerney, E. M. (1997) Breast Cancer Res Treat 44(1), 23-38
15. Lewis, J. S., and Jordan, V. C. (2005) Mutat Res 591(1-2), 247-263
16. Carroll, J. S., and Brown, M. (2006) Mol Endocrinol 20(8), 1707-1714
17. Klinge, C. M. (2001) Nucleic Acids Res 29(14), 2905-2919
18. Arkin, M. R., and Wells, J. A. (2004) Nat Rev Drug Discov 3(4), 301-317
19. Arnold, L. A., Estebanez-Perpina, E., Togashi, M., Jouravel, N., Shelat, A., McReynolds, A. C., Mar, E., Nguyen, P., Baxter, J. D., Fletterick, R. J., Webb, P., and Guy, R. K. (2005) J Biol Chem 280(52), 43048-43055
20. Kung, A. L., Zabludoff, S. D., France, D. S., Freedman, S. J., Tanner, E. A., Vieira, A., Cornell-Kennon, S., Lee, J., Wang, B., Wang, J., Memmert, K., Naegeli, H. U., Petersen, F., Eck, M. J., Bair, K. W., Wood, A. W., and Livingston, D. M. (2004) Cancer Cell 6(1), 33-43
21. Li, L., Thomas, R. M., Suzuki, H., De Brabander, J. K., Wang, X., and Harran, P. G. (2004) Science 305(5689), 1471-1474
22. Putt, K. S., Chen, G. W., Pearson, J. M., Sandhorst, J. S., Hoagland, M. S., Kwon, J. T., Hwang, S. K., Jin, H., Churchwell, M. I., Cho, M. H., Doerge, D. R., Helferich, W. G., and Hergenrother, P. J. (2006) Nat Chem Biol 2(10), 543-550
23. Verma, R., Peters, N. R., D'Onofrio, M., Tochtrop, G. P., Sakamoto, K. M., Varadan, R., Zhang, M., Coffino, P., Fushman, D., Deshaies, R. J., and King, R. W. (2004) Science 306(5693), 117-120
24. Moerke, N. J., Aktas, H., Chen, H., Cantel, S., Reibarkh, M. Y., Fahmy, A., Gross, J. D., Degterev, A., Yuan, J., Chorev, M., Halperin, J. A., and Wagner, G. (2007) Cell 128(2), 257-267
25. Wang, L. H., Yang, X. Y., Zhang, X., Mihalic, K., Fan, Y. X., Xiao, W., Howard, O. M., Appella, E., Maynard, A. T., and Farrar, W. L. (2004) Nat Med 10(1), 40-47
26. Wang, L. H., Yang, X. Y., Zhang, X., An, P., Kim, H. J., Huang, J., Clarke, R., Osborne, C. K., Inman, J. K., Appella, E., and Farrar, W. L. (2006) Cancer Cell 10(6), 487-499
27. Wang, S. Y., Ahn, B. S., Harris, R., Nordeen, S. K., and Shapiro, D. J. (2004) Biotechniques 37(5), 807-808, 810-807
28. Wang, S., Zhang, C., Nordeen, S. K., and Shapiro, D. J. (2007) J Biol Chem 282(5), 2765-2775
29. Mao, C., Flavin, K. G., Wang, S., Dodson, R., Ross, J., and Shapiro, D. J. (2006) Anal Biochem 350(2), 222-232
30. Rishi, V., Potter, T., Laudeman, J., Reinhart, R., Silvers, T., Selby, M., Stevenson, T., Krosky, P., Stephen, A. G., Acharya, A., Moll, J., Oh, W. J., Scudiero, D., Shoemaker, R. H., and Vinson, C. (2005) Anal Biochem 340(2), 259-271
31. Dietz, A. J., Jr., and Burgison, R. M. (1966) J Med Chem 9(4), 500-506
32. Dietz, A. J., Jr., and Burgison, R. M. (1966) J Med Chem 9(1), 160
33. Melvin, V. S., and Edwards, D. P. (2001) Methods Mol Biol 176, 39-54
34. Askew, E. B., Gampe, R. T., Jr., Stanley, T. B., Faggart, J. L., and Wilson, E. M. (2007) J Biol Chem 282(35), 25801-25816
35. Ozers, M. S., Hill, J. J., Ervin, K., Wood, J. R., Nardulli, A. M., Royer, C. A., and Gorski, J. (1997) J Biol Chem 272(48), 30405-30411
36. Putt, K. S., and Hergenrother, P. J. (2004) Anal Biochem 326(1), 78-86
37. Hergenrother, P. J. (2006) Curr Opin Chem Biol 10(3), 213-218

38. Wilson, V. S., Bobseine, K., and Gray, L. E., Jr. (2004) Toxicol Sci 81(1), 69-77
39. Nordeen, S. K., Kuhnel, B., Lawler-Heavner, J., Barber, D. A., and Edwards, D. P. (1989) Mol Endocrinol 3(8), 1270-1278
40. Fowler, A. M., Solodin, N., Preisler-Mashek, M. T., Zhang, P., Lee, A. V., and Alarid, E. T. (2004) Faseb J 18(1), 81-93
41. Fowler, A. M., Solodin, N. M., Valley, C. C., and Alarid, E. T. (2006) Mol Endocrinol 20(2), 291-301
42. Frasor, J., Chang, E. C., Komm, B., Lin, C. Y., Vega, V. B., Liu, E. T., Miller, L. D., Smeds, J., Bergh, J., and Katzenellenbogen, B. S. (2006) Cancer Res 66(14), 7334-7340
43. Cunningham, T. D., Jiang, X., and Shapiro, D. J. (2007) Cell Immunol 245(1), 32-41
44. Baldwin, W. S., Curtis, S. W., Cauthen, C. A., Risinger, J. I., Korach, K. S., and Barrett, J. C. (1998) In Vitro Cell Dev Biol Anim 34(8), 649-654
45. Cheng, J., Yu, D. V., Zhou, J. H., and Shapiro, D. J. (2007) J Biol Chem 282(42), 30535-30543
46. http://dtp.nci.nih.gov/
47. Jordan, V. C. (2001) Ann N Y Acad Sci 949, 72-79
48. Katzenellenbogen, B. S. (2000) J Soc Gynecol Investig 7(1 Suppl), S33-37
49. Osborne, C. K., Shou, J., Massarweh, S., and Schiff, R. (2005) Clin Cancer Res 11 (2 Pt 2), 865s-870s
50. Medema, J. P., de Jong, J., van Hall, T., Melief, C. J., and Offring a, R. (1999) J Exp Med 190(7), 1033-1038
51. ten Berge, R. L., Meijer, C. J., Dukers, D. F., Kummer, J. A., Bladergroen, B. A., Vos, W., Hack, C. E., Ossenkoppele, G. J., and Oudejans, J. J. (2002) Blood 99(12), 4540-4546
52. van Houdt, I. S., Oudejans, J. J., van den Eertwegh, A. J., Baars, A., Vos, W., Bladergroen, B. A., Rimoldi, D., Muris, J. J., Hooijberg, E., Gundy, C. M., Meijer, C. J., and Kummer, J. A. (2005) Clin Cancer Res 11 (17), 6400-6407
53. Krieg, A. J., Krieg, S. A., Ahn, B. S., and Shapiro, D. J. (2004) J Biol Chem 279(6), 5025-5034
54. Krieg, S. A., Krieg, A. J., and Shapiro, D. J. (2001) Mol Endocrinol 15(11), 1971-1982
55. Zhang, J. H., Chung, T. D., and Oldenburg, K. R. (1999) J Biomol Screen 4(2), 67-73
56. Naughton, C., MacLeod, K., Kuske, B., Clarke, R., Cameron, D. A., and Langdon, S. P. (2007) Mol Endocrinol 21(11), 2615-2626
57. Mattick, S., Glenn, K., de Haan, G., and Shapiro, D. J. (1997) J Steroid Biochem Mol Biol 60(5-6), 285-294
58. Estebanez-Perpina, E., Arnold, A. A., Nguyen, P., Rodrigues, E. D., Mar, E., Bateman, R., Pallai, P., Shokat, K. M., Baxter, J. D., Guy, R. K., Webb, P., and Fletterick, R. J. (2007) Proc Natl Acad Sci USA 104(41), 16074-16079

Example 2

Methods of Screening Theophylline Compounds

To inhibit ERα binding to the ERE, we developed and implemented an HTS fluorescence anisotropy microplate assay (FAMA) (27). The FAMA approach has been used to demonstrate active displacement in the binding of full-length SRC1 to ERE-ER complexes (28). To use the FAMA as an HTS assay, a fluorescein-labeled consensus ERE (flcERE) is synthesized (28,29). When polarized light excites the flcERE, the relatively small flcERE usually undergoes rotational diffusion more rapidly than the time required for light emission. Therefore, the position of the flcERE at the time of light emission is largely randomized, resulting in depolarization of most of the emitted light. When full-length ERα binds to the flcERE, the larger size of the flcERE:ERα complex causes slower rotation, increasing the likelihood that the flcERE:ERα complex will be in the same plane at the time of light emission as it was at the time of excitation. Therefore, the emitted light remains highly polarized. A receptor-DNA interaction increases fluorescence polarization (FP) and fluorescence anisotropy (FA). Although FA assays based on using a labeled DNA binding site for the protein of interest represent an attractive approach, a study using this in vitro strategy to identify small molecule inhibitors of the b-zip DNA binding transcription factors failed to identify specific inhibitors that function in cells (30).

Here we used FAMA to conduct HTS and identified a small molecule, a theophylline compound. In a particular embodiment, a preferred compound is theophylline, 8-[(benzylthio)methyl]-(7CI,8CI) (TPBM; an 8-alkyl-thio-thiated theophylline) (31,32), that specifically inhibits $E_2$-induced, ERα-mediated, gene expression in intact cells, without significantly inhibiting PR and GR mediated gene expression. TPBM also inhibits $E_2$ and 4-hydroxytamoxifen (OHT, the active metabolite of tamoxifen) induction of an endogenous gene in tamoxifen-resistant breast cancer cells. TPBM is not toxic to ERα negative cells and exhibits dose-dependent inhibition of the estrogen-dependent growth of ERα positive cancer cells. Our data show that an in vitro assay, using a protein-free consensus ERE and purified ERα, can identify small molecule inhibitors that block ER-mediated gene expression and estrogen-dependent growth of cancer cells.

Example 3

Methods of Synthesis of Theophylline Compounds

Compositions including theophylline compounds are prepared and synthesized as understood in the art. See, e.g., descriptions in connection with structures and the generation of compounds and variants and derivatives thereof. One of ordinary skill in the art can recognize and will readily appreciate the synthesis of compositions including compounds in connection with the invention.

a. U.S. Pat. No. 3,624,216 Stein, et al. Nov. 30, 1971; 8-Substituted Theophyllines As Anti-inflammatory Agents;
b. U.S. Pat. No. 3,624,215; U.S. Pat. No. 5,587,378 Suzuki, et al. Dec. 24, 1996; Therapeutic agent for Parkinson's disease;
c. US 20070265296 Dalton; James T. et al. Nov. 15, 2007; Nuclear receptor binding agents;
d. US 20050187267 Hamann, Lawrence G.; et al. Aug. 25, 2005, Sulfonylpyrrolidine modulators of androgen receptor function and method;
e. Steinsapir J, Rojas A M, Tchernitchin A, et al. Am J Physiol Endocrinol Metab. 1982; 242: E121-E126; Theophylline-estrogen interaction in the rat uterus: role of the ovary;
f. (WO/2006/091897) Derivatives of 8-substituted xanthines;
g. Mineo Satoshi, Ogura Haruo, Nakagawa Kunio; Vol. 28, No. 9(19800925) pp. 2835-2838; Chemical & pharmaceutical bulletin, The Pharmaceutical Society of Japan ISSN:00092363; Studies on Heterocyclic Compounds. XXXII. Synthesis of 8-Substituted Theophyllines from 6-Amino-5-benzylideneamino-1,3-dimethyluracils with Nickel Peroxide;

h. Senga Keitaro, Shimizu Kayoko, Nishigaki Sadao, Chemical & pharmaceutical bulletin Vol. 25, No. 3(19770325) pp. 495-497, The Pharmaceutical Society of Japan ISSN:00092363, Oxidative Cyclization of 6-Amino-5-benzylideneamino-1,3-dimethyluracils with Thionyl Chloride. A Convenient Synthesis of 8-Substituted Theophyllines;
i. U.S. Pat. No. 5,670,498; U.S. Pat. Nos. 5,734,052; 7,253,176; 5,734,051
j. WO/1994/025462) 8-Substituted 1,3,7-Trialkyl-Xanthine Derivatives As A2-Selective Adenosine Receptor Antagonists
k. Reid and R. Torinus, Chem. Ber., 92, 2902/1959
l. Baraldi Pier G et al., Expert Opinion on Drug Discovery September 2007, Vol. 2, No. 9, Pages 1161-1183 (doi: 10.1517/17460441.2.9.1161), Novel 8-heterocyclyl xanthine derivatives in drug development—an update.
m. Daly J W, Padgett W, Shamim M T, Butts-Lamb P, Waters J. 1,3-Dialkyl-8-(p-sulfophenyl)xanthines: potent water-soluble antagonists for A1- and A2-adenosine receptors. J Med Chem. 1985 April; 28(4):487-92.
n. Goodsell E B, Stein H H, Wenzke K J. 8-substituted theophyllines. In vitro inhibition of 3',5'-cyclic adenosine monophosphate phosphodiesterase and pharmacological spectrum in mice. J Med Chem. 1971 December; 14(12):1202-5.
o. Zimmer H, Joseph B. Mettalia, Jr., And R. Atchley; The Ohio Journal Of Science, Vol. 63 May, 1963 No. 3:97-102, Potential Anticancer Compounds. iii. Synthesis Of Some 8-Substituted Caffeines And Theophyllines.
p. Daly J, Padgett, W L and Shamin M T 1986 Analogous of caffeine and theophylline: Effect of structural alterations on affinity at adenosine recpetors. J. Med. Chem. 29:1305-1308
q. Bruns R, Daly, J W and Snyder S H 1983 Adenosine receptor binding:Structure-activity analysis generates extremely potent xanthine antagonists. Proc. Natl. Acad. Sci USA 80:2077-2080
r. Gondova T, Kralik, P and Gonda, J. 1989 Determination of some thermodynamic characteristics of melting of 8-alkyltheophyllines by the DSC method. Thermochimica Acta 156:147-155
s. Jacobson K A, Kiriasis L, Barone S, Bradbury B J, Kammula U, Campagne J M, Secunda S, Daly J W, Neumeyer J L, Pfleiderer W 1989 Sulfur-containing 1,3-dialkylxanthine derivatives as selective antagonists at A1-adenosine receptors. J Med Chem 32:1873-9
t. European Patent Documents EP0011399; EP0590919B1; EP0956855B1; Application EP0430300A2 by Morimoto A, 1990 Xanthine derivatives, their production and use.

Example 4

Steroid Receptor Inhibitors

We discovered that certain compounds, including 8-substituted theophyllines, could function effectively as inhibitors of steroid hormone receptor action in cells, cancers, and other conditions.

The hormone estrogen binds to a protein called the estrogen receptor (ER) and androgens, such as tesototerone, bind to the androgen receptor (AR). The complex of estrogen and the estrogen receptor and androgens and androgen receptor bind to specific sequences on DNA causing the copying of the nearby DNA and stimulating the production of the RNA blueprints that specify the production of proteins that stimulate cell division and migration. In this way, the estrogen-estrogen receptor complex plays a critical role in the growth and spread (metastases) of many breast cancers and the androgen-androgen receptor complex plays a key role in the growth and spread of many primary and recurrent prostate cancers.

The important role of estrogens in breast cancer is illustrated by the widespread use of aromatase inhibitors, tamoxifen and faslodex/fulvesterant in endocrine therapy for breast cancer. Similarly, AR antagonists, such as bicalutamide, are primary endocrine therapies for prostate cancer. Current generation small molecule inhibitors of ER and AR in cancer work by binding to the same site on the receptor as estrogens and androgens and competing with the hormones for binding to the site. For example, the widely used cancer therapeutic, tamoxifen, binds to the same place on the estrogen receptor as estrogens, and thereby prevents their binding to the estrogen receptor and blocks their action. Over time, breast cancers usually develop resistance to therapies such as tamoxifen. Although recurrent prostate cancers depend on androgen receptor for growth, they are resistant to current anti-androgens and there are few therapeutic options for these recurrent tumors. There is therefore a strong need for new classes of inhibitors, including such that may target different sites in steroid hormone receptor action.

The most common biological actions of steroid hormone receptors, including the estrogen, progesterone and androgen receptors, result from their ability to bind to specific DNA sequences and regulate the copying of nearby DNA leading to the production of proteins that influence important processes, such as cell growth and migration. To identify small molecules that disrupt an interaction such as the binding of the estrogen-estrogen receptor complex to DNA, we use a technique called high throughput screening (HTS) that allows rapid testing of many thousands of molecules. We developed and implemented a new type of high throughput screen and used it to identify and characterize small molecules that inhibit binding of steroid receptors to their DNA response elements.

We screened about 12,000 small molecules in a library developed at the University of Illinois and in the National Institutes of Health (NIH), National Cancer Institute (NCI) Diversity set. Small molecule hits were then validated, evaluated for potency (the amount of the small molecule required to produce an effect), for efficacy (the maximum effect seen) and for specificity for an individual steroid hormone receptor. We tested the best small molecules in human breast cancer cells and showed that a class of compounds, including in particular one small molecule example, can specifically inhibit the ability of estrogen-ER to activate the expression of a test gene with little or no effect on the ability of other receptors, the progesterone and glucocorticoid receptors to turn on genes that respond to those hormones in the same cells. The particular small molecule is not toxic to cells in tests conducted both in our laboratory and at the NIH National Cancer Institute. At low concentrations, this small molecule blocks the estrogen-dependent growth of cancer cells. This set of properties, high potency and efficacy for inhibiting estrogen-dependent growth of cancer cells, very low toxicity to other cells, and high specificity, makes this compound and the class useful in the context of therapeutic compositions and methods, e.g., for breast cancer and other conditions.

To see whether related 8-substituted theophyllines would show useful or enhanced potency, we acquired and tested about 70 structurally related 8-substituted small molecules.

Three of these small molecules with various 8-substitutions show strongly enhanced potency as inhibitors of estrogen-estrogen receptor induced gene expression and show high specificity and low toxicity.

Figure 9:
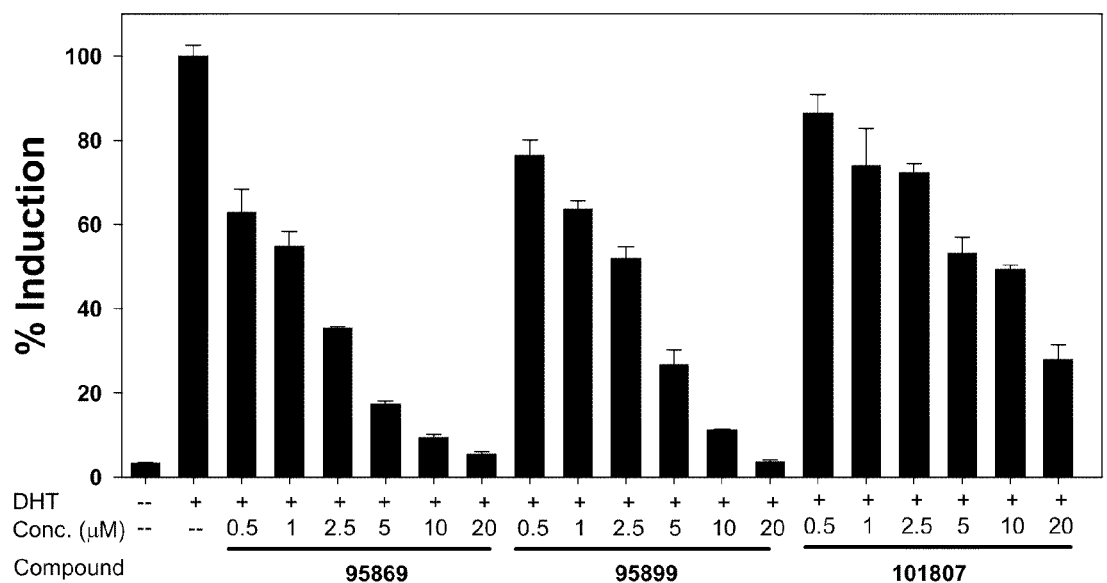
FIG. 9. Effect of some Theophylline-related compounds on AR-mediated gene expression in stable HeLa-AR cells. Assays were performed as described for ER in the legend to FIG. 4 and PR/GR in FIG. 5. The cells were incubated with 80 pM DHT and the indicated concentration of each small molecule. Luciferase activity was measured after 24 hours. The data represent the mean±SEM for 3 separate experiments at each concentration.

One other compound in this group appears to be an effective inhibitor of progesterone receptor. Progesterone receptor can block the action of estrogen receptor. Estrogens protect against the disease multiple sclerosis. Other compounds in this group are effective inhibitors of androgen receptor (FIG. 9). Androgen receptor plays a key role in prostate cancer.

We have surprisingly discovered that 8-substituted theophyllines represent an entirely new class of inhibitors of steroid hormone receptor action. These small molecules can be useful in therapeutic contexts for hormone-dependent breast and prostate cancer and for other endocrine-related diseases, such as multiple sclerosis (M.S.). Breast and prostate cancers that become resistant to antiestrogen and antiandrogen therapy often show changes that enable them to work without their hormones. However, they still need to bind to DNA. Thus, these compounds target a site that is difficult for the receptor proteins to overcome and/or serve in the aspect of resistance. Since the ER and AR in resistant tumors still must bind to DNA to work, these small molecules can work in tumors that are resistant to current anticancer drugs. We disclose that in embodiments, an ER inhibitor of the invention can be useful as a breast cancer therapeutic. In embodiments, an AR inhibitor of the invention can be useful as a prostate cancer therapeutic. In embodiments, a PR inhibitor can be useful as a multiple sclerosis therapeutic.

As an example, compound 95910 is a preferred embodiment. Certain compound numbers indicated are designations from the National Institutes of Health National Cancer Institute (NIH NCI) library (NSC numbers). Compound 95910 is considered a lead compound because of its properties, which include: (a) Little or no inhibition of PR and GR at 30 µM; (b) significant inhibition of estrogen dependent cancer cell growth ($IC_{50}$ 5 µM) and extremely low toxicity. No toxicity in our assays at 30 µM at 1 day and at 5 days and very little toxicity ($IC_{50}$>100 µM) in all 12 tested breast and ovarian cancer cell lines (data from NCI testing).

Additional compounds are also useful. Compounds 74358, 101794 and 14147 have $IC_{50}$ values for inhibiting etrogen-ER-mediated transcription in breast cancer cells that are several fold lower than 95910. Although 74358 and 101794 inhibit PR and GR, the difference between the $IC_{50}$ values for ER compared to PR and GR are large (7-25 fold) for 74358 and 101794. At 30 µM, 95910 slightly inhibits GR. Compound 14147 has virtually no effect on GR and a good toxicity profile but inhibits PR nearly as well as ER. In an embodiment, inhibiting PR as well as ER may be useful in the context of breast cancer therapy. Compound 101794 showed no toxicity in a short-term mouse study that used very high levels of 101794 (up to 400 mg/kg).

The structures for certain compounds herein are as follows:

14147

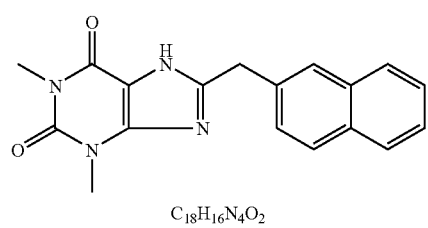

$C_{18}H_{16}N_4O_2$

-continued

74358

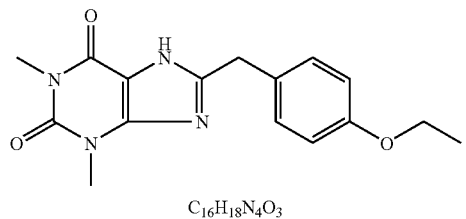

$C_{16}H_{18}N_4O_3$

TPEP/74361

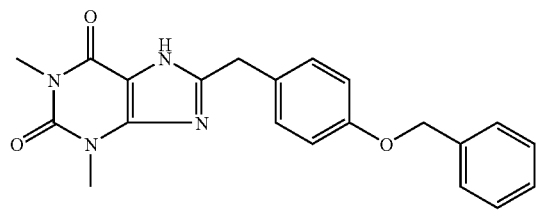

$C_{21}H_{20}N_4O_3$

TPBM/95910

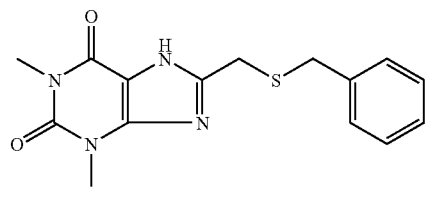

$C_{15}H_{16}N_4O_2S$

8-Benzylsulfanylmethyl-1,3-dimethyl-3,7-dihydro-purine-2,6-dione ($C_{15}H_{16}N_4O_2S$ Mass: 316.10 Mol. Wt.: 316.38)

101794

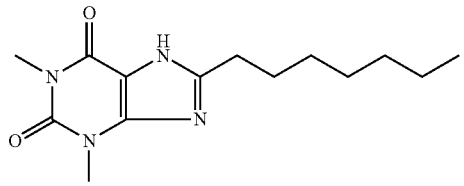

8-Heptyl-1,3-dimethyl-3,7-dihydro-purine-2,6-dione ($C_{14}H_{22}N_4O_2$)

Example 5

Androgen Receptor Action and Small Molecule Inhibitors

We also targeted androgen receptor action which can have significance in conditions such as prostate cancer.

The androgenic hormones, testosterone and dihydrotestosterone (DHT) bind to a protein known as the androgen receptor (AR). The complex of androgen with AR binds to specific DNA sequences and stimulates the production of RNA blueprints for the production of proteins involved in stimulating cell division and migration. In this way, the AR-hormone complex plays a critical role in the growth and spread of androgen-dependent and recurrent prostate cancers (1-11). Antagonists such as flutamide and bicalutamide (also known as casodex), bind to the same site on AR as testosterone and DHT, block androgen binding and prevent the AR from increasing growth of prostate cancer cells. Blocking androgen production and the administration of AR antagonists are widely used in prostate cancer therapy. However, prostate tumors eventually become resistant and recur with very limited effective therapeutic options (8, 12-17). Even when circulating androgen levels are reduced to undetectable levels by medical or surgical castration, the AR continues to play a key role in the growth of recurrent prostate cancers (1-9, 11-14, 17). Thus there is a strong need to develop new therapeutic strategies that block the AR from promoting prostate cell growth.

We used information gained from the high throughput screening using our fluorescence anisotropy microplate assay (FAMA) to identify substituted theophyllines that are potent AR inhibitors and prevent the DHT-AR complex from activating transcription of a DHT-AR inducible reporter gene. These inhibitors are relatively specific for AR, having little ability to inhibit transcription of estrogen receptor (ER) and progesterone receptor (PR)-dependent reporter genes. Thus these compounds can be useful in the context of prostate cancer therapeutics and other applications. Furthermore, this data demonstrates that substituted theophyllines represent a novel class of inhibitors effective against a range of steroid hormone receptors. In embodiments, compositions and methods are useful for inhibition of one or more of the following groups: nuclear hormone receptors; steroid hormone receptors; estrogen and androgen receptors; estrogen receptors; and androgen receptors.

Certain compounds were investigated regarding the ability to function as androgen receptor inhibitors. These compounds include those designated with NSC numbers as follows:

95869 (Theophylline, 8-(propylthio)-2-thio-(7CI, 8CI) or 1,3-Dimethyl-8-propylsulfanyl-2-thioxo-1,2,3,7-tetrahydro-purin-6-one);

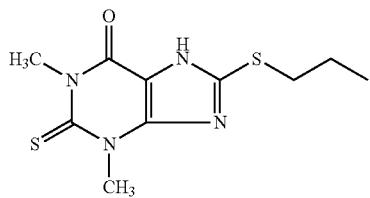

958869 $C_{10}H_{14}N_4OS_2$ 95899 (Theophylline, 8-(cyclohexylthio)-2-thio-(7CI,8CI) or 8-Cyclohexylsulfanyl-1,3-dimethyl-2-thioxo-1,2,3,7-tetrahydro-purin-6-one

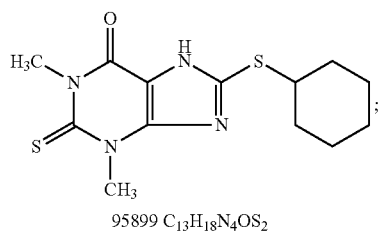

95899 $C_{13}H_{18}N_4OS_2$ and 101807 (8-Bicyclo[2.2.1]hept-2-yl-1,3-dimethyl-3,7-dihydro-purine-2,6-dione)

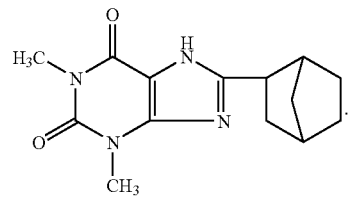

101807 $C_{14}H_{18}N_4O_2$

TABLE 2

Activity of androgen receptor inhibitor compounds.

| NSC no. | AR-IC$_{50}$ (μM) | AR at 10 μM | ER at 10 μM | PR at 30 μM |
|---|---|---|---|---|
| 95869 | 1 | 90 | 20 | 0 |
| 95899 | 2.5 | 88 | 36 | 42 |
| 101807 | 5 | 50 | 0 | 71 |

The activity of androgen receptor compounds was tested, and the results are shown in Table 2 and FIG. 9. The results demonstrate examples of significant activity.

REFERENCES

1. Ichikawa, T., Suzuki, H., Ueda, T., Komiya, A., Imamoto, T., and Kojima, S. (2005) Cancer Chemother Pharmacol 56 Suppl 1, 58-63
2. Mohler, J. L., Gregory, C. W., Ford, O. H., 3rd, Kim, D., Weaver, C. M., Petrusz, P., Wilson, E. M., and French, F. S. (2004) Clin Cancer Res 10(2), 440-448
3. Gelmann, E. P. (2002) J Clin Oncol 20(13), 3001-3015
4. Frydenberg, M., Stricker, P. D., and Kaye, K. W. (1997) Lancet 349(9066), 1681-1687
5. Debes, J. D., and Tindall, D. J. (2004) N Engl J Med 351(15), 1488-1490
6. Taplin, M. E., and Balk, S. P. (2004) J Cell Biochem 91(3), 483-490
7. Chen, C. D., Welsbie, D. S., Tran, C., Baek, S. H., Chen, R., Vessella, R., Rosenfeld, M. G., and Sawyers, C. L. (2004) Nat Med 10(1), 33-39
8. Balk, S. P. (2002) Urology 60(3 Suppl 1), 132-138; discussion 138-139
9. Visakorpi, T., Hyytinen, E., Koivisto, P., Tanner, M., Keinanen, R., Palmberg, C., Palotie, A., Tammela, T., Isola, J., and Kallioniemi, O. P. (1995) Nat Genet 9(4), 401-406
10. Culig, Z., Comuzzi, B., Steiner, H., Bartsch, G., and Hobisch, A. (2004) J Steroid Biochem Mol Biol 92(4), 265-271
11. Gregory, C. W., Johnson, R. T., Jr., Mohler, J. L., French, F. S., and Wilson, E. M. (2001) Cancer Res 61(7), 2892-2898
12. Taplin, M. E., Bubley, G. J., Shuster, T. D., Frantz, M. E., Spooner, A. E., Ogata, G. K., Keer, H. N., and Balk, S. P. (1995) N Engl J Med 332(21), 1393-1398
13. Taplin, M. E., Rajeshkumar, B., Halabi, S., Werner, C. P., Woda, B. A., Picus, J., Stadler, W., Hayes, D. F., Kantoff, P. W., Vogelzang, N. J., and Small, E. J. (2003) J Clin Oncol 21(14), 2673-2678

14. Feldman, B. J., and Feldman, D. (2001) Nat Rev Cancer 1(1), 34-45
15. Zhao, X. Y., Malloy, P. J., Krishnan, A. V., Swami, S., Navone, N. M., Peehl, D. M., and Feldman, D. (2000) Nat Med 6(6), 703-706
16. Gaddipati, J. P., McLeod, D. G., Heidenberg, H. B., Sesterhenn, I. A., Finger, M. J., Moul, J. W., and Srivastava, S. (1994) Cancer Res 54(11), 2861-2864
17. Tan, J., Sharief, Y., Hamil, K. G., Gregory, C. W., Zang, D. Y., Sar, M., Gumerlock, P. H., deVere White, R. W., Pretlow, T. G., Harris, S. E., Wilson, E. M., Mohler, J. L., and French, F. S. (1997) Mol Endocrinol 11 (4), 450-459

Example 6

Further Compositions and Methods

In embodiments, the invention provides compositions and methods relating to one or more compounds having the structural formula FX2:

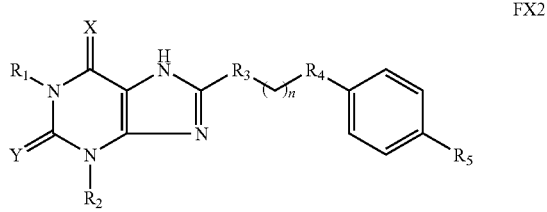

FX2 wherein X or Y each independently is S, O, or Se;
$R_1$ or $R_2$ each independently is H or $C_{1-6}$ alkyl;
$R_3$ is —S—$CH_2$—, —O—$CH_2$—, —$CH_2$—S, or —$CH_2$—O—;
$R_4$ is —C=O or —NH—C=O;
$R_5$ is F, Cl, Br, I, At, or other group with electronegativity from 1.5 to 4.0; and
n is 1 to 6.

In embodiments of compounds of formula FX2, an alkyl moiety independently may be optionally substituted by 1 to 5 substituents wherein substituents are independently selected from a group consisting of hydroxy, alkoxy, cyano, ethynyl, alkoxycarbonyl, aryl, acyl or heterocycle. In embodiments, an alkyl group which may be substituted includes the compound component between $R_3$ and $R_4$.

In an embodiment, the invention provides a compound and methods relating to a compound having formula NSC 97998:

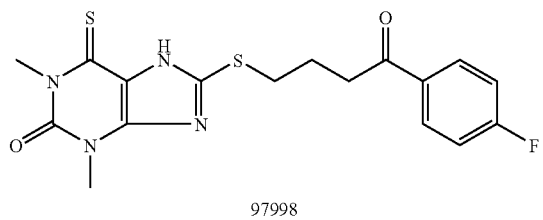 [SMILES: Cn1c(=S)c2[nH]c(SCCCC(=O)c3ccc(F)cc3)nc2n(C)c1=O ; "97998"]

97998

In an embodiment, the invention provides a compound and methods relating to a compound of formula FX2 wherein said compound has formula 97998. The compound NSC 97998 may be referred to as 97998/TPSF.

In embodiments, compounds of formula FX2 and NSC 97998/TPSF are used as estrogen receptor alpha (ERα) inhibitors. A chemical name for compound TPSF/NSC 97998 is Butyrophenone, p-fluoro-4-(1,2,3,6,-tetrahydro-1,3-dimethyl-2-oxo-6-thionopurin-8-ylthio), with a chemical composition of $C_{17}H_{17}FN_4O_2S_2$. By screening structural derivatives of our NSC 95910/TPBM we identified NSC 97998/TPSF and further identify additional compounds, e.g., compounds of formula FX2, as compounds capable of inhibition of ERα. In particular embodiments, compounds may demonstrate $IC_{50}$ values in the nanomolar range. See Table 3 which indicates results of testing for inhibition of certain biological activity, including inhibition of $E_2$-ERα dependent gene activation and ER positive and ER negative breast cancer cell growth.

TABLE 3

Activity of Compound NSC 97998/TPSF regarding gene expression and cancer cell growth.

| Activity | $IC_{50}$ (μM) |
|---|---|
| Gene Expression | |
| ERE-Luc | 0.7 |
| Endog. PI-9 | 0.2 |
| AR | 33 |
| GR | 10 |
| Cell Growth | |
| MCF-7 (ER. Pos. cells) | 2 |
| MDA-MB-231 (ER Neg. cells) | >>30 (0% in.) |

Table 3 summarizes data from dose-response curves for inhibition of E2-ERα-mediated gene expression and cell growth. Inhibition of gene expression was assayed in two systems. We used 100 nM 17β-estradiol ($E_2$) in ERα positive T47D, human breast cancer cells, stably transfected to express an $(ERE)_3$-luciferase reporter gene (ERE-Luc). We used quantitative real-time PCR to evaluate the ability of 97998/TPSF to inhibit induction of endogenous proteinase inhibitor 9 (PI-9) mRNA by 10 nM $E_2$ in ERα positive MCF-7, breast cancer cells (Endog. PI-9). To evaluate specificity, we tested the ability of 97998/TPSF to inhibit gene expression by other steroid receptors. Androgen receptor (AR), in stably transfected Hela cells, was activated by 1 μM dihydrotestosterone (DHT). Glucocorticoid receptor (GR), in stably transfected T47D human breast cancer cells, was activated by 100 nM dexamethasone (Dex) (see FIG. 11). We also tested the ability of 97998/TPSF to inhibit estrogen-dependent growth of ERα-containing MCF-7, human breast cancer cells (see FIG. 12). Toxicity was evaluated by testing 97998/TPSF for inhibition of growth of ERα negative MDA-MB-231 human breast cancer cells. These 4-day growth studies were similar to the studies in MCF-7 cells. At all inhibitor concentrations tested, including 30 μM, 97998/TPSF did not inhibit growth of the MDA MB-231 cells (0% inhibition). The gene expression studies are the average of at least 3 experiments at each concentration. The MCF-7 and MDA-MB-231 cell growth inhibition studies are the average of 8 wells of cells for each data point. All $IC_{50}$ values were calculated by curve fitting using Sigma Plot.

Figure 10:
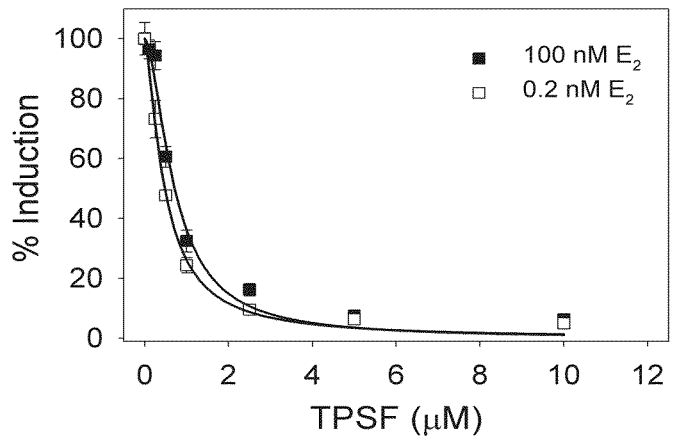
FIG. 10 illustrates results for testing for inhibition of $E_2$-ERα mediated induction of gene expression. Assays were performed as described in the legend to FIG. 4 and contained either 0.2 nM $E_2$ (open squares) or 100 nM $E_2$ (filled squares) and the indicated concentrations of TPSF. The data represents the mean±sem for at least 3 separate experiments at each concentration of inhibitor. $IC_{50}$ values were calculated by curve fitting using Sigma Plot and were 0.4 μM for the 0.2 nM $E_2$ samples and 0.7 μM for the 100 nM $E_2$ samples.

The compound 97998/TPSF does not compete with $E_2$ for binding to ERα and acts outside of the ligand binding pocket of ERα. Increasing the concentration of $E_2$ 500 fold from 0.2 nM to 100 nM only increased the $IC_{50}$ for inhibiting $E_2$-ERα-mediated transcription of the stably transfected $(ERE)_3$-luciferase reporter gene in T47D cells from 0.4 μM to 0.7 μM (FIG. 10). Also, at 10 nM $E_2$, which is a concentration of $E_2$ higher than is needed for saturated binding to ERα, the $IC_{50}$ for inhibiting $E_2$-ERα-mediated transcription of the endogenous PI-9 gene in MCF-7 cells is 0.2 μM (see FIG. 11). These data show that 97998/TPSF does not inhibit ERα by competing with estrogens for binding in the ligand binding pocket of ERα.

FIG. 10 illustrates results for testing for inhibition of $E_2$-ERα mediated induction of gene expression. Increasing the concentration of $E_2$ 500 fold has little effect on the ability of TPSF to inhibit gene expression. The potency and efficacy of 97998/TPSF was evaluated in dose-response studies of inhibition of $E_2$-ERα mediated induction of an (ERE)$_3$-luciferase reporter in stably transfected T47D cells. The cells were maintained in either 0.2 nM $E_2$ (open squares) or 100 nM $E_2$ (filled squares) and the indicated concentrations of TPSF for 24 hours prior to harvesting and assay. Data represents the average±S.E.M. of at least 3 experiments. Some error bars are smaller than the symbols. The IC$_{50}$ values of 0.4 μM (0.2 nM $E_2$) and 0.7 μM (100 nM $E_2$) were calculated by curve fitting using Sigma Plot.

We observed potent and selective inhibition of $E_2$-ERα-mediated gene expression by 97998/TPSF. We compared the ability of the compound 97998/TPSF to inhibit gene expression by ERα, glucocorticoid receptor (GR) and androgen receptor (AR). The potency and efficacy of 97998/TPSF was evaluated in dose-response studies of inhibition of $E_2$-ERα mediated induction of an (ERE)$_3$-luciferase reporter in stably transfected T47D cells and of endogenous PI-9 mRNA in MCF-7 cells. For studies of GR, we tested inhibition of dexamethasone-GR-mediated induction of an MMTV-Luciferase reporter in stably transfected T47D cells. For studies of AR, we used stably transfected HeLa cells expressing AR and a prostate specific antigen (PSA)-Luciferase reporter.

Figure 11:
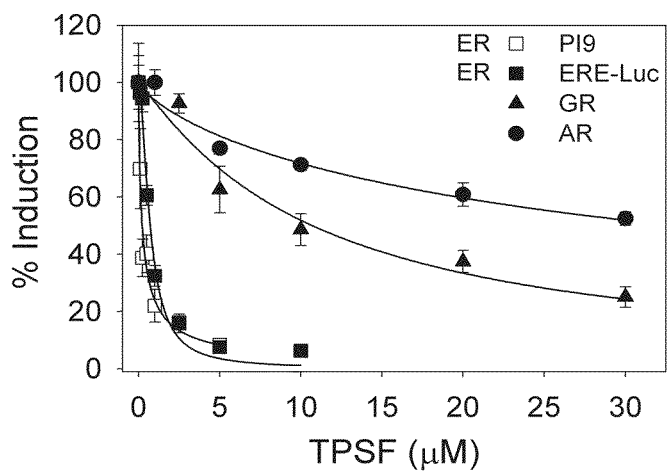
FIG. 11 illustrates results of testing for inhibition of gene expression induced by ERα, AR, and GR. Dose-response studies of inhibition by TPSF of ERα, AR and GR transactivation were performed. For each receptor, induction of reporter gene expression, or endogenous PI-9 mRNA, by its ligand with DMSO minus TPSF was >10 fold and was set to 100%. Cells were incubated for 24 h in saturating concentrations of hormones (ER: 100 nM $E_2$ and ERE-Luc reporter, filled squares; GR: 100 nM Dex and MMTV-Luc reporter, filled triangles; AR: 1 μM DHT and PSA-Luc reporter, filled circles) and the indicated concentrations of TPSF and assayed for luciferase activity. For studies of PI-9 mRNA (open squares), MCF-7 cells were incubated for 24 h with the indicated concentrations of TPSF, then maintained for 4 h in 10 nM E2 and TPSF, and PI-9 mRNA levels measured by qRT- PCR. Luciferase assays and qRT-PCR were performed as described in Materials Methods. Data are the average±SEM for at least 3 experiments. At 2.5 and 5 µM TPSF, PI-9 and (ERE)3-Luc symbols overlap and PI-9 data is not visible. Some error bars are smaller than the symbols. $IC_{50}$ values were obtained by curve-fitting using Sigma Plot and had a high R2 value. The $IC_{50}$ values observed for inhibition by TPSF were: ER genes: PI-90.2 µM; (ERE)$_3$-Luc 0.7 µM: AR: PSA-Luc 33 µM.

FIG. 11 illustrates results of testing for inhibition of gene expression induced by ERα, AR, and GR. We observed that compound 97998/TPSF is a potent and specific inhibitor of $E_2$-ERα-mediated gene expression. We performed a dose-response curve testing the ability of 97998/TPSF to inhibit induction of gene expression by ERα, AR and GR. For each receptor, induction of reporter gene expression, or endogenous PI-9 mRNA, by its ligand with DMSO minus TPSF was set to 100%. Each hormone induced gene expression >10 fold. Cells were incubated for 24 h in saturating concentrations of hormones (ER: 100 nM $E_2$, reporter, ERE-Luc, filled squares; GR: 100 nM Dex, reporter, MMTV-Luc, filled triangles; AR: 1 μM DHT, reporter, PSA-Luc, filled circles) and the indicated concentrations of 97998/TPSF, harvested, and assayed for luciferase activity. For studies of PI-9 mRNA (open squares), MCF-7 cells were incubated for 24 hours in the indicated concentrations of TPSF, then maintained for 4 hours in 10 nM $E_2$ and TPSF, harvested, and the level of PI-9 mRNA was determined. Measurement of luciferase activity and determination of PI-9 mRNA level using quantitative real-time-PCR was as described in Mao et al., 2008. Data is the average±S.E.M. of 3 experiments. Some error bars are smaller than the symbols. Data for (ERE)$_3$-Luc, and PI-9 mRNA is nearly identical at 2.5 and 5 μM TPSF and the PI-9 symbols are not visible. The IC$_{50}$ values (see Table 3) were obtained by curve-fitting using Sigma Plot.

We observed that compound 97998/TPSF is a potent inhibitor of the estrogen-dependent growth of MCF-7, human breast cancer cells, and is generally not toxic to ER negative breast cancer cells. Our assay for determination of cell growth involves using a standard curve to determine cell number, performing each assay on 8 wells of cells and using EDTA, not trypsin-EDTA, to harvest the cells. The inhibition of cell growth experiment was carried out at a concentration of $E_2$ that elicits maximum $E_2$-stimulation of MCF-7 cell growth. Compared to cells in stripped serum minus $E_2$, addition of 1 pM or 10 pM $E_2$ to the medium increases the number of cells by >5 fold after 4 d.

Figure 12:
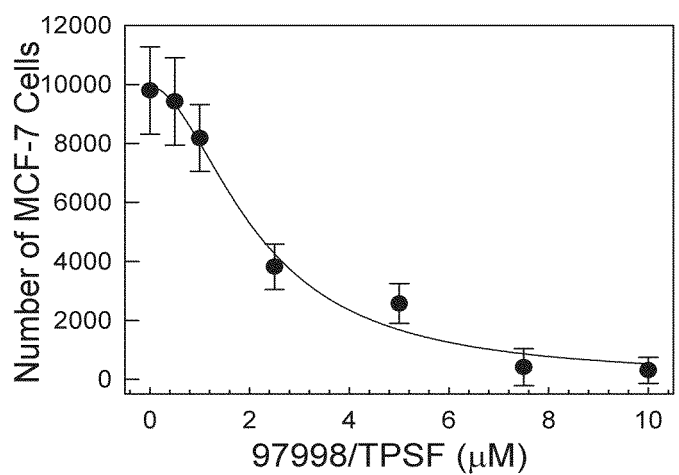
FIG. 12 illustrates the effect of compound 97998/TPSF on the growth of MCF-7 breast cancer cells. MCF-7 cells were maintained for 4 days in medium containing 5% charcoal-dextran stripped calf serum (CD-CS) and harvested. 1,000 MCF-7 cells were plated into each well of a 96 well plate in medium containing 5% CD-CS. After 24 h, the medium was changed to 5% CD-CS+1 pM $E_2$ and DMSO vehicle containing the indicated concentrations of TPSF. The medium was replaced after 2 days and the cells were assayed with MTS after 4 days. Cell number was determined using a standard curve based on plating a known number of cells and assaying the newly plated cells with the same MTS reagent used in the experiment. Each data point is the average of 8 wells±S.E.M. Data is plotted as the number of cells present after 4 days. By curve fitting in Sigma Plot, the $IC_{50}$ for inhibition of $E_2$-dependent growth of MCF-7 cells by TPSF was 2 µM.

FIG. 12 illustrates the effect of compound 97998/TPSF on the growth of MCF-7 breast cancer cells. We found that compound 97998 blocks estrogen-dependent growth of breast cancer cells. MCF-7 cells were maintained for 4 days in medium containing 5% charcoal-dextran (CD) stripped serum and harvested. A quantity of 1,000 MCF-7 cells were plated into each well of a 96 well plate in medium containing 5% CD-CS. After 24 h, the medium was changed and contained 5% CD-CS + or −1 pM $E_2$ and DMSO vehicle containing the indicated concentrations of 97998/TPSF. The medium was replaced at 2 days and the cells were assayed with MTS after 4 days. Cell number was determined using a standard curve based on plating a known number of cells and assaying the newly plated cells with the same MTS reagent used in the experiment. Each data point represents the average of 8 wells±S.E.M. The IC$_{50}$ for inhibition of $E_2$-dependent growth of MCF-7 cells by 97998/TPSF was 2 μM. The IC$_{50}$ was obtained by curve-fitting using Sigma Plot.

With the demonstration that compound 97998/TPSF effectively inhibits estrogen-dependent growth of ERα-containing MCF-7 cells (FIG. 12 and Table 3), we also evaluated it regarding toxicity. We evaluated its ability to inhibit growth of ER negative MDA-MB-231 cells in an assay format similar to the format used for the MCF-7 cells. At all concentrations tested, including 30 μM, 97998/TPSF did not inhibit growth of the MDA-MB-231 cells.

Since 97998/TPSF inhibits $E_2$-dependent growth of MCF-7 breast cancer cells with an IC$_{50}$ of 2 μM (FIG. 12), and does not inhibit growth of ER negative breast cancer cells at 30 μM, there is a concentration range between the concentrations of 97998/TPSF that effectively inhibit $E_2$-ERα-dependent breast cancer cell growth and the concentration at which it may begin to exert general toxic effects on other cells. This aspect can provide an advantageous parameter and profile for therapeutic purposes.

In embodiments the invention provides compositions and methods for modifying growth of cancer cells which are otherwise resistant to at least one chemotherapeutic agent, chemotherapy, or other cancer therapy. In embodiments the cancer cells are tamoxifen-resistant. In embodiments the cells are breast cancer cells which are tamoxifen-resistant.

Example 7

Inhibition of Growth of Human Breast Cancer Cells and Resistant Breast Cancer Cells Here we demonstrate compositions and methods relating to inhibition of cancer cells including breast cancer cells, particularly human cells, and furthermore human breast cancer cells which are resistant to tamoxifen. We also disclose that certain small molecules can act outside of the ligand binding pocket of Estrogen Receptor α to inhibit estrogen-regulated gene expression and block tamoxifen-resistant breast cancer cell growth.

Abbreviations used herein include: ERα, estrogen receptor α; E2, 17β-estradiol; FAMA, fluorescence anisotropy microplate assay; TPSF, Butyrophenone, p-fluoro-4-(1,2,3,6,-tetrahydro-1,3-dimethyl-2-oxo-6-thionopurin-8-ylthio) (TPSF is occasionally designated as compound 97998 or TPSF/97998); TPBM, 8-benzylsulfanylmethyl-1,3-dimethyl-3,7-dihydro-purine-2,6-dione; OHT, 4-hydroxytamoxifen; SERM, selective estrogen receptor modulator; EtOH, ethanol; DMSO, dimethyl sulfoxide; AR, androgen receptor; GR, glucocorticoid receptor; ERE, estrogen response element; ARE, androgen response element; IC50, Inhibitor concentration for 50% inhibition; Dox, Doxycycline; TNF, tumor necrosis factor; IL-8, interleukin 8; qRT-PCR, quantitative reverse transcriptase-PCR.

Estrogens act through estrogen receptor α (ERα) to increase the growth and metastatic potential of most human breast cancers. Despite intensive study, the mechanisms responsible for 17β-estradiol (E2) stimulated breast cancer growth, and for the development of resistance to antagonists such as tamoxifen, are not fully understood. Here we demonstrate that Butyrophenone, p-fluoro-4-(1,2,3,6,-tetrahydro-1,3-dimethyl-2-oxo-6-thionopurin-8-ylthio) (TPSF) is a potent inhibitor of ERα. TPSF acts outside the ERα ligand binding pocket and inhibits estrogen-dependent ERα-mediated gene expression. TPSF is largely ER specific and has little or no ability to inhibit the transcriptional activity of NF-κB, or the androgen receptor, or the glucocorticoid receptor. In MCF-7 cells, TPSF inhibits E2-ERα-mediated induction of the endogenous proteinase inhibitor 9 (PI-9) gene, which is activated by direct binding of ERα to estrogen response element DNA and the cyclin D1 gene which is induced by tethering of ER through proteins bound at other DNA sites. TPSF inhibits E2-ERα-stimulated growth of MCF-7 cells, but does not inhibit growth of ER-negative MDA-MB-231 cells. TPSF also inhibits ERα-dependent growth in three models of tamoxifen resistance: ERα-dependent growth of 4-hydroxytamoxifen-stimulated MCF7ERαHA cells that overexpress ERα, tamoxifen-resistant BT474 cells that contain amplified HER-2 and AIB1 and partially tamoxifen-resistant ZR-75 cells. Compounds described herein including TPSF represent a new class of ERα inhibitor that are useful in inhibiting cancer cells and therapeutic treatment of breast cancer. Such compounds also represent effective probes which are useful in the study of ERα action in tamoxifen-resistant breast cancer.

At detection, most human breast cancers are dependent on the 17β-estradiol-estrogen receptor (E2-ERα) complex. ERα, a member of the steroid/nuclear receptor family of transcription regulators is activated by E2 binding and acts in the nucleus to regulate gene expression by direct binding to estrogen response elements (EREs) and related DNA sequences and through its association with transcription factors bound to DNA at SP1 and AP-1 sites. Upon binding to a potent estrogen, the ER dimerizes, stimulating binding to ERE DNAs and undergoes a conformational change in the ligand binding domain that facilitates the recruitment of coactivators. The bound coactivators help promote assembly of a multiprotein complex that enables chromatin remodeling and stabilization of an active transcription complex. In contrast, antagonist occupied ERα recruits corepressors. ERα also acts outside the cell nucleus to influence the activity of signal transduction pathways. Activation of the ERK1/2 signal transduction pathway by E2-ERα may contribute to the growth of some breast cancers.

Treatment strategies for estrogen-dependent breast cancer include selective estrogen receptor modulators, such as tamoxifen, that bind in the ERα ligand binding pocket, and aromatase inhibitors that block estrogen production. However, the long-term usefulness of tamoxifen is limited by the development of resistance in nearly all patients with metastatic breast cancer and in ~40% of patients with primary breast cancers. Recent studies indicate that nearly half of the patients treated with aromatase inhibitors develop resistance to the aromatase inhibitors. The development of resistance to tamoxifen and aromatase inhibitors underscores the need for new approaches of compositions and methods for inhibition of cancer cells and therapeutic benefit. These approaches can include small molecule antagonists that act outside the ligand binding pocket of ERα. We recently described a high throughput screening strategy to identify small molecule inhibitors that target ERα binding to DNA. We identified 8-Benzylsulfanylmethyl-1,3-dimethyl-3,7-dihydro-purine-2,6-dione (TPBM/95910) as a small molecule inhibitor of ERα binding to ERE DNA (Mao C et al., 2008, J Biol Chem 283:12819-30). We evaluated ~200 small molecules structurally related to TPBM, to identify Butyrophenone, p-fluoro-4-(1,2,3,6,-tetrahydro-1,3-dimethyl-2-oxo-6-thionopurin-8-ylthio) (TPSF), a novel ERα inhibitor. TPSF is a >15-fold more potent second-generation inhibitor of ERα. TPSF specifically inhibits E2-ERα-mediated gene expression, E2-ERα stimulated growth of Tam-sensitive MCF-7 cells and Tam-resistant breast cancer cell lines, but TPSF does not inhibit growth of ERα-negative MDA-MB-231 breast cancer cells, indicating that it does not exert a general toxic effect on cells.

Results

As an overview, we demonstrate that certain compounds and methods are useful in the inhibition of cancer cells, particularly human breast cancer cells and resistant varieties thereof. Compounds and methods herein are able to be used in therapeutic applications in the treatment of cancer including human breast cancer.

TPSF is an inhibitor of ERα. Further, we show that this compound acts outside of the ligand binding pocket of the receptor. The compound designated NSC 99676 is also useful.

We screened ~200 small molecules structurally related to our recently reported ERα inhibitor, TPBM/95910 (Mao C et al., 2008, J Biol Chem 283:12819-30). We evaluated the ability of each compound to inhibit E2-ERα-mediated gene expression in ERα-positive T47D-KBluc human breast cancer cells that stably express an (ERE)3-luciferase reporter gene. We identified compound TPSF/97998, a much more potent inhibitor of ERα than TPBM, and compound NSC 99676, with structures below.

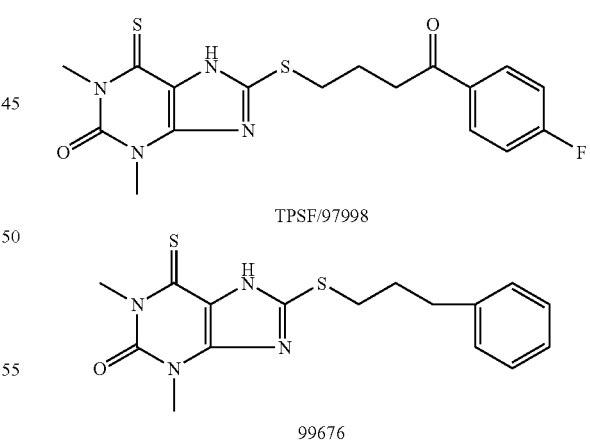

Figure 13:
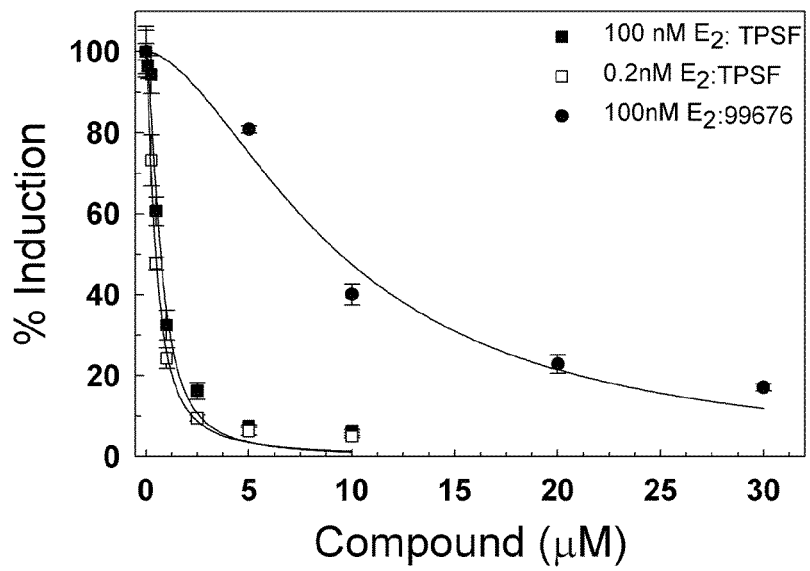
FIG. 13 illustrates results from evaluation of the potency and efficacy of TPSF and 99676. Compounds were evaluated in dose-response studies of T47D (ERE)$_3$-Luc cells maintained in either 0.2 nM E2 (open squares) or 100 nM (filled squares) and the indicated concentrations of TPSF or 99676 (filled circles) for 24 hours prior to assay. Data is the average of 3 experiments±SEM. Some symbols overlap and some error bars are smaller than the symbols. $IC_{50}$ was calculated by curve fitting using Sigma Plot. Data for TPSF (see FIG. 10) is shown with that for 99676.

Dose-response studies performed under identical conditions demonstrated inhibition of E2-ERα-mediated expression of the (ERE)3-luciferase reporter gene in T47D cells with an $IC_{50}$ of 11 μM for TPBM (see Mao C et al., 2008) and 0.4 μM for TPSF (FIG. 13).

To determine whether TPSF acts outside of the ligand binding pocket of ERα, we varied the E2 concentration by 500 fold and tested the ability of TPSF to inhibit expression of the stably transfected (ERE)3-luciferase reporter gene in T47D cells. If TPSF was inhibiting ERα by binding in the ligand binding pocket of the receptor, increasing the concentration of E2 should compete with TPSF and block inhibition. Increasing the concentration of E2 from 0.2 nM to 100 nM barely increased the IC50 for inhibiting E2-ERα-mediated transcription (from 0.4 µM to 0.7 µM, FIG. 13). These results indicate that TPSF acts outside the ERα ligand binding pocket.

TPSF differs from NSC 99676 by having hydrophilic C=O and F substitutions at the phenyl ring. TPSF inhibited ERα-mediated gene expression with an IC50 of 0.7 µM. Compound 99676, which is similar to but more hydrophobic than TPSF, had an $IC_{50}$ of 9 µM and was ~13 fold less potent than TPSF (FIG. 13). Thus, TPSF is a structure-specific inhibitor of ERα in the sense that it has measurably greater activity than a compound with another structure; however, other compounds as described according to the disclosure herein also can be useful.

TPSF is a Specific Inhibitor of Transactivation by ER.

Figures 14, 15:
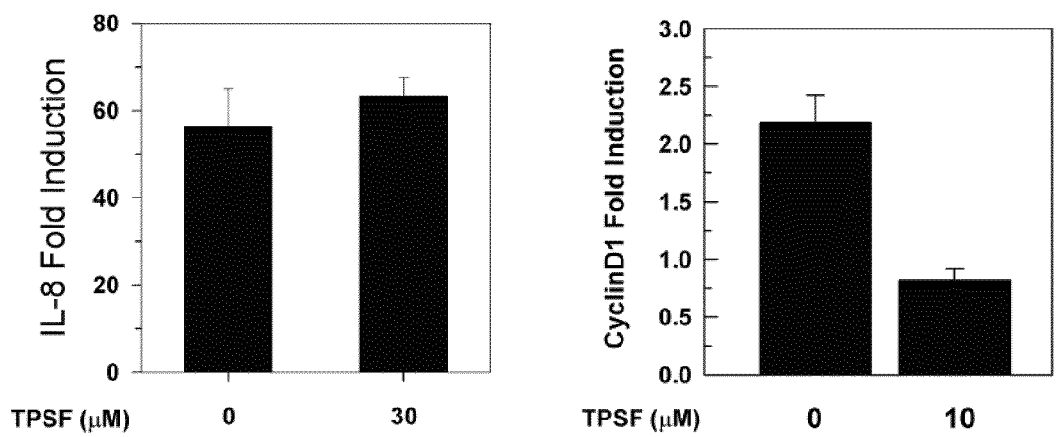
FIG. 14 illustrates results of testing for specific inhibition of $E_2$-ERα-mediated gene expression. The effects of TPSF on an NF-κB regulated gene, IL-8, were tested in MCF-7 cells maintained for 24 hours in medium containing 10 ng/ml TNF-α alone or TNF-α and 30 µM TPSF. RNA was extracted and IL-8 mRNA levels were measured by quantitative (q)RT-PCR. Data shown is the average of 3 experiments±SEM.
FIG. 15 illustrates results of testing for inhibition of the estrogen induction of Cyclin D1 mRNA. MCF-7 cells were plated and 24 h later treated with ethanol vehicle, 10 nM $E_2$, or 10 nM $E_2$ and 10 µM TPSF. Cells were maintained for 24 hours, RNA was extracted and cyclin D1 mRNA levels were measured by qRT-PCR. Cyclin D1 mRNA levels in the vehicle only sample were set to 1. Data is the average±SEM for 3 experiments each assayed in triplicate.

To test the specificity of TPSF for ERα, we used MCF-7 cells to compare its ability to inhibit expression of the E2-ERα-inducible proteinase inhibitor 9 (PI-9) gene and the NF-κB inducible IL-8 gene. The estrogen-inducible serpin PI-9 is a tumor lethality factor. Estrogen induction of PI-9 enables breast cancer cells to evade apoptosis induced by the immune cells, cytotoxic T lymphocytes (CTLs) and natural killer (NK) cells and inhibits TNF-α, Fas and TRAIL mediated apoptosis. Expression of PI-9 is regulated by direct binding of E2-ERα to EREs and ERE half sites. We chose an NF-κB-regulated gene as a control because many regulators and pathways including IκB and other kinases, acetylases, the ubiquitin/proteasome pathway and nuclear/cytoplasmic shuttling all influence NF-κB activity. Therefore, analyzing the effect of TPSF on NF-κB is a good way to test whether TPSF acts as a promiscuous inhibitor targeting diverse cell proteins and pathways. 30 µM TPSF had no effect on the NF-κB-mediated induction of IL-8 mRNA by TNF-α (FIG. 14). Thus, in the same breast cancer cells in which TPSF inhibited $E_2$-ERα induction of PI-9 mRNA ($IC_{50}$ of 0.2 µM) (FIG. 11), a >100 fold higher concentration of TPSF, 30 µM, had no effect on NF-κB induction of a responsive gene (FIG. 14).

While these data indicated that TPSF was not a promiscuous inhibitor influencing pathways unrelated to ERα action, as a further test of the specificity of TPSF for ERα we used other steroid receptors. We tested the specificity of TPSF for $E_2$-ERα-induced gene expression using both the endogenous PI-9 mRNA in MCF-7 cells (FIG. 11) and the stably transfected T47D (ERE)3-Luc cells. We examined inhibition of dexamethasone dependent GR-mediated induction of an MMTVLuciferase reporter in stably transfected T47D cells, and a prostate specific antigen (PSA)-luciferase reporter in stably transfected HeLa cells expressing AR. TPSF inhibited E2-ERα-induced gene expression (IC50s 0.2 µM for endogenous PI-9 in MCF-7 cells and 0.7 µM for (ERE)3-Luc in T47D cells (FIG. 11)). Concentrations of TPSF necessary to inhibit AR (IC50 33 µM) and GR (IC50 10 µM) are 20-70 fold higher than the 0.45 µM average IC50 for inhibition of the two ER-regulated genes (FIG. 11). The results indicate that TPSF is a specific inhibitor of ERα.

TPSF Inhibits Estrogen Induction of Cyclin D1.

Estradiol stimulation of the cell cycle progression factor, cyclin D1, is thought to contribute to the growth of MCF-7 and other breast cancer cells. Cyclin D1 is also thought to play a role in tamoxifen-stimulated growth of breast cancer cells. To examine the ability of TPSF to inhibit E2-ERα induction of a gene that is regulated by tethering of E2-ERα through DNA bound transcriptional regulators, we tested the effect of TPSF on induction of cyclin D1 mRNA. E2-ERα only stimulated a 2-3 fold increase in cyclin D1 mRNA, which was completely inhibited by 10 µM TPSF (FIG. 15). Taken together, the data demonstrate that TPSF inhibits estrogen dependent gene expression through mechanisms that include direct binding of ERα to EREs and related sequences, as shown for ERE-Luc and PI-9 and tethering of ERα to DNA through DNA-associated transcription regulators, as shown for cyclin D1.

TPSF Inhibits Estrogen-Dependent Growth of MCF-7 Cells and is Less Toxic to ER-Negative MDA-MB-231 Cells than 4-Hydroxytamoxifen.

Figure 16:
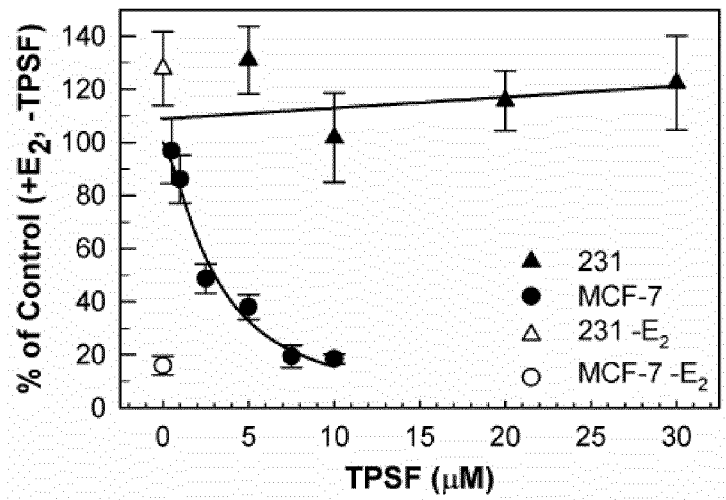
FIG. 16 illustrates results of studying the specific inhibition of estrogen-dependent breast cancer cell growth by TPSF. MCF-7 and MDA-MB-231 cells were maintained for 4 days in 5% CD-CS, harvested and 1,000 MCF-7 cells (circles) or MDA-MB-231 cells (triangles) were plated per well in 96 well plates in 5% CD-CS. After 24 h, the medium was changed to 5% CD-CS with 1 pM $E_2$ (filled circles or triangles) or without $E_2$ (open circle and open triangle) and DMSO vehicle and the indicated concentrations of TPSF. This concentration of $E_2$ elicits maximum $E_2$-stimulation of MCF-7 cell growth. Medium was replaced at 2 days and cells were assayed with MTS after 4 days. Cell number was determined using a standard curve based on plating a known number of cells and assaying the cells with MTS. Each data point is the average of 8 wells±SEM. Data are plotted as a percentage of the number of each type of cell present after 4 days with $E_2$ and without TPSF set as 100. By curve fitting in Sigma Plot, the IC50 for inhibition of $E_2$-dependent growth of MCF-7 cells by TPSF was 2 µM. Similar inhibition of growth by TPSF was obtained with MCF-7 cells in 10 pM $E_2$.

To determine whether TPSF specifically inhibited ERα-dependent growth of breast cancer cells with minimal cell toxicity, we tested TPSF inhibition of cell growth in MCF-7 cells and in ER negative MDA-MB-231 human breast cancer cells. Compared to MCF-7 cells in estrogen-depleted medium, 1 pM or 10 pM E2 stimulates a 4-5 fold increase in cell number after 4 days. TPSF inhibited estrogen-dependent growth of MCF-7 cells with an IC50 of 2 µM, completely blocked E2-dependent growth at 7.5 µM (FIG. 16, filled circles) and did not inhibit E2-independent cell growth (compare 7.5 and 10 µM, filled circles to no E2 and no TPSF, open circle). In ER negative MDA-MB-231 cells, TPSF did not inhibit growth at all concentrations, including 30 µM (FIG. 16, filled triangles). Thus, there is a large concentration "window" between the concentrations of TPSF that effectively inhibit E2-ERα-dependent breast cancer cell growth ($IC_{50}$ 2 µM) and the concentration (>30 µM) at which it may begin to exert general toxic effects on cells.

Figure 17:
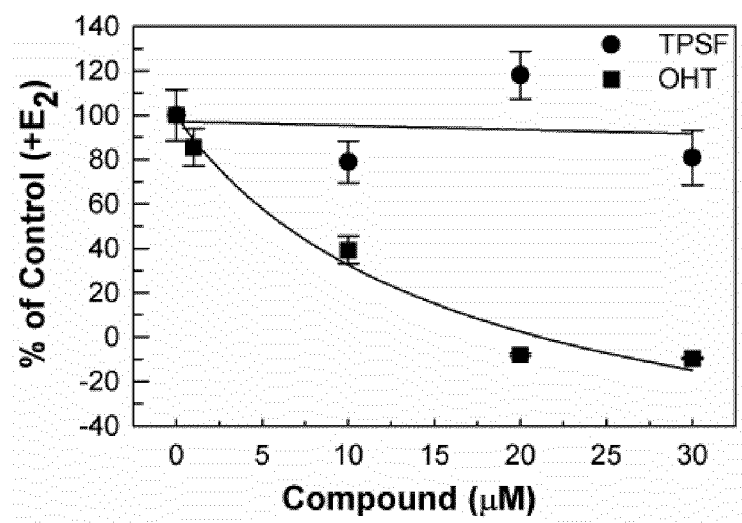
FIG. 17 illustrates results from studying toxicity of TPSF in ER negative MDA-MB-231 cells. Cell maintenance, growth and plating were as described in the Materials and Methods. The indicated concentrations of OHT (filled squares) and TPSF (filled circles) were added to the cells and cell number determined using MTS and a standard curve (See FIG. 16). Data were the average of 3 experiments±SEM.

To compare the toxicity of TPSF to 4-hydroxytamoxifen (OHT), the active form of the widely used ER-antagonist tamoxifen, and to rule out the possibility that MDA-MB-231 cells are unusually resistant to the toxic effects of TPSF and other ERα inhibitors, we compared the effects of TPSF and OHT on MDA-MB-231 growth. At 10 µM, OHT killed many of the MDA-MB-231 cells and all the cells were killed at 20 µM OHT. In contrast, TPSF did not inhibit MDA-MB-231 cell growth, even at 30 µM (FIG. 17). At 10-20 µM concentrations, tamoxifen, OHT and raloxifene, induce caspase-dependent apoptosis in ER negative HeLa cells. Thus, we observe that TPSF is less toxic than widely used SERMs. This reduced toxicity aspect makes the compound more useful for therapeutic purposes.

TPSF Inhibits E2 and OHT-Induced Gene Expression in Tamoxifen-Stimulated MCF7ERαHA Cells The development of resistance to tamoxifen, and other therapeutics that target ERα and estrogen production is a significant problem in both primary and metastatic disease. Tamoxifen-resistant breast cancer cells that retain dependence on ERα for growth lose their dependence on SRC3 and other p160 coactivators for E2-ERα mediated gene transcription. We explored the ability of TPSF to inhibit E2 and OHT-dependent gene expression in Tam-resistant cells that are less dependent on p160 coactivators for transactivation.

MCF7ERαHA cells are an MCF-7-derived model for Tam-resistant breast cancer in which doxycycline (Dox) increases overexpression of ERα, resulting in resistance to tamoxifen. In these cells, tamoxifen and 4-hydroxytamoxifen (OHT) are potent ERα agonists that increase ERα-mediated gene expression independent of SRC3. Because OHT stabilizes ERα against degradation, while E2-down-regulates ERα, ERα levels are ~4 times higher in OHT treated MCF7ERαHA cells than in MCF7ERαHA cells treated with E2. The elevated level of ERα in OHT-treated MCF7ERαHA cells compared to cells treated with E2 renders OHT more effective than E2 in inducing PI-9 gene expression and more difficult to inhibit. 10 μM TPSF blocked E2-mediated induction of PI-9 mRNA and the ~700 fold OHT-ERA induction of PI-9 mRNA (FIG. 18, OHT). Thus, TPSF is an inhibitor of both E2-ERα and OHT-ERA mediated gene expression in cells where tamoxifen is a full agonist. TPSF therefore represents a useful new tool for analyzing ERα action in tamoxifen-resistant cells.

TPSF Inhibits E2-ERα-Dependent Growth of Tamoxifen-Resistant MCF7ERαHA Cells

Some Tam-resistant breast cancers regress after Tam withdrawal, suggesting Tam stimulates tumor growth. MCF7ERαHA cells, in which Tam and OHT are full agonists (FIG. 18) are a model for tamoxifen-stimulated breast cancer. In MCF7ERαHA cells treated with Dox, overexpression of ERα results in an increase in E2-independent ERα-mediated cell growth which was further increased by 1 pM E2 and by the addition of 5 μM OHT (FIG. 19). E2-ERα-dependent growth of MCF7ERαHA cells was inhibited by 5 μM TPSF (FIG. 19). Thus, TPSF is effective in a model for Tam resistance in which overexpression of ERα results in OHT-stimulated cell growth.

TPSF Inhibits E2-ER-dependent Growth of Tamoxifen-Resistant BT474 and ZR-75 Human Breast Cancer Cells The ability of TPSF to inhibit E2-ERα-dependent growth was tested in two additional human cell models for tamoxifen-resistant breast cancer. ZR-75 cells are usually reported as partially Tam and OHT-resistant, while BT474 cells are fully Tam-resistant and exhibit amplified expression of HER2 and AIB1. TPSF inhibited E2-ERα-dependent growth of BT474 and ZR-75 cell lines with close to maximal inhibition at 5 μM (FIG. 20). Since TPSF is not toxic, cell numbers after TPSF treatment are not zero and represent cells plated at day zero plus E2-ERα-independent cell growth over the four days. $IC_{50}$ values (see FIG. 20) were 0.9 μM for the slow-growing ZR-75 cells and 1.6 μM for BT474 cells. The lower levels of ERα in ZR-75 compared to MCF-7 cells may be responsible for the greater potency of TPSF. TPSF inhibits $E_2$-ERα-dependent growth, but does not kill cells. Although it is almost certain that some portion of ZR-75 cell growth is ERα-independent, to calculate the $IC_{50}$ using Sigma Plot, we use the very conservative assumption that all cell growth beyond the 2,000 ZR-75 cells plated is $E_2$-ERα-dependent growth and potentially subject to inhibition by TPSF. Table 4 summarizes the effect of TPSF on gene expression and cell growth. In Table 4, data are shown from dose-response curves for inhibition of $E_2$-ERα-mediated breast cancer gene expression and cell growth. Experimental details are provided in the Materials and Methods below. Dose response curves were performed as described elsewhere herein (see Figures for this Example). $IC_{50}$ values were calculated by curve fitting using Sigma Plot.

TABLE 4

$IC_{50}$ Values (μM) for Inhibition by Compound TPSF of E2-ERα Dependent Gene Activation and Growth of ER Positive and ER Negative Breast Cancer Cells

| Gene Exp. ERE-Luc, Endog. PI-9 | Gene Exp. AR, GR, NF-κB | MCF-7, ZR-75, BT474 Cell Growth (ER. Pos. cells) | MDA-MB-231 Cell Growth (ER Neg. cells) |
|---|---|---|---|
| 0.7, 0.2 | 34, 10, >>30 | 2.0, 0.9, 1.6 | >30 (0% in.) |

Discussion

Generally, a small molecule inhibitor useful in breast cancer will exhibit specificity for ERα and low nonspecific toxicity. Based on our work, independent testing of TPSF against a panel of 60 cancer cell lines at the NCI Developmental Therapeutics Program showed that TPSF does not inhibit growth of a diverse set of cell lines. Because 10 μM TPSF did not inhibit the growth of at least 9 of the 60 cell lines by 40%, TPSF was not subjected to second tier testing by this evaluation program.

Our data indicate that TPSF selectively targets E2-ERα-dependent cell growth without broad inhibition of ERα-independent cell growth. At the end of 4 days, E2 increased MCF-7 cell number by ~4 fold, which corresponded to a doubling time of ~1 day with E2 and 2 days without E2. However, TPSF did not kill all the cells, and the number of cells in wells treated with 7.5 μM and 10 μM TPSF was similar to the cell number seen without added E2. Our studies using ER-negative MDA-MB-231 cells showed that TPSF lacks toxicity, even at 30 μM.

TPSF's lack of nonspecific toxicity contrasts with the widely used estrogen antagonists. Tamoxifen is effective in the management of ERα positive breast cancers and has proven to have low toxicity in clinical practice. At the cell level, TPSF is even less toxic than the active form of tamoxifen, OHT. Tamoxifen also exhibits cell type selective ERα agonist activity.

Several lines of evidence support the considerable specificity of TPSF for ERα. NF-κB is regulated by a variety of signaling mechanisms including the ubiquitin/proteasome pathway, nuclear/cytoplasmic shuttling, IκB and other kinases and acetylases. Thus, analyzing the effect of TPSF on NF-κB is a good way to test its specificity. TNF-α activation of NF-κB in MCF-7 cells increases IL-8 mRNA levels by ~50 fold making it possible to use qRT-PCR to identify modest effects of TPSF on NF-κB induction of IL-8 mRNA. The absence of an effect of 30 μM TPSF on TNF-α induction of IL-8 mRNA, indicated that TPSF does not exhibit nonspecific effects on these diverse cell pathways. Compound NSC-99676, which is structurally similar to TPSF, was ~13 times less potent as an inhibitor of ERα than TPSF. While 99676 has lower relative potency as measured here, it nonetheless can be useful in ways similar to TPSF. TPSF specificity for ERα was also demonstrated relative to other steroid receptors. TPSF is a much more potent inhibitor of transactivation by ERα compared to AR or GR. Since we identified other compounds that inhibit AR and GR under the same assay conditions, the failure of low concentrations of TPSF to inhibit transactivation by AR and GR is not due to assay conditions that mask inhibition.

The recent identification of a new coactivator binding surface on AR using moderate potency (IC50 ~50 μM) small molecule inhibitors of AR that were selected by high throughput screening (see Estebanez-Perpina 2007) further supports the idea that small molecules are useful as probes for understanding the mechanisms of steroid receptor action. These AR inhibitors are unrelated to TPSF.

ERα activates gene expression by direct binding to ERE-related DNA sequences and by tethering to DNA associated transcription factors. Our studies indicate that both of these mechanisms are inhibited by TPSF. TPSF inhibited the induction of PI-9 mRNA by PI-9 E2-ERα and by OHT-ERA. PI-9 gene expression is induced by E2-ERα binding to two adjacent ER binding sites in the PI-9 promoter region. Because PI-9 inhibits granzyme B and CTL and NK cell mediated apoptosis of target cancer cells, and caspase 8-dependent apoptosis induced by TNF-family members, and its expression is associated with a poor prognosis in some cancers, induction of PI-9 may be a mechanism by which estrogens enable breast cancers to evade immune surveillance and apoptosis. Cyclin D1 plays a key role in cell cycle progression and is induced by tethering of E2-ERα at transcription factors bound at SP1 sites. Cyclin D1 induction is proposed to play a role in estrogen-dependent growth of breast cancer cells. Consistent with its role as an ER inhibitor, 10 μM TPSF abolished E2 induction of cyclin D1 mRNA, but did not reduce the level of cyclin D1 mRNA much below the basal (-E2) level. Since 10 μM TPSF also abolished E2-ERα-dependent growth of MCF-7 cells, these data indicate a role for cyclin D1 in estrogen-stimulated growth of breast cancer cells. Our work using small molecule inhibition is important and differs from the RNAi knockdown technique where a nearly complete loss of cyclin D1 expression reduced growth of MCF-7 cells in medium containing estrogen (see Grillo et al., 2006). Because TPSF targets only the ERα-regulated component of the expression of ERα target genes without influencing their basal expression, it represents a useful probe to help clarify the precise role of ERα regulation of specific genes in growth and migration of breast cancer cells.

Development of resistance to tamoxifen and other endocrine therapies represents a major problem in the treatment of breast cancer. A therapeutically useful small molecule inhibitor of ER should inhibit growth of the primary tumor that may be sensitive to inhibition by tamoxifen and OHT, but also it is desirable to inhibit growth of tumor cells that acquire resistance to agents including tamoxifen and OHT. Tamoxifen-resistant tumors fall into three broad classes. Some tumors become independent of ERα for growth and are unaffected by therapies that target ERα. Others tumors remain dependent on E2 and ERα for growth, whereas a third group of tumors lose estrogen-dependence but require ERα for growth. One simple mechanism for tumor resistance to antagonists is overexpression of steroid receptors. Overexpression of AR is the predominant mechanism of resistance to endocrine therapy in recurrent prostate cancer. A subset of breast cancers also contain high levels of ERα and are often refractory to tamoxifen therapy. In MCF7ERαHA cells that overexpress ERα, tamoxifen and OHT are full agonists and induce PI-9 expression. In MCF7ERαHA cells maintained in the presence of OHT, levels of ERα are >10 times higher than in wild-type MCF-7 cells maintained in E2 (Mao C et al., 2008). In cells expressing high levels of ERα, 10 μM TPSF inhibited both E2-ERα and OHT-ERA induction of PI-9.

While the mechanisms involved in resistance to endocrine therapy are diverse, the p160 coactivators do not appear to be central to ERα transactivation in tamoxifen-resistant cell lines and the identity of the coactivators responsible for ERα transactivation are unknown. Our initial lead compound, TPBM acts in cells by inhibiting ERα binding to regulatory regions in estrogen-responsive genes (Mao C et al., 2008). The present study has identified a TPBM-related compound, TPSF, which is >15-fold more potent than TPBM. It remains to be established whether TPSF inhibition of ER-dependent growth in tamoxifen resistant cells involves inhibition of coactivator recruitment.

Primary live cell samples of tamoxifen-resistant metastatic breast cancer are largely unavailable. Because sites of metastasis of tamoxifen-resistant tumors are well known, and the tumors usually cannot be surgically removed, it is now considered unethical to routinely biopsy tumors at these sites (see Abukhdier A M et al., 2008). We and others (see Wang et al., 2006) have therefore evaluated ER inhibitors using stable breast cancer cell lines that are resistant to tamoxifen. ZR-75 breast cancer cells are slow growing, partially resistant to tamoxifen and OHT, and are only weakly stimulated by E2. TPSF inhibited E2-dependent growth of ZR-75 cells (IC50 0.9 μM). MCF7ERαHA cells are representative of cells that are tamoxifen-resistant cells because they overexpress ERα and growth of these cells is modestly stimulated by 5 μM OHT. In contrast to OHT, TPSF blocked the growth of MCF7ERαHA cells. BT474 cells are fully Tam resistant in cell culture and in xenograft studies and contain amplified HER2 and AIB1. TPSF inhibited E2-ERα-dependent growth of BT474 cells. Thus, TPSF is effective in cells that become tamoxifen-resistant through different mechanisms. In addition to the benefit of strong inhibition regardless of the mechanism, this mechanistic attribute allows us to probe tamoxifen-resistance in multiple models.

TPSF is structurally distinct from disulfide benzamide (DIBA), a zinc chelator that acts outside the ERα ligand binding pocket. DIBA promotes an ERα conformation conducive to the antagonist activity of OHT in tamoxifen-resistant cell lines. However, 5 μM DIBA inhibited growth of ZR-75 cells by ~20% and did not inhibit the growth of tamoxifen-resistant BT474 cells (see Wang 2006), whereas growth of ZR-75 cells and BT474 cells was inhibited by TPSF (IC50s 0.9 and 1.6 μM. respectively).

In conclusion, potent and specific small molecule inhibitors of ERα have been identified. Particularly, the compound TPSF blocks ERα-mediated gene expression and estrogen dependent growth of breast cancer cells that are resistant to tamoxifen. Because of the discoveries herein, there is a research contribution directed to the further probing of underlying mechanisms of ER action. Of considerable significance in the context of cancer, inhibitors as described herein including TPSF represent a new class of compounds which are useful in applications such as the inhibition of cancer cells and for the treatment of breast cancer.

Materials and Methods

Cell Culture. Cell lines were maintained in growth medium containing serum that was not stripped with charcoal-dextran (CD) and switched to phenol-red free medium containing CD-treated serum at least 3 days prior to treatment with E2, OHT or TPSF. ERα positive MCF-7, human breast cancer cells and ER-negative MDA-MB-231 breast cancer cells were routinely cultured in MEM supplemented with 10% calf serum at 37° C. in 5% CO2 and switched to MEM containing 5% CD-treated calf serum 3 or 4 days before the experiment. The medium was changed on day 2. Tet-inducible MCF7ERαHA cells were maintained at 37° C. in 10% CO2 in DMEM supplemented with 1 mM sodium pyruvate, 0.5 μg/ml puromycin and 10% FBS. Four days before the experiment, MCF7ERαHA cells were switched to the above medium without phenol red containing 10% 6 times CD-treated FBS, no puromycin and grown in 5% CO2 as described (see references 26, 27, 40, 42). ZR-75 breast cancer cells were maintained at 37° C. in 5% CO2 in MEM containing 10% calf serum and switched to medium containing 10% CD-CS 4 days before the experiment. BT474 cells were maintained at 37° C. in 5% CO2 in improved MEM (iMEM) containing 10% FBS and switched to phenol red-free iMEM containing 10% CD-FBS 4 days before the experiment. T47D-KBluc breast cancer cells expressing an (ERE)3-luciferase reporter gene (see reference 20) were maintained in phenol red-free RPMI 1640 with 2 mM L-glutamine, 1.5 g/l sodium bicarbonate, 4.5 g/l glucose, 10 mM Hepes, pH 7.5, 1 mM sodium pyruvate, 10% FBS (Atlanta Biological, Atlanta, Ga.) and antibiotics. Four days before E2 induction, the cells were switched to the above medium without phenol red, with 10% 2 times CD calf serum instead of FBS. T47D/A1-2 cells stably transfected to express GR and an MMTV-luciferase reporter (32) were maintained in MEM supplemented with 10 mM HEPES, pH 7.4 and 2 mM glutamine and 5% FBS and 200 μg/ml G418. Four days before the experiment the cells were switched to the above medium (phenol red-free) containing 10% 2 times CD-calf serum. HeLa cells stably transfected to express AR and a PSA-luciferase reporter were maintained in phenol-red free MEM supplemented with 2 mM L-glutamine, 1 mM sodium pyruvate, 10% FBS and maintained under selection with 100 μg/ml hygromycin and 500 μg/ml G418. Four days before the experiment they were switched to the above medium containing 10% 2 times CD calf serum.

Reporter Gene Assays. TPSF was identified by reporter gene assays comparing the ability of ~200 compounds structurally related to TPBM (see reference 19) to inhibit transcription of a stably transfected (ERE)3-luciferase reporter gene in T47D-KBluc breast cancer cells (20). AR was assayed in stably transfected HeLa cells and GR was assayed in stably transfected T47D cells maintained as described above. Four days before each experiment the cells were switched to medium containing CD-treated serum as described above. The HeLaAR cells were plated at 100,000 cells/well and the T47D/A1-2 and T47D-KBluc cells were plated at 200,000 cells/well in 1 ml of their respective media in 24-well plates. After 24 hours the indicated concentrations of E2, dihydrotestosterone (DHT) or dexamethasone (Dex) and DMSO vehicle, with or without TPSF, were added to each well. After 24 hours, the cells were washed once in phosphate buffered saline and lysed using 100 μl of 1× Passive Lysis Buffer (Promega, Madison Wis.). Luciferase activity was determined using BrightGlo firefly luciferase reagent from Promega (Madison, Wis.).

Endogenous Gene Expression. MCF-7 cells or MCF7ERαHA cells were maintained for 4 days in medium containing 5% CD calf serum (MCF-7 cells) or 10% 6×CD-FBS (MCF7ERαHA cells). In assays of TPSF inhibition of PI-9 induction, cells were plated, incubated for 24 hours in the indicated concentrations of TPSF and then maintained 4 hours with and without E2, with and without TPSF. To induce ERα, MCF7ERαHA cells were also maintained in 0.5 μg/ml Dox for 24 hours prior to addition of E2 or OHT with or without TPSF. For induction of cyclin D1, 24 hours after plating the cells, E2 with and without TPSF was added, the cells were maintained for 24 hours, RNA was extracted and mRNA levels were determined by quantitative RT-PCR as described (19, 26). Actin mRNA levels were used as the qRT-PCR internal standard. The primers and sequences used in qRT-PCR were as follows.

```
Cyclin D1:
                                   (SEQ ID NO: 4)
Forward: 5'-TCATGGCTGAAGTCACCTCTTGGT-3',
                                   (SEQ ID NO: 5)
Reverse: 5'-TCCACTGGATGGTTTGTCACTGGA-3';

PI-9:
                                   (SEQ ID NO: 6)
Forward: 5'-TGGAATGAACCGTTTGACGAA-3',
                                   (SEQ ID NO: 7)
Reverse: 5'-CATCTGCACTGGCCTTTGCT-3';

IL-8:
                                   (SEQ ID NO: 8)
Forward: 5'-GAGGGTTGTGGAGAAGTTTTTG-3',
                                   (SEQ ID NO: 9)
Reverse: 5'-CTGGCATCTTCACTGATTCTT G-3';

β-actin:
                                   (SEQ ID NO: 10)
Forward: 5'-AAGCCACCCCACTTCTCTCTAA-3',
                                   (SEQ ID NO: 11)
Reverse: 5'-AATGCTATCACCTCCCCTGTGT-3'.
```

Assays for Cell Growth and Viability. Cells were maintained in the media listed above containing CD-treated serum for at least 4 days prior to the experiment. To minimize cell aggregation, MCF-7 cells were harvested in 10 mM Hepes, pH 7.4, 1 mM EDTA. Other cell lines were harvested in trypsin-EDTA. 1,000 cells were plated into each well of a 96 well plate. For slow growing ZR-75 cells, 2,000 cells were plated/well. The cells were maintained in medium containing CD-treated serum for 24 hours. At 24 hours the medium was changed and E2 and DMSO vehicle or TPSF in DMSO was added. The medium was replaced after 2 days (except for BT474 cells whose medium was not changed). After 4 days viable cells were determined using a cell viability test, Promega CellTiter 96 Aqueous One Solution Cell Proliferation Assay (MTS) (Promega, Wis.).

REFERENCES

1. Henderson B E, Feigelson H S 2000 Hormonal carcinogenesis. Carcinogenesis 21:427-33
2. Deroo B J, Korach K S 2006 Estrogen receptors and human disease. J Clin Invest 116:561-70
3. Fabian C J, Kimler B F 2005 Selective estrogen-receptor modulators for primaryprevention of breast cancer. J Clin Oncol 23:1644-55
4. Katzenellenbogen B S, Montano M M, Ekena K, Herman M E, McInerney E M 1997 William L. McGuire Memorial Lecture. Antiestrogens: mechanisms of action and resistance in breast cancer. Breast Cancer Res Treat 44:23-38
5. O'Lone R, Frith M C, Karlsson E K, Hansen U 2004 Genomic targets of nuclear estrogen receptors. Mol Endocrinol 18:1859-75
6. Carroll J S, Brown M 2006 Estrogen receptor target gene: an evolving concept. Mol Endocrinol 20:1707-14
7. Carroll J S, Liu X S, Brodsky A S, Li W, Meyer C A, Szary A J, Eeckhoute J, Shao W, Hestermann E V, Geistlinger T R, Fox E A, Silver P A, Brown M 2005 Chromosome-wide mapping of estrogen receptor binding reveals long-range regulation requiring the forkhead protein FoxA1. Cell 122: 33-43
8. Jakacka M, Ito M, Weiss J, Chien P Y, Gehm B D, Jameson J L 2001 Estrogen receptor binding to DNA is not required for its activity through the nonclassical AP1 pathway. J Biol Chem 276:13615-21
9. Safe S 2001 Transcriptional activation of genes by 17 beta-estradiol through estrogen receptor-Sp1 interactions. Vitam Horm 62:231-52
10. Kushner P J, Agard D A, Greene G L, Scanlan T S, Shiau A K, Uht R M, Webb P 2000 Estrogen receptor pathways to AP-1. J Steroid Biochem Mol Biol 74:311-7
11. Qin C, Singh P, Safe S 1999 Transcriptional activation of insulin-like growth factorbinding protein-4 by 17beta-estradiol in MCF-7 cells: role of estrogen receptor-Sp1 complexes. Endocrinology 140:2501-8
12. Shiau A K, Barstad D, Loria P M, Cheng L, Kushner P J, Agard D A, Greene G L 1998 The structural basis of estrogen receptor/coactivator recognition and the antagonism of this interaction by tamoxifen. Cell 95:927-37
13. Glass C K, Rosenfeld M G 2000 The coregulator exchange in transcriptional functions of nuclear receptors. Genes Dev 14:121-41
14. McKenna N J, O'Malley B W 2002 Minireview: nuclear receptor coactivators—an update. Endocrinology 143:2461-5
15. McKenna N J, O'Malley B W 2002 Combinatorial control of gene expression by nuclear receptors and coregulators. Cell 108:465-74

16. Shang Y, Brown M 2002 Molecular determinants for the tissue specificity of SERMs. Science 295:2465-8
17. Jordan V C 2001 The past, present, and future of selective estrogen receptor modulation. Ann N Y Acad Sci 949:72-9
18. Anderson H, Bulun S, Smith I, Dowsett M 2007 Predictors of response to aromatase inhibitors. J Steroid Biochem Mol Biol 106:49-54
19. Mao C, Patterson N M, Cheman M T, Aninye 10, Zhang C, Montoya J B, Cheng J, Putt K S, Hergenrother P J, Wilson E M, Nardulli A M, Nordeen S K, Shapiro D J 2008 A new small molecule inhibitor of estrogen receptor alpha binding to estrogen response elements blocks estrogen-dependent growth of cancer cells. J Biol Chem 283:12819-30
20. Wilson V S, Bobseine K, Gray L E, Jr. 2004 Development and characterization of a cell line that stably expresses an estrogen-responsive luciferase reporter for the detection of estrogen receptor agonist and antagonists. Toxicol Sci 81:69-77
21. ten Berge R L, Meijer C J, Dukers D F, Kummer J A, Bladergroen B A, Vos W, Hack C E, Ossenkoppele G J, Oudejans J J 2002 Expression levels of apoptosis-related proteins predict clinical outcome in anaplastic large cell lymphoma. Blood 99:4540-6
22. ten Berge R L, Oudejans J J, Ossenkoppele G J, Meijer C J 2003 ALK-negative systemic anaplastic large cell lymphoma: differential diagnostic and prognostic aspects-a review. J Pathol 200:4-15
23. van Houdt I S, Oudejans J J, van den Eertwegh A J, Baars A, Vos W, Bladergroen B A, Rimoldi D, Muris J J, Hooijberg E, Gundy C M, Meijer C J, Kummer J A 2005 Expression of the apoptosis inhibitor protease inhibitor 9 predicts clinical outcome in vaccinated patients with stage III and IV melanoma. Clin Cancer Res 11:6400-7
24. Kummer J A, Micheau O, Schneider P, Bovenschen N, Broekhuizen R, Quadir R, Strik M C, Hack C E, Tschopp J 2007 Ectopic expression of the serine protease inhibitor P19 modulates death receptor-mediated apoptosis. Cell Death Differ 14:1486-96
25. Jiang X, Ellison S J, Alarid E T, Shapiro D J 2007 Interplay between the levels of estrogen and estrogen receptor controls the level of the granzyme inhibitor, proteinase inhibitor 9 and susceptibility to immune surveillance by natural killer cells. Oncogene 26:4106-14
26. Jiang X, Orr B A, Kranz D M, Shapiro D J 2006 Estrogen induction of the granzyme B inhibitor, proteinase inhibitor 9, protects cells against apoptosis mediated by cytotoxic T lymphocytes and natural killer cells. Endocrinology 147:1419-26
27. Jiang X, Patterson N M, Ling Y, Xie J, Helferich W G, Shapiro D J, 2008 Endocrinology. 2008 November; 149(11):5366-73. Low concentrations of the soy phytoestrogen genistein induce proteinase inhibitor 9 and block killing of breast cancer cells by immune cells.
28. Cunningham T D, Jiang X, Shapiro D J 2007 Expression of high levels of human proteinase inhibitor 9 blocks both perforin/granzyme and Fas/Fas ligand-mediated cytotoxicity. Cell Immunol 245:32-41
29. Krieg A J, Krieg S A, Ahn B S, Shapiro D J 2004 Interplay between estrogen response element sequence and ligands controls in vivo binding of estrogen receptor to regulated genes. J Biol Chem 279:5025-34
30. Krieg S A, Krieg A J, Shapiro D J 2001 A unique downstream estrogen responsive unit mediates estrogen induction of proteinase inhibitor-9, a cellular inhibitor of IL-1beta converting enzyme (caspase 1). Mol Endocrinol 15:1971-82
31. Chen L, Fischle W, Verdin E, Greene W C 2001 Duration of nuclear NF-kappaB action regulated by reversible acetylation. Science 293:1653-7
32. Nordeen S K, Kuhnel B, Lawler-Heavner J, Barber D A, Edwards D P 1989 A quantitative comparison of dual control of a hormone response element by progestins and glucocorticoids in the same cell line. Mol Endocrinol 3:1270-8
33. Neuman E, Ladha M H, Lin N, Upton T M, Miller S J, DiRenzo J, Pestell R G, Hinds P W, Dowdy S F, Brown M, Ewen M E 1997 Cyclin D1 stimulation of estrogen receptor transcriptional activity independent of cdk4. Mol Cell Biol 17:5338-47
34. Musgrove E A, Lee C S, Buckley M F, Sutherland R L 1994 Cyclin D1 induction in breast cancer cells shortens G1 and is sufficient for cells arrested in G1 to complete the cell cycle. Proc Natl Acad Sci USA 91:8022-6
35. Sabbah M, Courilleau D, Mester J, Redeuilh G 1999 Estrogen induction of the cyclin D1 promoter: involvement of a cAMP response-like element. Proc Natl Acad Sci USA 96:11217-22
36. Kilker R L, Planas-Silva M D 2006 Cyclin D1 is necessary for tamoxifen-induced cell cycle progression in human breast cancer cells. Cancer Res 66:11478-84
37. Castro-Rivera E, Samudio I, Safe S 2001 Estrogen regulation of cyclin D1 gene expression in ZR-75 breast cancer cells involves multiple enhancer elements. J Biol Chem 276:30853-61
38. Zhou J H, Yu D V, Cheng J, Shapiro D J 2007 Delayed and persistent ERK1/2 activation is required for 4-hydroxytamoxifen-induced cell death. Steroids 72:765-77
39. Obrero M, Yu D V, Shapiro D J 2002 Estrogen receptor-dependent and estrogen receptorindependent pathways for tamoxifen and 4-hydroxytamoxifen-induced programmed cell death. Journal of Biological Chemistry 277:45695-703
40. Fowler A M, Solodin N M, Valley C C, Alarid E T 2006 Altered target gene regulation controlled by estrogen receptor-alpha concentration. Mol Endocrinol 20:291-301
41. Naughton C, MacLeod K, Kuske B, Clarke R, Cameron D A, Langdon S P 2007 Progressive loss of estrogen receptor alpha cofactor recruitment in endocrine resistance. Mol Endocrinol 21:2615-26
42. Fowler A M, Solodin N, Preisler-Mashek M T, Zhang P, Lee A V, Alarid E T 2004 Increases in estrogen receptor-alpha concentration in breast cancer cells promote serine 118/104/106-independent AF-1 transactivation and growth in the absence of estrogen. Faseb J 18:81-93
43. Howell A, Dodwell D J, Anderson H, Redford J 1992 Response after withdrawal of tamoxifen and progestogens in advanced breast cancer. Ann Oncol 3:611-7
44. Canney P A, Griffiths T, Latief T N, Priestman T J 1987 Clinical significance of tamoxifen withdrawal response. Lancet 1:36
45. Ishii Y, Waxman S, Germain D 2008 Tamoxifen stimulates the growth of cyclin D1-overexpressing breast cancer cells by promoting the activation of signal transducer and activator of transcription 3. Cancer Res 68:852-60
46. Wang L H, Yang X Y, Zhang X, An P, Kim H J, Huang J, Clarke R, Osborne C K, Inman J K, Appella E, Farrar W L 2006 Disruption of estrogen receptor DNA-binding domain and related intramolecular communication restores tamoxifen sensitivity in resistant breast cancer. Cancer Cell 10:487-99
47. Coradini D, Biffi A, Cappelletti V, Di Fronzo G 1995 Influence of different combinations of tamoxifen and toremifene on estrogen receptor-positive breast cancer cell lines. Cancer Detect Prev 19:348-54

48. Arteaga C L, Koli K M, Dugger T C, Clarke R 1999 Reversal of tamoxifen resistance of human breast carcinomas in vivo by neutralizing antibodies to transforming growth factor-beta. J Natl Cancer Inst 91:46-53
49. Schiff R, Massarweh S A, Shou J, Bharwani L, Mohsin S K, Osborne C K 2004 Cross-talk between estrogen receptor and growth factor pathways as a molecular target for overcoming endocrine resistance. Clin Cancer Res 10:331 S-6S
50. Anzick S L, Kononen J, Walker R L, Azorsa D O, Tanner M M, Guan X Y, Sauter G, Kallioniemi O P, Trent J M, Meltzer P S 1997 AIB1, a steroid receptor coactivator amplified in breast and ovarian cancer. Science 277:965-8
51. Reese J C, Katzenellenbogen B S 1992 Examination of the DNA-binding ability of estrogen receptor in whole cells: implications for hormone-independent transactivation and the actions of antiestrogens. Mol Cell Biol 12:4531-8
52. Kisanga E R, Gjerde J, Guerrieri-Gonzaga A, Pigatto F, Pesci-Feltri A, Robertson C, Serrano D, Pelosi G, Decensi A, Lien E A 2004 Tamoxifen and metabolite concentrations in serum and breast cancer tissue during three dose regimens in a randomized preoperative trial. Clin Cancer Res 10:2336-43
53. Estebanez-Perpina E, Arnold A A, Nguyen P, Rodrigues E D, Mar E, Bateman R, Pallai P, Shokat K M, Baxter J D, Guy R K, Webb P, Fletterick R J 2007 A surface on the androgen receptor that allosterically regulates coactivator binding. Proc Natl Acad Sci USA 104:16074-9
54. ten Berge R L, de Bruin P C, Oudejans J J, Ossenkoppele G J, van der Valk P, Meijer C J 2003 ALK-negative anaplastic large-cell lymphoma demonstrates similar poor prognosis to peripheral T-cell lymphoma, unspecified. Histopathology 43:462-9
55. Grillo M, Bott M J, Khandke N, McGinnis J P, Miranda M, Meyyappan M, Rosfjord E C, Rabindran S K 2006 Validation of cyclin D1/CDK4 as an anticancer drug target in MCF7 breast cancer cells: Effect of regulated overexpression of cyclin D1 and siRNAmediated inhibition of endogenous cyclin D1 and CDK4 expression. Breast Cancer Res Treat 95:185-94
56. Chen C D, Welsbie D S, Tran C, Baek S H, Chen R, Vessella R, Rosenfeld M G, Sawyers C L 2004 Molecular determinants of resistance to antiandrogen therapy. Nat Med 10:33-9
57. Lewis J S, Jordan V C 2005 Selective estrogen receptor modulators (SERMs): mechanisms of anticarcinogenesis and drug resistance. Mutat Res 591:247-63 58. Thorpe S M, Christensen I J, Rasmussen B B, Rose C 1993 Short recurrence-free survival associated with high oestrogen receptor levels in the natural history of postmenopausal, primary breast cancer. Eur J Cancer 29A:971-7
59. Romain S, Chinot O, Guirou O, Soulliere M, Martin P M 1994 Biological heterogeneity of ER-positive breast cancers in the post-menopausal population. Int J Cancer 59:17-9 60. Abukhdeir A M, Vitolo M I, Argani P, De Marzo A M, Karakas B, Konishi H, Gustin J P, Lauring J, Garay J P, Pendleton C, Konishi Y, Blair B G, Brenner K, Garrett-Mayer E, Carraway H, Bachman K E, Park B H 2008 Tamoxifen-stimulated growth of breast cancer due to p21 loss. Proc Natl Acad Sci USA 105:288-93
61. Hoffmann J, Bohlmann R, Heinrich N, Hofmeister H, Kroll J, Kunzer H, Lichtner R B, Nishino Y, Parczyk K, Sauer G, Gieschen H, Ulbrich H F, Schneider M R 2004 Characterization of new estrogen receptor destabilizing compounds: effects on estrogensensitive and tamoxifen-resistant breast cancer. J Natl Cancer Inst 96:210-8

SEQUENCE LISTING. Any sequence listing information is part of the specification herewith.

OTHER REFERENCES

U.S. Pat. No. 7,253,176 by Waer, et al., Aug. 7, 2007 for Immunosuppressive effects of 8-substituted xanthine derivatives.
International Publications WO2007065595; WO2007105023; WO04106337.
Wang, L. H. Yang, X Y, Zhang X, et al., and Farrar W L 2006. Disruption of estrogen receptor DNA binding domain and related intracellular communication restores tamoxifen sensitivity in resistant breast cancer. Cancer Cell 10: 487-499.
Estebanez-Perpina, E et al., and Fletterick R J. 2007. A surface on the androgen receptor that allosterically regulates coactivator binding. Proc. Natl. Acad. Sci. USA 104(41) 16074-16079
Hager, Geo. P.; Kramer, Stanley P. Aryl ketones and thio morpholides in the synthesis of 8-substituted xanthines. Journal of the American Pharmaceutical Association (1912-1977) (1955), 44 649-53.
Kostolansky, A.; Mokry, J.; Tamchyna, J. Sloven. Akad. Vied., Bratislava, Czech. Chemicke Zvesti (1956), 10 96-109. The preparation of some structure hybrids of N-methylated xanthine and 2-substituted imidazoles.
Mao C. et al., 2008, J Biol Chem. May 9; 283(19):12819-30. Epub 2008 Mar. 12. A new small molecule inhibitor of estrogen receptor alpha binding to estrogen response elements blocks estrogen-dependent growth of cancer cells.

STATEMENTS REGARDING INCORPORATION BY REFERENCE AND VARIATIONS

All references mentioned throughout this application, for example patent documents including issued or granted patents or equivalents; patent application publications; unpublished patent applications; and non-patent literature documents or other source material; are hereby incorporated by reference herein in their entireties, as though individually incorporated by reference. In the event of any inconsistency between cited references and the disclosure of the present application, the disclosure herein takes precedence. Some references provided herein are incorporated by reference to provide information, e.g., details concerning sources of starting materials, additional starting materials, additional reagents, additional methods of synthesis, additional methods of analysis, additional biological materials, additional cells, and additional uses of the invention.

All patents and publications mentioned herein are indicative of the levels of skill of those skilled in the art to which the invention pertains. References cited herein can indicate the state of the art as of their publication or filing date, and it is intended that this information can be employed herein, if needed, to exclude specific embodiments that are in the prior art. For example, when composition of matter are claimed herein, it should be understood that compounds known and available in the art prior to Applicant's invention, including compounds for which an enabling disclosure is provided in the references cited herein, are not intended to be included in the composition of matter claims herein.

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Thus as used herein, comprising is synonymous with including, containing, having, or characterized by, and is inclusive or open-ended and does not exclude additional, unrecited elements or method steps. As used herein, "consisting of" excludes any element, step, or ingredient, etc. not specified in the claim description. As used herein, "consisting essentially of" does not exclude materials or steps that do not materially affect the basic and novel characteristics of the claim (e.g., relating to an active ingredient). In each instance herein any of the terms "comprising", "consisting essentially of" and "consisting of" may be replaced with at least either of the other two terms, thereby disclosing separate embodiments and/or scopes which are not necessarily coextensive. An embodiment of the invention illustratively described herein suitably may be practiced in the absence of any element or elements or limitation or limitations not specifically disclosed herein.

Whenever a range is disclosed herein, e.g., a temperature range, time range, composition or concentration range, or other value range, etc., all intermediate ranges and subranges as well as all individual values included in the ranges given are intended to be included in the disclosure. This invention is not to be limited by the embodiments disclosed, including any shown in the drawings or exemplified in the specification, which are given by way of example or illustration and not of limitation. It will be understood that any subranges or individual values in a range or subrange that are included in the description herein can be excluded from the claims herein.

The invention has been described with reference to various specific and/or preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be employed in the practice of the invention as broadly disclosed herein without resort to undue experimentation; this can extend, for example, to starting materials, biological materials, reagents, synthetic methods, purification methods, analytical methods, assay methods, and biological methods other than those specifically exemplified. All art-known functional equivalents of the foregoing (e.g., compositions, methods, devices, device elements, materials, procedures and techniques, etc.) described herein are intended to be encompassed by this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, preferred embodiments, and optional features, modification and variation of the concepts herein disclosed may be resorted to by those skilled in the art, and that such modifications and variations are considered to be within the scope of this invention as defined by the appended claims.

We claim:

1. A method of inhibiting growth of a cancer cell comprising contacting said cell with an effective amount of a compound having formula FX2:

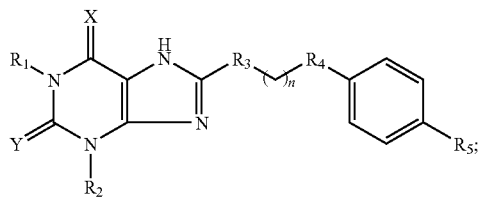

FX2 wherein X or Y each independently is S, O, or Se;

$R_1$ or $R_2$ each independently is H or $C_{1-6}$ alkyl;

$R_3$ is —S—$CH_2$, —O—$CH_2$—, —$CH_2$—S, or —$CH_2$—O—;

$R_4$ is —C=O, —NH—C=O, —$CH_2$—, or null;

$R_5$ is F, Cl, Br, I, At, H, or other group with electronegativity from 1.5 to 4.0; and n is 1 to 6.

2. The method of claim 1 wherein the cancer cell is a human cancer cell.

3. The method of claim 1 wherein the cancer cell is a breast cancer cell.

4. The method of claim 1 wherein the cancer cell is a resistant cancer cell.

5. The method of claim 4 wherein said resistant cancer cell has resistance to a chemotherapeutic agent selected from the group consisting of tamoxifen, 4-hydroxytamoxifen (OHT); a selective estrogen receptor modulator, and an aromatase inhibitor.

6. The method of claim 1 wherein the compound has a structural formula selected from the group consisting of compounds having formulas corresponding to TPSF/97998, 99676, and TPBM/95910:

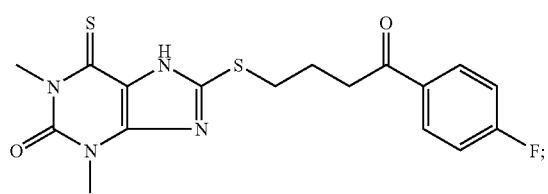 [SMILES: Cn1c(=S)c2[nH]c(SCCCC(=O)c3ccc(F)cc3)nc2n(C)c1=O]

TPSF/97998

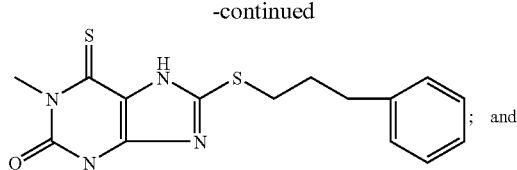

99676

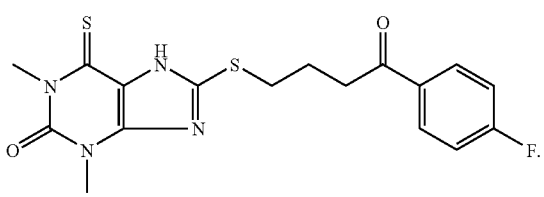 [SMILES: Cn1c(=S)c2[nH]c(SCCCC(=O)c3ccc(F)cc3)nc2n(C)c1=O]

TPBM/95910

7. The method of claim 1 wherein the compound has a structural formula of compound TPSF/97998,

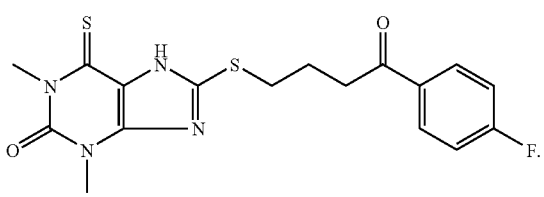 [SMILES: Cn1c(=S)c2[nH]c(SCCCC(=O)c3ccc(F)cc3)nc2n(C)c1=O]

8. A method of inhibiting growth of a cancer cell comprising contacting said cell with an effective amount of a compound having formula FX1:

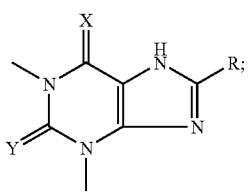

FX1 wherein X and Y independently can be oxygen or sulfur; R can be A, B, C, or D; wherein A is alkyl; B is thioalkyl; C is arylalkyl, and D is cycloalkyl; and wherein each component A, B, C, or D independently is optionally substituted.

9. The method of claim 8 wherein the compound is selected from the group consisting of compounds having formulas corresponding to TPSF/97998, 99676, TPEP/74361, and TPBM/95910:

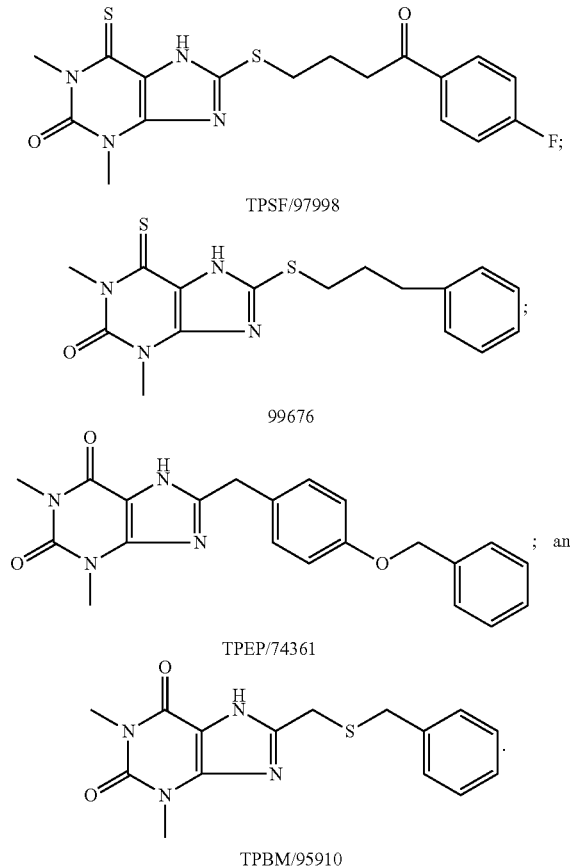

10. A method of treating cancer comprising administering to a patient in need thereof an effective amount of a compound having formula FX2 or a pharmaceutical formulation thereof:

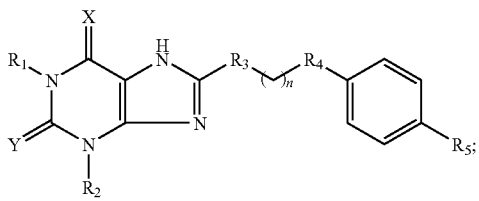

wherein X or Y each independently is S, O, or Se;
R$_1$ or R$_2$ each independently is H or C$_{1-6}$ alkyl;
R$_3$ is —S—CH$_2$, —O—CH$_2$—, —CH$_2$—S, or —CH$_2$—O—;
R$_4$ is —C=O, —NH—C=O, —CH$_2$—, or null;
R$_5$ is F, Cl, Br, I, At, H, or other group with electronegativity from 1.5 to 4.0; and
n is 1 to 6.

11. The method of claim 10 wherein said cancer is human breast cancer.

12. The method of claim 10 wherein said cancer is a resistant cancer.

13. The method of claim 12 wherein said resistant cancer has resistance to a chemotherapeutic agent selected from the group consisting of tamoxifen, 4-hydroxytamoxifen (OHT); a selective estrogen receptor modulator, and an aromatase inhibitor.

14. The method of claim 10 wherein said cancer is a resistant breast cancer.

15. The method of claim 10 wherein the compound has a structural formula selected from the group consisting of compounds having formulas corresponding to TPSF/97998, 99676, and TPBM/95910:

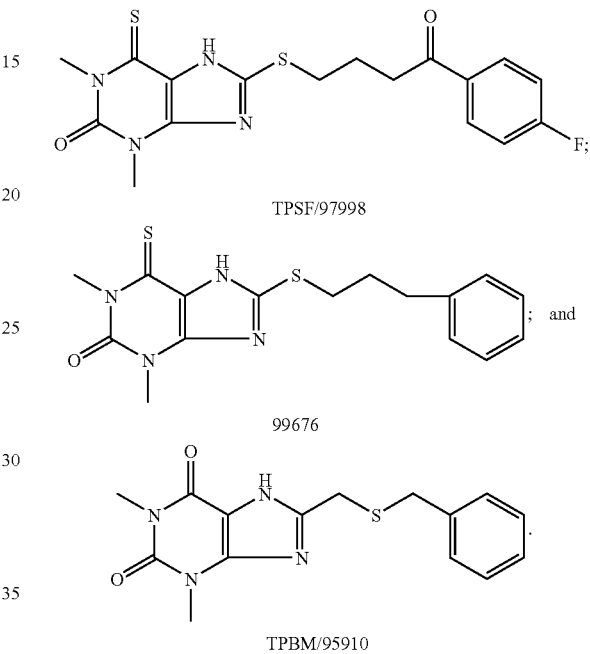

16. The method of claim 10 wherein the compound has a structural formula of compound TPSF/97998,

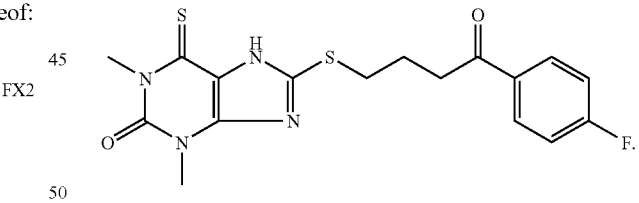

17. A method of treating cancer comprising administering to a patient in need thereof an effective amount of a compound having formula FX1 or a pharmaceutical formulation thereof:

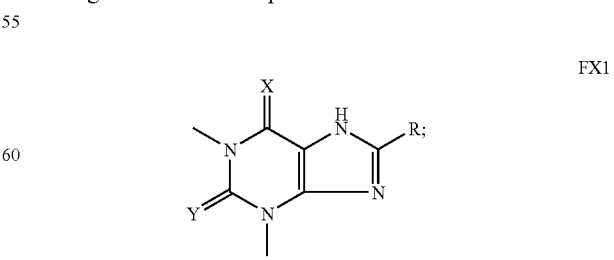

wherein X and Y independently can be oxygen or sulfur; R can be A, B, C, or D; wherein A is alkyl; B is thioalkyl;

C is arylalkyl, and D is cycloalkyl; and wherein each component A, B, C, or D independently is optionally substituted.

18. The method of claim 17 wherein said cancer is human breast cancer.

19. The method of claim 17 wherein said cancer is a resistant cancer.

20. The method of claim 17 wherein the compound is selected from the group consisting of compounds having formulas corresponding to TPSF/97998, 99676, TPEP/74361, and TPBM/95910:

TPSF/97998

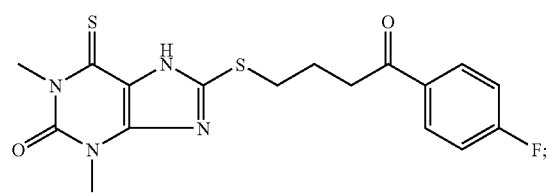

99676

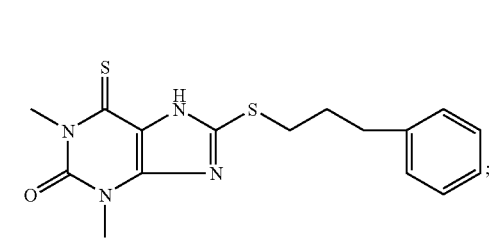

TPEP/74361

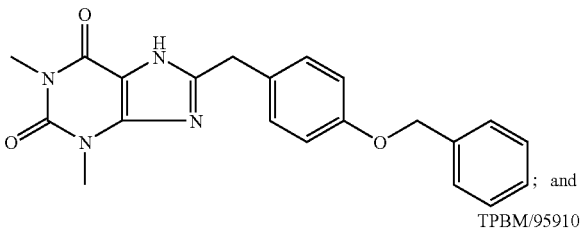

; and

TPBM/95910

21. The method of claim 17 wherein the compound has a structural formula of compound TPSF/97998,

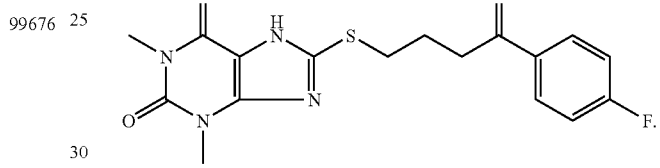

* * * * *